US012774476B2

(12) United States Patent
Standage-Beier et al.

(10) Patent No.: US 12,774,476 B2
(45) Date of Patent: Oct. 27, 2026

(54) CAS9 FUSION PROTEINS AND RELATED METHODS

(71) Applicant: ARIZONA BOARD OF REGENTS ON BEHALF OF ARIZONA STATE UNIVERSITY, Scottsdale, AZ (US)

(72) Inventors: Kylie Standage-Beier, Phoenix, AZ (US); Parithi Balachandran, Coimbatore (IN); Nicholas Brookhouser, Tempe, AZ (US); David Brafman, Phoenix, AZ (US); Xiao Wang, Chandler, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 994 days.

(21) Appl. No.: 17/602,581

(22) PCT Filed: Apr. 14, 2020

(86) PCT No.: PCT/US2020/028149

§ 371 (c)(1),
(2) Date: Oct. 8, 2021

(87) PCT Pub. No.: WO2020/214610

PCT Pub. Date: Oct. 22, 2020

(65) Prior Publication Data

US 2023/0193322 A1 Jun. 22, 2023

Related U.S. Application Data

(60) Provisional application No. 62/834,880, filed on Apr. 16, 2019.

(51) Int. Cl.
*C12N 15/90* (2006.01)
*C12N 9/16* (2006.01)
*C12N 9/22* (2006.01)
*C12N 15/11* (2006.01)

(52) U.S. Cl.
CPC ............ *C12N 15/907* (2013.01); *C12N 9/16* (2013.01); *C12N 9/22* (2013.01); *C12N 15/11* (2013.01); *C12Y 301/21* (2013.01); *C12N 2310/20* (2017.05); *C12N 2800/80* (2013.01)

(58) Field of Classification Search
CPC ....... C12N 9/22; C12N 2310/20; C12N 15/90
See application file for complete search history.

(56) References Cited

U.S. PATENT DOCUMENTS

| | | | | |
|---|---|---|---|---|
| 8,993,233 B2 | 3/2015 | Zhang | | |
| 2006/0172373 A1* | 8/2006 | Stark | C12N 9/00 435/232 | |
| 2015/0071899 A1 | 3/2015 | Liu | | |
| 2016/0122405 A1 | 5/2016 | Palchaudhuri | | |
| 2016/0215276 A1* | 7/2016 | Liu | C12N 15/907 | |
| 2020/0283755 A1* | 9/2020 | Zhang | A61K 48/00 | |

FOREIGN PATENT DOCUMENTS

| | | |
|---|---|---|
| WO | 2017216771 | 12/2017 |
| WO | 2018031683 | 2/2018 |
| WO | 2019051237 | 3/2019 |

OTHER PUBLICATIONS

Jakubowski, H., & Flatt, P. (Mar. 19, 2025). Chromosomes and Chromatin. College of St. Benedict/St. John's University and Western Oregon University. https://bio.libretexts.org/@go/page/14964 (Year: 2025).*

Zhang, Jian-Hua, et al. "Optimization of genome editing through CRISPR-Cas9 engineering." Bioengineered 7.3 (2016): 166-174. (Year: 2016).*

Prorocic, Marko M., et al. "Zinc-finger recombinase activities in vitro." Nucleic acids research 39.21 (2011): 9316-9328. (Year: 2011).*

Grindley, Nigel DF, Katrine L. Whiteson, and Phoebe A. Rice. "Mechanisms of site-specific recombination." Annu. Rev. Biochem. 75.1 (2006): 567-605. (Year: 2006).*

Akopian, A.; He, J.; Boocock, M. R.; Stark, W. M. "Chimeric Recombinases with Designed DNA Sequence Recognition." Proc. Natl. Acad. Sci. 2003, 100 (15), 8688-8691. https://doi.org/10.1073/pnas.1533177100.

Arnold, P. H.; Blake, D. G.; Grindley, N. D.; Boocock, M. R.; Stark, W. M. "Mutants of Tn3 Resolvase Which Do Not Require Accessory Binding Sites for Recombination Activity." EMBO J. 1999, 18 (5), 1407-1414. https://doi.org/10.1093/emboj/18.5.1407.

Barrangou, R.; Doudna, J. A. "Applications of CRISPR Technologies in Research and Beyond." Nat. Biotechnol. 2016, 933-941.

Barrangou, R.; Fremaux, C.; Deveau, H.; Richards, M.; Boyaval, P.; Moineau, S.; Romero, D. A.; Horvath, P. "CRISPR Provides Acquired Resistance Against Viruses in Prokaryotes." Science 2007, 315 (5819), 1709-1712. 16.

Brafman, D.; Willert, K. "Gene Transduction Approaches in Human Embryonic Stem Cells." Methodol. Adv. Cult. Manip. Util. Embryonic Stem Cells Basic Pract. Appl. 2011. https://doi.org/10.5772/14163. 20 pages.

Brookhouser, N.; Raman, S.; Potts, C.; Brafman, D. A. "May I Cut in? Gene Editing Approaches in Human Induced Pluripotent Stem Cells." Cells 2017, 6 (1). https://doi.org/10.3390/cells6010005. 21 pages.

(Continued)

*Primary Examiner* — Teresa E Knight
*Assistant Examiner* — Michael Angelo Riga
(74) *Attorney, Agent, or Firm* — FULLER IP LAW LLC; Rodney J. Fuller

(57) ABSTRACT

Disclosed are recombinant Cas9 proteins, methods of production, and methods of use for targeted DNA deletions, DNA insertions, or both in a eukaryotic genome. An assay system for evaluating the ability of the recombinant Cas9 proteins for targeted DNA deletions, DNA insertions, or both in a eukaryotic genome is also disclosed.

11 Claims, 17 Drawing Sheets

Specification includes a Sequence Listing.

(56) References Cited

OTHER PUBLICATIONS

Casini, A.; Olivieri, M.; Petris, G.; Montagna, C.; Reginato, G.; Maule, G.; Lorenzin, F.; Prandi, D.; Romanel, A.; Demichelis, F.; et al. "A Highly Specific SpCas9 Variant Is Identified by in Vivo Screening in Yeast." Nat. Biotechnol. 2018, 36 (3), 265. 11 pages.
Chaikind, B.; Bessen, J. L.; Thompson, D. B.; Hu, J. H.; Liu, D. R. "A Programmable Cas9-Serine Recombinase Fusion Protein That Operates on DNA Sequences in Mammalian Cells." Nucleic Acids Res. 2016, 44 (20), 9758-9770. https://doi.org/10.1093/nar/gkw707.
Chatterjee, P.; Jakimo, N.; Jacobson, J. M. "Minimal PAM Specificity of a Highly Similar SpCas9 Ortholog." Sci. Adv. 2018, 4 (10), eaau0766. https://doi.org/10.1126/sciadv.aau0766.
Chiu, T.- Y.; Jiang, J.-H. R. "Logic Synthesis of Recombinase-Based Genetic Circuits." Sci. Rep. 2017, 7 (1), 12873. 13 pages.
Cong, L.; Ran, F. A.; Cox, D.; Lin, S.; Barretto, R.; Habib, N.; Hsu, P. D.; Wu, X.; Jiang, W.; Marraffini, L. A.; et al. "Multiplex Genome Engineering Using CRISPR/Cas Systems." Science 2013, 339 (6121), 819-823. https://doi.org/10.1126/science.1231143.
Cremer, T.; Cremer, M. "Chromosome Territories." Cold Spring Harb. Perspect. Biol. 2010, 2 (3). https://doi.org/10.1101/cshperspect.a003889.
DiCarlo, J. E.; Norville, J. E.; Mali, P.; Rios, X.; Aach, J.; Church, G. M. "Genome Engineering in *Saccharomyces cerevisiae* Using CRISPR-Cas Systems." Nucleic Acids Res. 2013, 41 (7), 4336-4343. https://doi.org/10.1093/nar/gkt135.
Doyon, Y.; McCammon, J. Miller, J. C.; Faraji, Ngo, Katibah, G. Amora, R.; Hocking, T. D.; Zhang, L.; Rebar, E. J.; et al. "Heritable Targeted Gene Disruption in Zebrafish Using Designed Zinc-Finger Nucleases." Nat. Biotechnol. 2008, 26 (6), 702-708.
Dymond, J. S.; Richardson, S. M.; Coombes, C. E.; Babatz, T.; Muller, H.; Annaluru, N.; Blake, W. J.; Schwerzmann, J. W.; Dai, J.; Lindstrom, D. L.; et al. "Synthetic Chromosome Arms Function in Yeast and Generate Phenotypic Diversity by Design." Nature 2011, 477 (7365), 471-476.
Ellis, T.; Wang, X.; Collins, J. J. "Diversity-Based, Model-Guided Construction of Synthetic Gene Networks with Predicted Functions." Nat. Biotechnol. 2009, 27 (5), 465-471. https://doi.org/10.1038/nbt.1536.
Farzadfard, F.; Lu, T. K. "Genomically Encoded Analog Memory with Precise in Vivo DNA Writing in Living Cell Populations." Science 2014, 346 (6211), 1256272. 10 pages.
Fu, Y.; Foden, J. A.; Khayter, C.; Maeder, M. L.; Reyon, D.; Joung, J. K.; Sander, J. D. "High-Frequency off-Target Mutagenesis Induced by CRISPR-Cas Nucleases in Human Cells." Nat. Biotechnol. 2013, 31 (9), 822-826. https://doi.org/10.1038/nbt.2623.
Gaj, T.; Mercer, A. C.; Gersbach, C. A.; Gordley, R. M.; Barbas, C. F. "Structure-Guided Reprogramming of Serine Recombinase DNA Sequence Specificity." Proc. Natl. Acad. Sci. 2011, 108 (2), 498-503. https://doi.org/10.1073/pnas.1014214108.
Gaj, T.; Mercer, A. C.; Sirk, S. J.; Smith, H. L.; Barbas, C. F. "A Comprehensive Approach to Zinc-Finger Recombinase Customization Enables Genomic Targeting in Human Cells." Nucleic Acids Res. 2013, 41 (6), 3937-3946. https://doi.org/10.1093/nar/gkt071.
Gaj, T.; Sirk, S. J.; Barbas, C. F. "Expanding the Scope of Site-Specific Recombinases for Genetic and Metabolic Engineering." Biotechnol. Bioeng. 2014, 111 (1), 1-15. https://doi.org/10.1002/bit.25096.
Gordley, R. M.; Gersbach, C. A.; Barbas, C. F. "Synthesis of Programmable Integrases." Proc. Natl. Acad. Sci. 2009, 106 (13), 5053-5058. https://doi.org/10.1073/pnas.0812502106.
Gordley, R. M.; Smith, J. D.; Gräslund, T.; Barbas, C. F. "Evolution of Programmable Zinc Finger-Recombinases with Activity in Human Cells." J. Mol. Biol. 2007, 367 (3), 802-813. https://doi.org/10.1016/j.jmb.2007.01.017.
Grindley, N. D. F.; Whiteson, K. L.; Rice, P. A. "Mechanisms of Site-Specific Recombination." Annu. Rev. Biochem. 2006, 75 (1), 567-605. https://doi.org/10.1146/annurev.biochem.73.011303.073908.
Guilinger, J. P.; Thompson, D. B.; Liu, D. R. "Fusion of Catalytically Inactive Cas9 to FokI Nuclease Improves the Specificity of Genome Modification." Nat. Biotechnol. 2014, 32 (6), 577-582. https://doi.org/10.1038/nbt.2909.
Haapaniemi, E.; Botla, S.; Persson, J.; Schmierer, B.; Taipale, J. "CRISPR-Cas9 Genome Editing Induces a P53-Mediated DNA Damage Response." Nat. Med. 2018, 24 (7), 927. https://doi.org/10.1038/s41591-018-0049-z.
Hartley, J. L.; Temple, G. F.; Brasch, M. A. "DNA Cloning Using in Vitro Site-Specific Recombination." Genome Res. 2000, 10 (11), 1788-1795.
He, X.; Tan, C.; Wang, F.; Wang, Y.; Zhou, R.; Cui, D.; You, W.; Zhao, H.; Ren, J.; Feng, B. "Knock-in of Large Reporter Genes in Human Cells via CRISPR/Cas9-Induced Homology-Dependent and Independent DNA Repair." Nucleic Acids Res. 2016, 44 (9), e85. https://doi.org/10.1093/nar/gkw064.
Hu, J. H.; Miller, S. M.; Geurts, M. H.; Tang, W.; Chen, L.; Sun, N.; Zeina, C. M.; Gao, X.; Rees, H. A.; Lin, Z.; et al. "Evolved Cas9 Variants with Broad PAM Compatibility and High DNA Specificity." Nature 2018, 556 (7699), 57-63. https://doi.org/10.1038/nature26155.
Ihry, R. J.; Worringer, K. A.; Salick, M. R.; Frias, E.; Ho, D.; Theriault, K.; Kommineni, S.; Chen, J.; Sondey, M.; Ye, C.; et al. "P53 Inhibits CRISPR-Cas9 Engineering in Human Pluripotent Stem Cells." Nat. Med. 2018, 24 (7), 939-946. https://doi.org/10.1038/s41591-018-0050-6.
Karpinski, J.; Hauber, I.; Chemnitz, J.; Schäfer, C.; Paszkowski-Rogacz, M.; Chakraborty, D.; Beschorner, N.; Hofmann-Sieber, H.; Lange, U. C.; Grundhoff, A.; et al. "Directed Evolution of a Recombinase That Excises the Provirus of Most HIV-1 Primary Isolates with High Specificity." Nat. Biotechnol. 2016, 34 (4), 401-409. https://doi.org/10.1038/nbt.3467.
Komor, A. C.; Kim, Y. B.; Packer, M. S.; Zuris, J. A.; Liu, D. R. "Programmable Editing of a Target Base in Genomic DNA without Double-Stranded DNA Cleavage." Nature 2016, 533 (7603), 420-424. https://doi.org/10.1038/nature17946.
Komor, A. C.; Zhao, K. T.; Packer, M. S.; Gaudelli, N. M.; Waterbury, A. L.; Koblan, L. W.; Kim, Y. B.; Badran, A. H.; Liu, D. R. "Improved Base Excision Repair Inhibition and Bacteriophage Mu Gam Protein Yields C:G-to-T:A Base Editors with Higher Efficiency and Product Purity." Sci. Adv. 2017, 3 (8), eaao4774. https://doi.org/10.1126/sciadv.aao4774.
Kosicki, M.; Tomberg, K.; Bradley, A. "Repair of Double-Strand Breaks Induced by CRISPR-Cas9 Leads to Large Deletions and Complex Rearrangements." Nat. Biotechnol. 2018, 36 (8), 765-771. https://doi.org/10.1038/nbt.4192.
Li, W.; Kamtekar, S.; Xiong, Y.; Sarkis, G. J.; Grindley, N. D. F.; Steitz, T. A. "Structure of a Synaptic ⌈σ Resolvase Tetramer Covalently Linked to Two Cleaved DNAs." Science 2005, 309 (5738), 1210-1215. https://doi.org/10.1126/science.1112064.
Mali, P.; Yang, L.; Esvelt, K. M.; Aach, J.; Guell, M.; DiCarlo, J. E.; Norville, J. E.; Church, G. M. "RNA-Guided Human Genome Engineering via Cas9." Science 2013, 339 (6121), 823-826. https://doi.org/10.1126/science.1232033.
Mercer, A. C.; Gaj, T.; Fuller, R. P.; Barbas, C. F. "Chimeric TALE Recombinases with Programmable DNA Sequence Specificity." Nucleic Acids Res. 2012, gks875. 10 pages. https://doi.org/10.1093/nar/gks875.
Nami, F.; Basiri, M.; Satarian, L.; Curtiss, C.; Baharvand, H.; Verfaillie, C. "Strategies for In Vivo Genome Editing in Nondividing Cells." Trends Biotechnol. 2018, 36 (8), 770-786. https://doi.org/10.1016/j.tibtech.2018.03.004.
Nishimasu, H.; Ran, F. A.; Hsu, P. D.; Konermann, S.; Shehata, S. I.; Dohmae, N.; Ishitani, R.; Zhang, F.; Nureki, O. "Crystal Structure of Cas9 in Complex with Guide RNA and Target DNA." Cell 2014, 156 (5), 935-949. https://doi.org/10.1016/j.cell.2014.02.001.
Nöllmann, M.; Byron, O.; Stark, W. M. "Behavior of Tn3 Resolvase in Solution and Its Interaction with Res." Biophys. J. 2005, 89 (3), 1920-1931. https://doi.org/10.1529/biophysj.104.058164.
Olorunniji, F. Stark, W. M. "The Catalytic Residues of Tn3 Resolvase." Nucleic Acids Res. 2009, 37 (22), 7590-7602.
Orthwein, A.; Noordermeer, S. M.; Wilson, M. D.; Landry, S.; Enchev, R. I.; Sherker, A.; Munro, M.; Pinder, J.; Salsman, J.;

(56) References Cited

OTHER PUBLICATIONS

Dellaire, G.; et al. "A Mechanism for the Suppression of Homologous Recombination in G1 Cells." Nature 2015, advance online publication. 18 pages. https://doi.org/10.1038/nature16142.
Perli, S. D.; Cui, C. H.; Lu, T. K. "Continuous Genetic Recording with Self-Targeting CRISPR-Cas in Human Cells." Science 2016, 353 (6304), aag0511. 12 pages.
Prorocic, M. M.; Wenlong, D.; Olorunniji, F. J.; Akopian, A.; Schloetel, J.-G .; Hannigan, A.; McPherson, A. L.; Stark, W. M. "Zinc-Finger Recombinase Activities in Vitro." Nucleic Acids Res. 2011, 39 (21), 9316-9328. https://doi.org/10.1093/nar/gkr652.
Sander, J. D.; Joung, J. K. "CRISPR-Cas Systems for Editing, Regulating and Targeting Genomes." Nat. Biotechnol. 2014, 32 (4), 347-355. https://doi.org/10.1038/nbt.2842.
Schmid-Burgk, J. L.; Höning, K.; Ebert, T. S.; Hornung, V. "CRISPaint Allows Modular Base-Specific Gene Tagging Using a Ligase-4-Dependent Mechanism." Nat. Commun. 2016, 7, 12338. 12 pages. https://doi.org/10.1038/ncomms12338.
Sikorski, R. S.; Hieter, P. A "System of Shuttle Vectors and Yeast Host Strains Designed for Efficient Manipulation of DNA in *Saccharomyces cerevisiae*." Genetics 1989, 122 (1), 19-27.
Siuti, P.; Yazbek, J.; Lu, T. K. "Synthetic Circuits Integrating Logic and Memory in Living Cells." Nat. Biotechnol. 2013, 31 (5), 448-452. https://doi.org/10.1038/nbt.2510.
St-Pierre, F.; Cui, L.; Priest, D. G.; Endy, D.; Dodd, I. B.; Shearwin, K. E. "One-Step Cloning and Chromosomal Integration of DNA." ACS Synth. Biol. 2013, 2 (9), 537-541. https://doi.org/10.1021/sb400021j.
Standage-Beier, K., "Development of CRISPR-RNA Guided Recombinases for Genome Engineering", Masters Thesis, Arizona State University, (Apr. 30, 2018), pp. 1-26, URL: https://repository.asu.edu/attachments/201273/content/StandageBeier_asu_0010N_17958.pdf, (Jul. 8, 2020), XP055750179.
Standage-Beier, K.; Wang, X. "Genome Reprogramming for Synthetic Biology." Front. Chem. Sci. Eng. 2017, 11 (1), 37-45. https://doi.org/10.1007/s11705-017-1618-2.
Standage-Beier, K.; Zhang, Q.; Wang, X. "Targeted Large-Scale Deletion of Bacterial Genomes Using CRISPR-Nickases." ACS Synth. Biol. 2015, 4 (11), 1217-1225. https://doi.org/10.1021/acssynbio.5b00132.
Suzuki, K.; Tsunekawa, Y.; Hernandez-Benitez, R.; Wu, J.; Zhu, J.; Kim, E. J.; Hatanaka, F.; Yamamoto, M.; Araoka, T.; Li, Z.; et al. "In Vivo Genome Editing via CRISPR/Cas9 Mediated Homology-Independent Targeted Integration." Nature 2016, 540 (7631), 144-149. https://doi.org/10.1038/nature20565.
Tang, W.; Liu, D. R. "Rewritable Multi-Event Analog Recording in Bacterial and Mammalian Cells." Science 2018, eaap8992. 12 pages.
Thyagarajan, B.; Olivares, E. C.; Hollis, R. P.; Ginsburg, D. S.; Calos, M. P. "Site-Specific Genomic Integration in Mammalian Cells Mediated by Phage PhiC31 Integrase." Mol. Cell. Biol. 2001, 21 (12), 3926-3934.
Wang, J. C. "Helical Repeat of DNA in Solution." Proc. Natl. Acad. Sci. 1979, 76 (1), 200-203. https://doi.org/10.1073/pnas.76.1.200.9770.
Weinberg, B. H.; Pham, N. T. H.; Caraballo, L. D.; Lozanoski, T.; Engel, A.; Bhatia, S.; Wong, W. W. "Large-Scale Design of Robust Genetic Circuits with Multiple Inputs and Outputs for Mammalian Cells." Nat. Biotechnol. 2017, 35 (5), 453-462. https://doi.org/10.1038/nbt.3805.
Winston, F.; Dollard, C.; Ricupero-Hovasse, S. L. "Construction of a Set of Convenient *Saccharomyces cerevisiae* Strains That Are Isogenic to S288C." Yeast Chichester Engl. 1995, 11 (1), 53-55.
Yang, L.; Nielsen, A. A. K.; Fernandez-Rodriguez, J.; McClune, C. J.; Laub, M. T.; Lu, T. K.; Voigt, "C. A. Permanent Genetic Memory with >1-Byte Capacity. Nat." Methods 2014, 11 (12), 1261-1266. https://doi.org/10.1038/nmeth.3147.
Yang, W.; Steitz, T. A. "Crystal Structure of the Site-Specific Recombinase Gamma Delta Resolvase Complexed with a 34 Bp Cleavage Site." Cell 1995, 82 (2), 193-207.
Zetsche, B.; Gootenberg, J. S.; Abudayyeh, O. O.; Slaymaker, I. M.; Makarova, K. S.; Essletzbichler, P.; Volz, S. E.; Joung, J.; van der Oost, J.; Regev, A.; et al. "Cpf1 Is a Single RNA-Guided Endonuclease of a Class 2 CRISPR-Cas System." Cell 2015, 163 (3), 759-771. https://doi.org/10.1016/j.cell.2015.09.038.
Zuo, Huo, X.; Yao, X.; 1-111, sun, Y.; Yin, J.; He, B.; Wang, X.; Shi, L.; Ping, J.; et al. "CRISPR/Cas9-Mediated Targeted Chromosome Elimination." Genome Biol. 2017, 18.

* cited by examiner

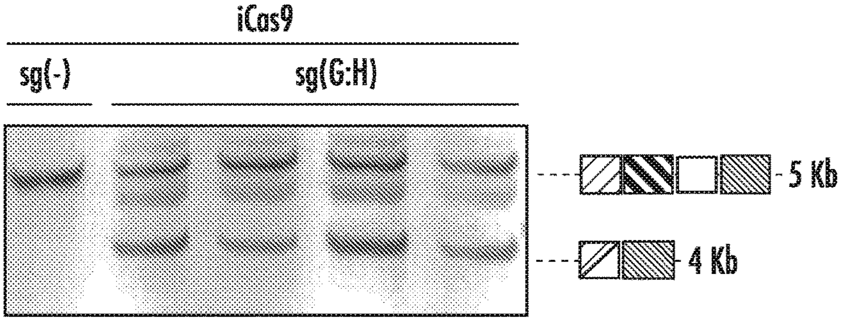

FIG. 2E

```
         PAM   ysg(G) TARGET            CORE            ysg(H) TARGET      PAM
EXPECT: CATCCCCCAGGCTTGCACTCGTACGTTCGAAATATTATAAATTATCAGACAGACCATACTCCAGATGGGGGATG
 SEQ-1: CATCCCCCAGGCTTGCACTCGTACGTTCGAAATATTATAAATTATCAGACAGACCATACTCCAGATGGGGGATG
 SEQ-2: CATCCCCCAGGCTTGCACTCGTACGTTCGAAATATTATAAATTATCAGACAGACCATACTCCAGATGGGGGATG
 SEQ-3: CATCCCCCAGGCTTGCACTCGTACGTTCGAAATATTATAAATTATCAGACAGACCATACTCCAGATGGGGGATG
 SEQ-4: CATCCCCCAGGCTTGCACTCGTACGTTCGAAATATTATAAATTATCAGACAGACCATACTCCAGATGGGGGATG
 SEQ-5: CATCCCCCAGGCTTGCACTCGTACGTTCGAAATATTATAAATTATCAGACAGACCATACTCCAGATGGGGGATG
```

FIG. 2F

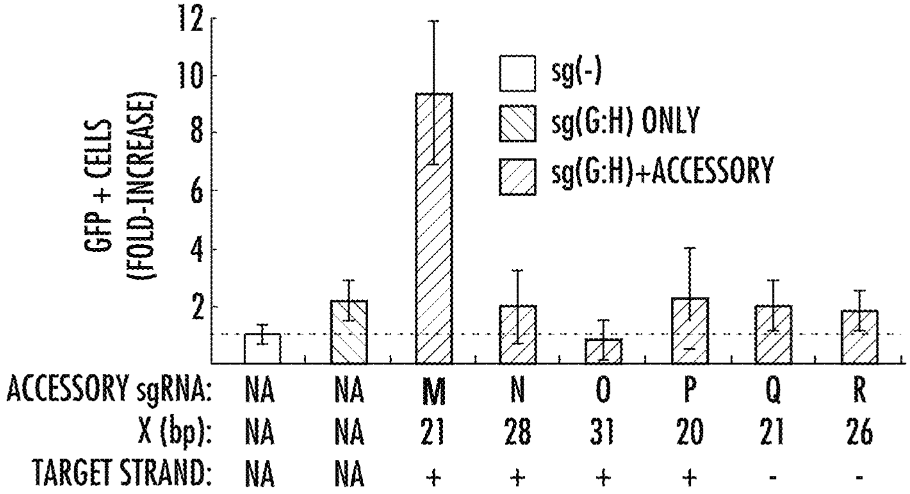

FIG. 5C

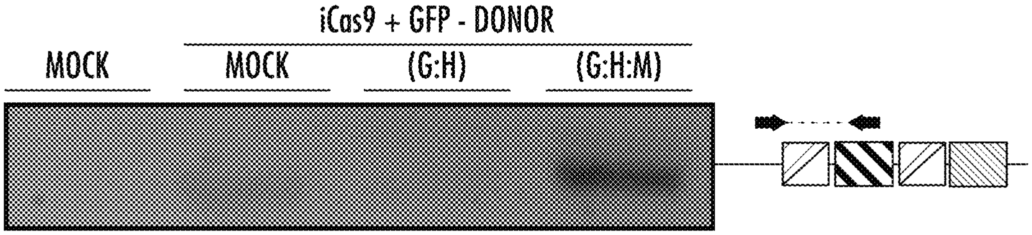

FIG. 5D

```
iCas9
PAM     hsg(G) TARGET          CORE          hsg(H) TARGET     PAM
EXPECT: CTTCCCCCAGGCTTGCACTCGTACGTTCGAAATATTATAAATTATCAGACAGACCTTACTCCAGAAGGGGGAAG
 SEQ-1: CTTCCCCCAGGCTTGCACTCGTACGTTCGAAATATTATAAATTATCAGACAGACCTTACTCCAGAAGGGGGAAG
 SEQ-2: CTTCCCCCAGGCTTGCACTCGTACGTTCGAAATATTATAAATTATCAGACAGACCTTACTCCAGAAGGGGGAAG
 SEQ-3: CTTCCCCCAGGCTTGCACTCGTACGTTCGAAATATTATAAATTATCAGACAGACCTTACTCCAGAAGGGGGAAG
 SEQ-4: CTTCCCCCAGGCTTGCACTCGTACGTTCGAAATATTATAAATTATCAGACAGACCTTACTCCAGAAGGGGGAAG
 SEQ-5: CTTCCCCCAGGCTTGCACTCGTACGTTCGAAATATTATAAATTATCAGACAGACCTTACTCCAGAAGGGGGAAG
```

FIG. 5E

```
Cas9^WT
PAM     hsg(G) TARGET
EXPECT: CTTCCCCCAGGCTTGCACTCGTACGTTCGAAATATTATAAATTATCAGACAGACCTTACTCCAGAAGGGGGAAG
 SEQ-1: CTTCCCCCAGGCTTGCACTCGTACGTTCGAAATATTATAAATTATCAGACAGACCTTACTCCAGAAGGGGGAAG
 SEQ-2: CTTCCCCCAGGCTTGCACTCGTACGTTCGAAATATTATAAATTATCAGACAGACCTTACTCCAGAAGGGGGAAG
 SEQ-3: CTTCCCCCAGGCTTGCACTCGTACGTTCGAAATATTATAAATTATCAGACAGACCTTACTCCAGAAGGGGGAAG
 SEQ-4: CTTCCCCCAG-------------------------------------------------------AGGGGGAAG
 SEQ-5: CTTCCCCCA-------------------------------------------------------AAGGGGGAAG
```

FIG. 5F

SEQUENCE LISTING

<160> NUMBER OF SEQ ID NOS: 121

<210> SEQ ID NO 1
<211> LENGTH: 1556
<212> TYPE: PRT
<213> ORGANISM: Artificial Sequence
<220> FEATURE:
<223> OTHER INFORMATION: fusion protein

<400> SEQUENCE: 1

```
Met Pro Lys Lys Lys Arg Lys Val Gly Gly Ser Met Arg Ile Phe Gly
1               5                   10                  15

Tyr Ala Arg Val Ser Thr Ser Gln Gln Ser Leu Asp Ile Gln Ile Arg
            20                  25                  30

Ala Leu Lys Asp Ala Gly Val Lys Ala Asn Arg Ile Phe Thr Asp Lys
        35                  40                  45

Ala Ser Gly Ser Ser Thr Asp Arg Glu Gly Leu Asp Leu Leu Arg Met
    50                  55                  60

Lys Val Glu Glu Gly Asp Val Ile Leu Val Lys Lys Leu Asp Arg Leu
65                  70                  75                  80

Ser Arg Asp Thr Ala Asp Met Ile Gln Leu Ile Lys Glu Phe Asp Ala
                85                  90                  95

Gln Gly Val Ala Val Arg Phe Ile Asp Asp Gly Ile Ser Thr Asp Gly
            100                 105                 110

Tyr Met Gly Gln Met Val Val Thr Ile Leu Ser Ala Val Ala Gln Ala
        115                 120                 125

Glu Arg Arg Arg Ile Leu Gln Arg Thr Asn Glu Gly Arg Gln Glu Ala
    130                 135                 140

Lys Leu Lys Gly Ile Lys Phe Gly Arg Arg Arg Thr Val Asp Arg Gly
145                 150                 155                 160

Gly Ser Gly Gly Ser Gly Gly Ser Gly Gly Ser Gly Gly Ser Gly Gly
                165                 170                 175

Ser Met Asp Lys Lys Tyr Ser Ile Gly Leu Ala Ile Gly Thr Asn Ser
            180                 185                 190

Val Gly Trp Ala Val Ile Thr Asp Glu Tyr Lys Val Pro Ser Lys Lys
        195                 200                 205

Phe Lys Val Leu Gly Asn Thr Asp Arg His Ser Ile Lys Lys Asn Leu
    210                 215                 220

Ile Gly Ala Leu Leu Phe Asp Ser Gly Glu Thr Ala Glu Ala Thr Arg
225                 230                 235                 240

Leu Lys Arg Thr Ala Arg Arg Arg Tyr Thr Arg Arg Lys Asn Arg Ile
                245                 250                 255

Cys Tyr Leu Gln Glu Ile Phe Ser Asn Glu Met Ala Lys Val Asp Asp
```

```
            260                 265                 270

Ser Phe Phe His Arg Leu Glu Glu Ser Phe Leu Val Glu Glu Asp Lys
        275                 280                 285

Lys His Glu Arg His Pro Ile Phe Gly Asn Ile Val Asp Glu Val Ala
    290                 295                 300

Tyr His Glu Lys Tyr Pro Thr Ile Tyr His Leu Arg Lys Lys Leu Val
305                 310                 315                 320

Asp Ser Thr Asp Lys Ala Asp Leu Arg Leu Ile Tyr Leu Ala Leu Ala
                325                 330                 335

His Met Ile Lys Phe Arg Gly His Phe Leu Ile Glu Gly Asp Leu Asn
            340                 345                 350

Pro Asp Asn Ser Asp Val Asp Lys Leu Phe Ile Gln Leu Val Gln Thr
        355                 360                 365

Tyr Asn Gln Leu Phe Glu Glu Asn Pro Ile Asn Ala Ser Gly Val Asp
    370                 375                 380

Ala Lys Ala Ile Leu Ser Ala Arg Leu Ser Lys Ser Arg Arg Leu Glu
385                 390                 395                 400

Asn Leu Ile Ala Gln Leu Pro Gly Glu Lys Lys Asn Gly Leu Phe Gly
                405                 410                 415

Asn Leu Ile Ala Leu Ser Leu Gly Leu Thr Pro Asn Phe Lys Ser Asn
            420                 425                 430

Phe Asp Leu Ala Glu Asp Ala Lys Leu Gln Leu Ser Lys Asp Thr Tyr
        435                 440                 445

Asp Asp Asp Leu Asp Asn Leu Leu Ala Gln Ile Gly Asp Gln Tyr Ala
    450                 455                 460

Asp Leu Phe Leu Ala Ala Lys Asn Leu Ser Asp Ala Ile Leu Leu Ser
465                 470                 475                 480

Asp Ile Leu Arg Val Asn Thr Glu Ile Thr Lys Ala Pro Leu Ser Ala
                485                 490                 495

Ser Met Ile Lys Arg Tyr Asp Glu His His Gln Asp Leu Thr Leu Leu
            500                 505                 510

Lys Ala Leu Val Arg Gln Gln Leu Pro Glu Lys Tyr Lys Glu Ile Phe
        515                 520                 525

Phe Asp Gln Ser Lys Asn Gly Tyr Ala Gly Tyr Ile Asp Gly Gly Ala
    530                 535                 540

Ser Gln Glu Glu Phe Tyr Lys Phe Ile Lys Pro Ile Leu Glu Lys Met
545                 550                 555                 560

Asp Gly Thr Glu Glu Leu Leu Val Lys Leu Asn Arg Glu Asp Leu Leu
                565                 570                 575

Arg Lys Gln Arg Thr Phe Asp Asn Gly Ser Ile Pro His Gln Ile His
            580                 585                 590

Leu Gly Glu Leu His Ala Ile Leu Arg Arg Gln Glu Asp Phe Tyr Pro
        595                 600                 605

Phe Leu Lys Asp Asn Arg Glu Lys Ile Glu Lys Ile Leu Thr Phe Arg
    610                 615                 620

Ile Pro Tyr Tyr Val Gly Pro Leu Ala Arg Gly Asn Ser Arg Phe Ala
625                 630                 635                 640

Trp Met Thr Arg Lys Ser Glu Glu Thr Ile Thr Pro Trp Asn Phe Glu
                645                 650                 655

Glu Val Val Asp Lys Gly Ala Ser Ala Gln Ser Phe Ile Glu Arg Met
            660                 665                 670

Thr Asn Phe Asp Lys Asn Leu Pro Asn Glu Lys Val Leu Pro Lys His
        675                 680                 685
```

```
Ser Leu Leu Tyr Glu Tyr Phe Thr Val Tyr Asn Glu Leu Thr Lys Val
    690                 695                 700

Lys Tyr Val Thr Glu Gly Met Arg Lys Pro Ala Phe Leu Ser Gly Glu
705                 710                 715                 720

Gln Lys Lys Ala Ile Val Asp Leu Leu Phe Lys Thr Asn Arg Lys Val
                725                 730                 735

Thr Val Lys Gln Leu Lys Glu Asp Tyr Phe Lys Lys Ile Glu Cys Phe
            740                 745                 750

Asp Ser Val Glu Ile Ser Gly Val Glu Asp Arg Phe Asn Ala Ser Leu
        755                 760                 765

Gly Thr Tyr His Asp Leu Leu Lys Ile Ile Lys Asp Lys Asp Phe Leu
    770                 775                 780

Asp Asn Glu Glu Asn Glu Asp Ile Leu Glu Asp Ile Val Leu Thr Leu
785                 790                 795                 800

Thr Leu Phe Glu Asp Arg Glu Met Ile Glu Glu Arg Leu Lys Thr Tyr
                805                 810                 815

Ala His Leu Phe Asp Asp Lys Val Met Lys Gln Leu Lys Arg Arg Arg
            820                 825                 830

Tyr Thr Gly Trp Gly Arg Leu Ser Arg Lys Leu Ile Asn Gly Ile Arg
        835                 840                 845

Asp Lys Gln Ser Gly Lys Thr Ile Leu Asp Phe Leu Lys Ser Asp Gly
    850                 855                 860

Phe Ala Asn Arg Asn Phe Met Gln Leu Ile His Asp Asp Ser Leu Thr
865                 870                 875                 880

Phe Lys Glu Asp Ile Gln Lys Ala Gln Val Ser Gly Gln Gly Asp Ser
                885                 890                 895

Leu His Glu His Ile Ala Asn Leu Ala Gly Ser Pro Ala Ile Lys Lys
            900                 905                 910

Gly Ile Leu Gln Thr Val Lys Val Val Asp Glu Leu Val Lys Val Met
        915                 920                 925

Gly Arg His Lys Pro Glu Asn Ile Val Ile Glu Met Ala Arg Glu Asn
    930                 935                 940

Gln Thr Thr Gln Lys Gly Gln Lys Asn Ser Arg Glu Arg Met Lys Arg
945                 950                 955                 960

Ile Glu Glu Gly Ile Lys Glu Leu Gly Ser Gln Ile Leu Lys Glu His
                965                 970                 975

Pro Val Glu Asn Thr Gln Leu Gln Asn Glu Lys Leu Tyr Leu Tyr Tyr
            980                 985                 990

Leu Gln Asn Gly Arg Asp Met Tyr  Val Asp Gln Glu Leu  Asp Ile Asn
        995                 1000                1005

Arg Leu  Ser Asp Tyr Asp Val  Asp Ala Ile Val Pro  Gln Ser Phe
    1010                1015                1020

Leu Lys  Asp Asp Ser Ile Asp  Asn Lys Val Leu Thr  Arg Ser Asp
    1025                1030                1035

Lys Asn  Arg Gly Lys Ser Asp  Asn Val Pro Ser Glu  Glu Val Val
    1040                1045                1050

Lys Lys  Met Lys Asn Tyr Trp  Arg Gln Leu Leu Asn  Ala Lys Leu
    1055                1060                1065

Ile Thr  Gln Arg Lys Phe Asp  Asn Leu Thr Lys Ala  Glu Arg Gly
    1070                1075                1080

Gly Leu  Ser Glu Leu Asp Lys  Ala Gly Phe Ile Lys  Arg Gln Leu
    1085                1090                1095
```

```
Val Glu  Thr Arg Gln Ile Thr  Lys His Val Ala Gln  Ile Leu Asp
    1100                 1105                 1110

Ser Arg  Met Asn Thr Lys Tyr  Asp Glu Asn Asp Lys  Leu Ile Arg
    1115                 1120                 1125

Glu Val  Lys Val Ile Thr Leu  Lys Ser Lys Leu Val  Ser Asp Phe
    1130                 1135                 1140

Arg Lys  Asp Phe Gln Phe Tyr  Lys Val Arg Glu Ile  Asn Asn Tyr
    1145                 1150                 1155

His His  Ala His Asp Ala Tyr  Leu Asn Ala Val Val  Gly Thr Ala
    1160                 1165                 1170

Leu Ile  Lys Lys Tyr Pro Lys  Leu Glu Ser Glu Phe  Val Tyr Gly
    1175                 1180                 1185

Asp Tyr  Lys Val Tyr Asp Val  Arg Lys Met Ile Ala  Lys Ser Glu
    1190                 1195                 1200

Gln Glu  Ile Gly Lys Ala Thr  Ala Lys Tyr Phe Phe  Tyr Ser Asn
    1205                 1210                 1215

Ile Met  Asn Phe Phe Lys Thr  Glu Ile Thr Leu Ala  Asn Gly Glu
    1220                 1225                 1230

Ile Arg  Lys Arg Pro Leu Ile  Glu Thr Asn Gly Glu  Thr Gly Glu
    1235                 1240                 1245

Ile Val  Trp Asp Lys Gly Arg  Asp Phe Ala Thr Val  Arg Lys Val
    1250                 1255                 1260

Leu Ser  Met Pro Gln Val Asn  Ile Val Lys Lys Thr  Glu Val Gln
    1265                 1270                 1275

Thr Gly  Gly Phe Ser Lys Glu  Ser Ile Leu Pro Lys  Arg Asn Ser
    1280                 1285                 1290

Asp Lys  Leu Ile Ala Arg Lys  Lys Asp Trp Asp Pro  Lys Lys Tyr
    1295                 1300                 1305

Gly Gly  Phe Asp Ser Pro Thr  Val Ala Tyr Ser Val  Leu Val Val
    1310                 1315                 1320

Ala Lys  Val Glu Lys Gly Lys  Ser Lys Lys Leu Lys  Ser Val Lys
    1325                 1330                 1335

Glu Leu  Leu Gly Ile Thr Ile  Met Glu Arg Ser Ser  Phe Glu Lys
    1340                 1345                 1350

Asn Pro  Ile Asp Phe Leu Glu  Ala Lys Gly Tyr Lys  Glu Val Lys
    1355                 1360                 1365

Lys Asp  Leu Ile Ile Lys Leu  Pro Lys Tyr Ser Leu  Phe Glu Leu
    1370                 1375                 1380

Glu Asn  Gly Arg Lys Arg Met  Leu Ala Ser Ala Gly  Glu Leu Gln
    1385                 1390                 1395

Lys Gly  Asn Glu Leu Ala Leu  Pro Ser Lys Tyr Val  Asn Phe Leu
    1400                 1405                 1410

Tyr Leu  Ala Ser His Tyr Glu  Lys Leu Lys Gly Ser  Pro Glu Asp
    1415                 1420                 1425

Asn Glu  Gln Lys Gln Leu Phe  Val Glu Gln His Lys  His Tyr Leu
    1430                 1435                 1440

Asp Glu  Ile Ile Glu Gln Ile  Ser Glu Phe Ser Lys  Arg Val Ile
    1445                 1450                 1455

Leu Ala  Asp Ala Asn Leu Asp  Lys Val Leu Ser Ala  Tyr Asn Lys
    1460                 1465                 1470

His Arg  Asp Lys Pro Ile Arg  Glu Gln Ala Glu Asn  Ile Ile His
    1475                 1480                 1485

Leu Phe  Thr Leu Thr Asn Leu  Gly Ala Pro Ala Ala  Phe Lys Tyr
```

```
    1490                1495                1500

Phe Asp  Thr Thr Ile Asp Arg  Lys Arg Tyr Thr Ser  Thr Lys Glu
    1505                1510                1515

Val Leu  Asp Ala Thr Leu Ile  His Gln Ser Ile Thr  Gly Leu Tyr
    1520                1525                1530

Glu Thr  Arg Ile Asp Leu Ser  Gln Leu Gly Gly Asp  Ser Arg Ala
    1535                1540                1545

Asp Pro  Lys Lys Lys Arg Lys  Val
    1550                1555
```

<210> SEQ ID NO 2
<211> LENGTH: 4671
<212> TYPE: DNA
<213> ORGANISM: Artificial Sequence
<220> FEATURE:
<223> OTHER INFORMATION: nucleotide sequence encoding the fusion protein of SEQ ID NO. 1

<400> SEQUENCE: 2

```
atgcccaaaa agaagaggaa agtaggtggc agtatgagga tatttggata cgcacgagtt     60

agtacatctc aacagtctct ggacatacag ataagggcat tgaaggatgc tggagtgaaa    120

gctaatcgga tctttaccga taaggctagt ggcagctcta cagacagaga gggcttggat    180

ctgctgagaa tgaaggttga ggaaggggat gtgatactcg tcaagaaact tgacagactc    240

tcacgagaca ctgccgatat gatccaactg attaaggaat ttgacgccca aggtgtagcc    300

gtaagattta ttgatgacgg tatcagcacc gacggctata tgggccagat ggtcgtcact    360

atactgagcg ctgtcgcaca agcggagaga agacgaatcc tgcaacggac aaatgaaggt    420

cgccaagaag caaagctcaa aggaattaag ttcgggcgca ggaggactgt agacagaggt    480

ggttcaggag gaagtggagg ttcaggggga agtggtggct ccggtgggtc tatggacaag    540

aagtactcca ttgggctcgc catcggcaca aacagcgtcg gttgggccgt cattacggac    600

gagtacaagg tgccgagcaa aaaattcaaa gttctgggca ataccgatcg ccacagcata    660

aagaagaacc tcattggcgc cctcctgttc gactccgggg agacggccga agccacgcgg    720

ctcaaaagaa cagcacggcg cagatatacc cgcagaaaga atcggatctg ctacctgcag    780

gagatcttta gtaatgagat ggctaaggtg gatgactctt tcttccatag gctggaggag    840

tcctttttgg tggaggagga taaaaagcac gagcgccacc caatctttgg caatatcgtg    900

gacgaggtgg cgtaccatga aaagtaccca accatatatc atctgaggaa gaagcttgta    960

gacagtactg ataaggctga cttgcggttg atctatctcg cgctggcgca tatgatcaaa   1020

tttcggggac acttcctcat cgagggggac ctgaacccag acaacagcga tgtcgacaaa   1080

ctctttatcc aactggttca gacttacaat cagcttttcg aagagaaccc gatcaacgca   1140

tccggagttg acgccaaagc aatcctgagc gctaggctgt ccaaatcccg gcggctcgaa   1200

aacctcatcg cacagctccc tggggagaag aagaacggcc tgtttggtaa tcttatcgcc   1260

ctgtcactcg ggctgacccc caactttaaa tctaacttcg acctggccga agatgccaag   1320

cttcaactga gcaaagacac ctacgatgat gatctcgaca atctgctggc ccagatcggc   1380

gaccagtacg cagacctttt tttggcggca aagaacctgt cagacgccat tctgctgagt   1440

gatattctgc gagtgaacac ggagatcacc aaagctccgc tgagcgctag tatgatcaag   1500

cgctatgatg agcaccacca agacttgact ttgctgaagg cccttgtcag acagcaactg   1560

cctgagaagt acaaggaaat tttcttcgat cagtctaaaa atggctacgc cggatacatt   1620
```

```
gacggcggag caagccagga ggaattttac aaatttatta agcccatctt ggaaaaaatg   1680
gacggcaccg aggagctgct ggtaaagctt aacagagaag atctgttgcg caaacagcgc   1740
actttcgaca atggaagcat cccccaccag attcacctgg gcgaactgca cgctatcctc   1800
aggcggcaag aggatttcta ccccttttttg aaagataaca gggaaaagat tgagaaaatc   1860
ctcacatttc ggataccccta ctatgtaggc ccctcgccc ggggaaattc cagattcgcg   1920
tggatgactc gcaaatcaga agagaccatc actccctgga acttcgagga agtcgtggat   1980
aagggggcct ctgcccagtc cttcatcgaa aggatgacta actttgataa aaatctgcct   2040
aacgaaaagg tgcttcctaa acactctctg ctgtacgagt acttcacagt ttataacgag   2100
ctcaccaagg tcaaatacgt cacagaaggg atgagaaagc cagcattcct gtctggagag   2160
cagaagaaag ctatcgtgga cctcctcttc aagacgaacc ggaaagttac cgtgaaacag   2220
ctcaaagaag actatttcaa aaagattgaa tgtttcgact ctgttgaaat cagcggagtg   2280
gaggatcgct tcaacgcatc cctgggaacg tatcacgatc tcctgaaaat cattaaagac   2340
aaggacttcc tggacaatga ggagaacgag gacattcttg aggacattgt cctcaccctt   2400
acgttgtttg aagataggga gatgattgaa gaacgcttga aaacttacgc tcatctcttc   2460
gacgacaaag tcatgaaaca gctcaagagg cgccgatata caggatgggg gcggctgtca   2520
agaaaactga tcaatgggat ccgagacaag cagagtggaa agacaatcct ggattttctt   2580
aagtccgatg gatttgccaa ccggaacttc atgcagttga tccatgatga ctctctcacc   2640
tttaaggagg acatccagaa agcacaagtt tctggccagg gggacagtct tcacgagcac   2700
atcgctaatc ttgcaggtag cccagctatc aaaaagggaa tactgcagac cgttaaggtc   2760
gtggatgaac tcgtcaaagt aatgggaagg cataagcccg agaatatcgt tatcgagatg   2820
gcccgagaga accaaactac ccagaaggga cagaagaaca gtagggaaag gatgaagagg   2880
attgaagagg gtataaaaga actggggtcc caaatcctta aggaacaccc agttgaaaac   2940
acccagcttc agaatgagaa gctctacctg tactacctgc agaacggcag ggacatgtac   3000
gtggatcagg aactggacat caatcggctc tccgactacg acgtggatgc catcgtgccc   3060
cagtcttttc tcaaagatga ttctattgat aataaagtgt tgacaagatc cgataaaaat   3120
agagggaaga gtgataacgt cccctcagaa gaagttgtca agaaaatgaa aaattattgg   3180
cggcagctgc tgaacgccaa actgatcaca caacggaagt tcgataatct gactaaggct   3240
gaacgaggtg gcctgtctga gttggataaa gccggcttca tcaaaaggca gcttgttgag   3300
acacgccaga tcaccaagca cgtggcccaa attctcgatt cacgcatgaa caccaagtac   3360
gatgaaaatg acaaactgat tcgagaggtg aaagttatta ctctgaagtc taagctggtc   3420
tcagatttca gaaaggactt tcagttttat aaggtgagag agatcaacaa ttaccaccat   3480
gcgcatgatg cctacctgaa tgcagtggta ggcactgcac ttatcaaaaa atatcccaag   3540
cttgaatctg aatttgttta cggagactat aaagtgtacg atgttaggaa aatgatcgca   3600
aagtctgagc aggaaatagg caaggccacc gctaagtact tcttttacag caatattatg   3660
aattttttca agaccgagat tacactggcc aatggagaga ttcggaagcg accacttatc   3720
gaaacaaacg gagaaacagg agaaatcgtg tgggacaagg gtagggattt cgcgacagtc   3780
cggaaggtcc tgtccatgcc gcaggtgaac atcgttaaaa agaccgaagt acagaccgga   3840
ggcttctcca aggaaagtat cctcccgaaa aggaacagcg acaagctgat cgcacgcaaa   3900
aaagattggg accccaagaa atacggcgga ttcgattctc ctacagtcgc ttacagtgta   3960
ctggttgtgg ccaaagtgga gaaagggaag tctaaaaaac tcaaaagcgt caaggaactg   4020
```

ctgggcatca caatcatgga gcgatcaagc ttcgaaaaaa accccatcga ctttctcgag 4080
gcgaaaggat ataaagaggt caaaaaagac ctcatcatta agcttcccaa gtactctctc 4140
tttgagcttg aaaacggccg gaaacgaatg ctcgctagtg cgggcgagct gcagaaaggt 4200
aacgagctgg cactgccctc taaatacgtt aatttcttgt atctggccag ccactatgaa 4260
aagctcaaag ggtctcccga agataatgag cagaagcagc tgttcgtgga acaacacaaa 4320
cactaccttg atgagatcat cgagcaaata agcgaattct ccaaaagagt gatcctcgcc 4380
gacgctaacc tcgataaggt gctttctgct tacaataagc acagggataa gcccatcagg 4440
gagcaggcag aaaacattat ccacttgttt actctgacca acttgggcgc gcctgcagcc 4500
ttcaagtact tcgacaccac catagacaga aagcggtaca cctctacaaa ggaggtcctg 4560
gacgccacac tgattcatca gtcaattacg gggctctatg aaacaagaat cgacctctct 4620
cagctcggtg gagacagcag ggctgacccc aagaagaaga ggaaggtgtg a 4671

<210> SEQ ID NO 3
<211> LENGTH: 18
<212> TYPE: DNA
<213> ORGANISM: Artificial Sequence
<220> FEATURE:
<223> OTHER INFORMATION: sgRNA guide sequence

<400> SEQUENCE: 3
agaagagcga gctcttct 18

<210> SEQ ID NO 4
<211> LENGTH: 20
<212> TYPE: DNA
<213> ORGANISM: Artificial Sequence
<220> FEATURE:
<223> OTHER INFORMATION: sgRNA guide sequence

<400> SEQUENCE: 4
cgaacgtacg agtgcaagcc 20

<210> SEQ ID NO 5
<211> LENGTH: 20
<212> TYPE: DNA
<213> ORGANISM: Artificial Sequence
<220> FEATURE:
<223> OTHER INFORMATION: sgRNA guide sequence

<400> SEQUENCE: 5
gaacgtacga gtgcaagcct 20

<210> SEQ ID NO 6
<211> LENGTH: 20
<212> TYPE: DNA
<213> ORGANISM: Artificial Sequence
<220> FEATURE:
<223> OTHER INFORMATION: sgRNA guide sequence

<400> SEQUENCE: 6
aacgtacgag tgcaagcctg 20

<210> SEQ ID NO 7
<211> LENGTH: 20
<212> TYPE: DNA
<213> ORGANISM: Artificial Sequence
<220> FEATURE:
<223> OTHER INFORMATION: sgRNA guide sequence

<400> SEQUENCE: 7
acgtacgagt gcaagcctgg 20

<210> SEQ ID NO 8
<211> LENGTH: 20
<212> TYPE: DNA
<213> ORGANISM: Artificial Sequence
<220> FEATURE:
<223> OTHER INFORMATION: sgRNA guide sequence

<400> SEQUENCE: 8
acgagtgcaa gcctggggga 20

<210> SEQ ID NO 9
<211> LENGTH: 20
<212> TYPE: DNA
<213> ORGANISM: Artificial Sequence
<220> FEATURE:
<223> OTHER INFORMATION: sgRNA guide sequence

<400> SEQUENCE: 9
tgcaagcctg ggggatggat 20

<210> SEQ ID NO 10
<211> LENGTH: 20
<212> TYPE: DNA
<213> ORGANISM: Artificial Sequence
<220> FEATURE:
<223> OTHER INFORMATION: sgRNA guide sequence

<400> SEQUENCE: 10
cagacagacc atactccaga 20

<210> SEQ ID NO 11
<211> LENGTH: 20
<212> TYPE: DNA
<213> ORGANISM: Artificial Sequence
<220> FEATURE:
<223> OTHER INFORMATION: sgRNA guide sequence

<400> SEQUENCE: 11
agacagacca tactccagat 20

<210> SEQ ID NO 12
<211> LENGTH: 20
<212> TYPE: DNA
<213> ORGANISM: Artificial Sequence
<220> FEATURE:
<223> OTHER INFORMATION: sgRNA guide sequence

<400> SEQUENCE: 12
gacagaccat actccagatg 20

<210> SEQ ID NO 13
<211> LENGTH: 20
<212> TYPE: DNA
<213> ORGANISM: Artificial Sequence
<220> FEATURE:
<223> OTHER INFORMATION: sgRNA guide sequence

<400> SEQUENCE: 13
acagaccata ctccagatgg 20

<210> SEQ ID NO 14
<211> LENGTH: 20

<212> TYPE: DNA
<213> ORGANISM: Artificial Sequence
<220> FEATURE:
<223> OTHER INFORMATION: sgRNA guide sequence

<400> SEQUENCE: 14
accatactcc agatggggga 20

<210> SEQ ID NO 15
<211> LENGTH: 20
<212> TYPE: DNA
<213> ORGANISM: Artificial Sequence
<220> FEATURE:
<223> OTHER INFORMATION: sgRNA guide sequence

<400> SEQUENCE: 15
actccagatg ggggatggct 20

<210> SEQ ID NO 16
<211> LENGTH: 18
<212> TYPE: DNA
<213> ORGANISM: Artificial Sequence
<220> FEATURE:
<223> OTHER INFORMATION: sgRNA guide sequence

<400> SEQUENCE: 16
gggtcttcga gaagacct 18

<210> SEQ ID NO 17
<211> LENGTH: 21
<212> TYPE: DNA
<213> ORGANISM: Artificial Sequence
<220> FEATURE:
<223> OTHER INFORMATION: sgRNA guide sequence

<400> SEQUENCE: 17
gacgtacgag tgcaagcctg g 21

<210> SEQ ID NO 18
<211> LENGTH: 21
<212> TYPE: DNA
<213> ORGANISM: Artificial Sequence
<220> FEATURE:
<223> OTHER INFORMATION: sgRNA guide sequence

<400> SEQUENCE: 18
gacagacctt actccagaag g 21

<210> SEQ ID NO 19
<211> LENGTH: 21
<212> TYPE: DNA
<213> ORGANISM: Artificial Sequence
<220> FEATURE:
<223> OTHER INFORMATION: sgRNA guide sequence

<400> SEQUENCE: 19
gtgcaagcct gggggaagga t 21

<210> SEQ ID NO 20
<211> LENGTH: 21
<212> TYPE: DNA
<213> ORGANISM: Artificial Sequence
<220> FEATURE:
<223> OTHER INFORMATION: sgRNA guide sequence

<400> SEQUENCE: 20
gactccagaa gggggaaggc t 21

<210> SEQ ID NO 21
<211> LENGTH: 21
<212> TYPE: DNA
<213> ORGANISM: Artificial Sequence
<220> FEATURE:
<223> OTHER INFORMATION: sgRNA guide sequence

<400> SEQUENCE: 21
gacgagtgca agcctggggg a 21

<210> SEQ ID NO 22
<211> LENGTH: 21
<212> TYPE: DNA
<213> ORGANISM: Artificial Sequence
<220> FEATURE:
<223> OTHER INFORMATION: sgRNA guide sequence

<400> SEQUENCE: 22
gaccttactc cagaaggggg a 21

<210> SEQ ID NO 23
<211> LENGTH: 21
<212> TYPE: DNA
<213> ORGANISM: Artificial Sequence
<220> FEATURE:
<223> OTHER INFORMATION: sgRNA guide sequence

<400> SEQUENCE: 23
gttgctcacc atggtggcga c 21

<210> SEQ ID NO 24
<211> LENGTH: 21
<212> TYPE: DNA
<213> ORGANISM: Artificial Sequence
<220> FEATURE:
<223> OTHER INFORMATION: primer

<400> SEQUENCE: 24
gctcgccctt gctcaccatg g 21

<210> SEQ ID NO 25
<211> LENGTH: 21
<212> TYPE: DNA
<213> ORGANISM: Artificial Sequence
<220> FEATURE:
<223> OTHER INFORMATION: sgRNA guide sequence

<400> SEQUENCE: 25
gctcctcgcc cttgctcacc a 21

<210> SEQ ID NO 26
<211> LENGTH: 20
<212> TYPE: DNA
<213> ORGANISM: Artificial Sequence
<220> FEATURE:
<223> OTHER INFORMATION: sgRNA guide sequence

<400> SEQUENCE: 26
ggtcgccacc atggtgagca 20

<210> SEQ ID NO 27
<211> LENGTH: 20
<212> TYPE: DNA
<213> ORGANISM: Artificial Sequence
<220> FEATURE:
<223> OTHER INFORMATION: sgRNA guide sequence

<400> SEQUENCE: 27
gtcgccacca tggtgagcaa 20

<210> SEQ ID NO 28
<211> LENGTH: 21
<212> TYPE: DNA
<213> ORGANISM: Artificial Sequence
<220> FEATURE:
<223> OTHER INFORMATION: sgRNA guide sequence

<400> SEQUENCE: 28
gcaccatggt gagcaagggc g 21

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
cgcatatgtg gtgttgaaga 20

<210> SEQ ID NO 30
<211> LENGTH: 22
<212> TYPE: DNA
<213> ORGANISM: Artificial Sequence
<220> FEATURE:
<223> OTHER INFORMATION: primer

<400> SEQUENCE: 30
ctagggcttt ctgctctgtc at 22

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
tggagggcac agttaagccg 20

<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
aataccgcct ttgagtgagc 20

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
agctgtgacc ggcgcctacg 20

<210> SEQ ID NO 34
<211> LENGTH: 23
<212> TYPE: DNA
<213> ORGANISM: Artificial Sequence
<220> FEATURE:
<223> OTHER INFORMATION: primer

<400> SEQUENCE: 34
ctgagcaccc agtccgccct gag 23

<210> SEQ ID NO 35
<211> LENGTH: 47
<212> TYPE: DNA
<213> ORGANISM: Artificial Sequence
<220> FEATURE:
<223> OTHER INFORMATION: primer

<400> SEQUENCE: 35
aattctccga tccatccccc aggcttgcac tcgtacgttc gaaatat 47

<210> SEQ ID NO 36
<211> LENGTH: 46
<212> TYPE: DNA
<213> ORGANISM: Artificial Sequence
<220> FEATURE:
<223> OTHER INFORMATION: primer

<400> SEQUENCE: 36
ataatatttc gaacgtacga gtgcaagcct gggggatgga tcggag 46

<210> SEQ ID NO 37
<211> LENGTH: 47
<212> TYPE: DNA
<213> ORGANISM: Artificial Sequence
<220> FEATURE:
<223> OTHER INFORMATION: primer

<400> SEQUENCE: 37
tataaattat cagacagacc atactccaga tgggggatgg ctaggtg 47

<210> SEQ ID NO 38
<211> LENGTH: 48
<212> TYPE: DNA
<213> ORGANISM: Artificial Sequence
<220> FEATURE:
<223> OTHER INFORMATION: primer

<400> SEQUENCE: 38
aattcaccta gccatccccc atctggagta tggtctgtct gataattt 48

<210> SEQ ID NO 39
<211> LENGTH: 47
<212> TYPE: DNA
<213> ORGANISM: Artificial Sequence
<220> FEATURE:
<223> OTHER INFORMATION: primer

<400> SEQUENCE: 39
cgcgttccga tccatccccc aggcttgcac tcgtacgttc gaaatat 47

<210> SEQ ID NO 40
<211> LENGTH: 46
<212> TYPE: DNA
<213> ORGANISM: Artificial Sequence
<220> FEATURE:
<223> OTHER INFORMATION: primer

<400> SEQUENCE: 40
ataatatttc gaacgtacga gtgcaagcct gggggatgga tcggaa 46

<210> SEQ ID NO 41
<211> LENGTH: 47
<212> TYPE: DNA
<213> ORGANISM: Artificial Sequence
<220> FEATURE:
<223> OTHER INFORMATION: primer

<400> SEQUENCE: 41
tataaattat cagacagacc atactccaga tgggggatgg ctaggta 47

<210> SEQ ID NO 42
<211> LENGTH: 48
<212> TYPE: DNA
<213> ORGANISM: Artificial Sequence
<220> FEATURE:
<223> OTHER INFORMATION: primer

<400> SEQUENCE: 42
cgcgtaccta gccatccccc atctggagta tggtctgtct gataattt 48

<210> SEQ ID NO 43
<211> LENGTH: 47
<212> TYPE: DNA
<213> ORGANISM: Artificial Sequence
<220> FEATURE:
<223> OTHER INFORMATION: primer

<400> SEQUENCE: 43
aattctccga tccttccccc aggcttgcac tcgtacgttc gaaatat 47

<210> SEQ ID NO 44
<211> LENGTH: 43
<212> TYPE: DNA
<213> ORGANISM: Artificial Sequence
<220> FEATURE:
<223> OTHER INFORMATION: primer

<400> SEQUENCE: 44
ctccgatcct tcccccaggc ttgcactcgt acgttcgaaa tat 43

<210> SEQ ID NO 45
<211> LENGTH: 46
<212> TYPE: DNA
<213> ORGANISM: Artificial Sequence
<220> FEATURE:
<223> OTHER INFORMATION: primer

<400> SEQUENCE: 45
ataatatttc gaacgtacga gtgcaagcct gggggaagga tcggag 46

<210> SEQ ID NO 46
<211> LENGTH: 47
<212> TYPE: DNA
<213> ORGANISM: Artificial Sequence
<220> FEATURE:
<223> OTHER INFORMATION: primer

<400> SEQUENCE: 46
tataaattat cagacagacc ttactccaga agggggaagg ctaggtg 47

<210> SEQ ID NO 47

<211> LENGTH: 48
<212> TYPE: DNA
<213> ORGANISM: Artificial Sequence
<220> FEATURE:
<223> OTHER INFORMATION: primer

<400> SEQUENCE: 47
gatccaccta gccttccccc ttctggagta aggtctgtct gataattt 48

<210> SEQ ID NO 48
<211> LENGTH: 44
<212> TYPE: DNA
<213> ORGANISM: Artificial Sequence
<220> FEATURE:
<223> OTHER INFORMATION: primer

<400> SEQUENCE: 48
cacctagcct tcccccttct ggagtaaggt ctgtctgata attt 44

<210> SEQ ID NO 49
<211> LENGTH: 42
<212> TYPE: DNA
<213> ORGANISM: Artificial Sequence
<220> FEATURE:
<223> OTHER INFORMATION: primer

<400> SEQUENCE: 49
agaacagttg atagaggagg gagcggggga agcggtggct ca 42

<210> SEQ ID NO 50
<211> LENGTH: 42
<212> TYPE: DNA
<213> ORGANISM: Artificial Sequence
<220> FEATURE:
<223> OTHER INFORMATION: primer

<400> SEQUENCE: 50
cattgagcca ccgcttcccc cgctccctcc tctatcaact gt 42

<210> SEQ ID NO 51
<211> LENGTH: 36
<212> TYPE: DNA
<213> ORGANISM: Artificial Sequence
<220> FEATURE:
<223> OTHER INFORMATION: primer

<400> SEQUENCE: 51
agaactgttg accgaggtgg ttcaggagga agtgga 36

<210> SEQ ID NO 52
<211> LENGTH: 36
<212> TYPE: DNA
<213> ORGANISM: Artificial Sequence
<220> FEATURE:
<223> OTHER INFORMATION: primer

<400> SEQUENCE: 52
acctccactt cctcctgaac cacctcggtc aacagt 36

<210> SEQ ID NO 53
<211> LENGTH: 33
<212> TYPE: DNA
<213> ORGANISM: Artificial Sequence
<220> FEATURE:
<223> OTHER INFORMATION: primer

<400> SEQUENCE: 53
ggttcagggg gaagtggtgg ctccggtggg tct 33

<210> SEQ ID NO 54
<211> LENGTH: 33
<212> TYPE: DNA
<213> ORGANISM: Artificial Sequence
<220> FEATURE:
<223> OTHER INFORMATION: primer

<400> SEQUENCE: 54
catagaccca ccggagccac cacttccccc tga 33

<210> SEQ ID NO 55
<211> LENGTH: 30
<212> TYPE: DNA
<213> ORGANISM: Artificial Sequence
<220> FEATURE:
<223> OTHER INFORMATION: primer

<400> SEQUENCE: 55
agaacagttg atcggagcgg ttctgagact 30

<210> SEQ ID NO 56
<211> LENGTH: 30
<212> TYPE: DNA
<213> ORGANISM: Artificial Sequence
<220> FEATURE:
<223> OTHER INFORMATION: primer

<400> SEQUENCE: 56
cggagtctca gaaccgctcc gatcaactgt 30

<210> SEQ ID NO 57
<211> LENGTH: 33
<212> TYPE: DNA
<213> ORGANISM: Artificial Sequence
<220> FEATURE:
<223> OTHER INFORMATION: primer

<400> SEQUENCE: 57
ccgggaacct cagagtctgc tacgccggaa agc 33

<210> SEQ ID NO 58
<211> LENGTH: 33
<212> TYPE: DNA
<213> ORGANISM: Artificial Sequence
<220> FEATURE:
<223> OTHER INFORMATION: primer

<400> SEQUENCE: 58
catgctttcc ggcgtagcag actctgaggt tcc 33

<210> SEQ ID NO 59
<211> LENGTH: 37
<212> TYPE: DNA
<213> ORGANISM: Artificial Sequence
<220> FEATURE:
<223> OTHER INFORMATION: primer

<400> SEQUENCE: 59
agaaccgtag atcgcggggg ctctggagga tcaggta 37

<210> SEQ ID NO 60
<211> LENGTH: 37
<212> TYPE: DNA

<213> ORGANISM: Artificial Sequence
<220> FEATURE:
<223> OTHER INFORMATION: primer

<400> SEQUENCE: 60
cgctacctga tcctccagag cccccgcgat ctacggt 37

<210> SEQ ID NO 61
<211> LENGTH: 41
<212> TYPE: DNA
<213> ORGANISM: Artificial Sequence
<220> FEATURE:
<223> OTHER INFORMATION: primer

<400> SEQUENCE: 61
gcgaaacgcc gggtactagc gaaagcgcga cacctgagag t 41

<210> SEQ ID NO 62
<211> LENGTH: 41
<212> TYPE: DNA
<213> ORGANISM: Artificial Sequence
<220> FEATURE:
<223> OTHER INFORMATION: primer

<400> SEQUENCE: 62
catactctca ggtgtcgcgc tttcgctagt acccggcgtt t 41

<210> SEQ ID NO 63
<211> LENGTH: 34
<212> TYPE: DNA
<213> ORGANISM: Artificial Sequence
<220> FEATURE:
<223> OTHER INFORMATION: primer

<400> SEQUENCE: 63
acggctcttc gatgcccaaa aagaagagga aagt 34

<210> SEQ ID NO 64
<211> LENGTH: 32
<212> TYPE: DNA
<213> ORGANISM: Artificial Sequence
<220> FEATURE:
<223> OTHER INFORMATION: primer

<400> SEQUENCE: 64
agcgctcttc atctgtctac agtcctcctg cg 32

<210> SEQ ID NO 65
<211> LENGTH: 32
<212> TYPE: DNA
<213> ORGANISM: Artificial Sequence
<220> FEATURE:
<223> OTHER INFORMATION: primer

<400> SEQUENCE: 65
acggctcttc gcattttttt cccgggggat cc 32

<210> SEQ ID NO 66
<211> LENGTH: 29
<212> TYPE: DNA
<213> ORGANISM: Artificial Sequence
<220> FEATURE:
<223> OTHER INFORMATION: primer

<400> SEQUENCE: 66
gcgctcttca gccatcggca caaacagcg 29

<210> SEQ ID NO 67
<211> LENGTH: 35
<212> TYPE: DNA
<213> ORGANISM: Artificial Sequence
<220> FEATURE:
<223> OTHER INFORMATION: primer

<400> SEQUENCE: 67
acggctcttc gggcgagccc aatggagtac ttctt 35

<210> SEQ ID NO 68
<211> LENGTH: 31
<212> TYPE: DNA
<213> ORGANISM: Artificial Sequence
<220> FEATURE:
<223> OTHER INFORMATION: primer

<400> SEQUENCE: 68
gcgctcttca gccatcgtgc cccagtcttt t 31

<210> SEQ ID NO 69
<211> LENGTH: 33
<212> TYPE: DNA
<213> ORGANISM: Artificial Sequence
<220> FEATURE:
<223> OTHER INFORMATION: primer

<400> SEQUENCE: 69
acggctcttc gggcatccac gtcgtagtcg gag 33

<210> SEQ ID NO 70
<211> LENGTH: 39
<212> TYPE: DNA
<213> ORGANISM: Artificial Sequence
<220> FEATURE:
<223> OTHER INFORMATION: primer

<400> SEQUENCE: 70
atacaccggt gccaccatgc ccaaaaagaa gaggaaagt 39

<210> SEQ ID NO 71
<211> LENGTH: 33
<212> TYPE: DNA
<213> ORGANISM: Artificial Sequence
<220> FEATURE:
<223> OTHER INFORMATION: primer

<400> SEQUENCE: 71
gatgacaatt gtcacacctt cctcttcttc ttg 33

<210> SEQ ID NO 72
<211> LENGTH: 38
<212> TYPE: DNA
<213> ORGANISM: Artificial Sequence
<220> FEATURE:
<223> OTHER INFORMATION: primer

<400> SEQUENCE: 72
gtgagaattc tctttgaaaa gataatgtat gattatgc 38

<210> SEQ ID NO 73
<211> LENGTH: 39
<212> TYPE: DNA
<213> ORGANISM: Artificial Sequence
<220> FEATURE:

<223> OTHER INFORMATION: primer

<400> SEQUENCE: 73
acggctcttc gtctttgaaa agataatgta tgattatgc 39

<210> SEQ ID NO 74
<211> LENGTH: 43
<212> TYPE: DNA
<213> ORGANISM: Artificial Sequence
<220> FEATURE:
<223> OTHER INFORMATION: primer

<400> SEQUENCE: 74
acggctcttc gagagtctcc aattatctag taaaaaaagc acc 43

<210> SEQ ID NO 75
<211> LENGTH: 47
<212> TYPE: DNA
<213> ORGANISM: Artificial Sequence
<220> FEATURE:
<223> OTHER INFORMATION: primer

<400> SEQUENCE: 75
cgtcatgtca ctagtagagt ctccaattat ctagtaaaaa aagcacc 47

<210> SEQ ID NO 76
<211> LENGTH: 30
<212> TYPE: DNA
<213> ORGANISM: Artificial Sequence
<220> FEATURE:
<223> OTHER INFORMATION: primer

<400> SEQUENCE: 76
gtgagaattc gagggcctat ttcccatgat 30

<210> SEQ ID NO 77
<211> LENGTH: 30
<212> TYPE: DNA
<213> ORGANISM: Artificial Sequence
<220> FEATURE:
<223> OTHER INFORMATION: primer

<400> SEQUENCE: 77
acggctcttc gtctgtctgc agaattggcg 30

<210> SEQ ID NO 78
<211> LENGTH: 34
<212> TYPE: DNA
<213> ORGANISM: Artificial Sequence
<220> FEATURE:
<223> OTHER INFORMATION: primer

<400> SEQUENCE: 78
agcgctcttc tagagagggc ctatttccca tgat 34

<210> SEQ ID NO 79
<211> LENGTH: 34
<212> TYPE: DNA
<213> ORGANISM: Artificial Sequence
<220> FEATURE:
<223> OTHER INFORMATION: primer

<400> SEQUENCE: 79
cgtcatgtct ctagatttgt ctgcagaatt ggcg 34

<210> SEQ ID NO 80
<211> LENGTH: 23
<212> TYPE: DNA
<213> ORGANISM: Artificial Sequence
<220> FEATURE:
<223> OTHER INFORMATION: primer

<400> SEQUENCE: 80
atccgaacgt acgagtgcaa gcc 23

<210> SEQ ID NO 81
<211> LENGTH: 23
<212> TYPE: DNA
<213> ORGANISM: Artificial Sequence
<220> FEATURE:
<223> OTHER INFORMATION: primer

<400> SEQUENCE: 81
aacggcttgc actcgtacgt tcg 23

<210> SEQ ID NO 82
<211> LENGTH: 23
<212> TYPE: DNA
<213> ORGANISM: Artificial Sequence
<220> FEATURE:
<223> OTHER INFORMATION: primer

<400> SEQUENCE: 82
atcgaacgta cgagtgcaag cct 23

<210> SEQ ID NO 83
<211> LENGTH: 23
<212> TYPE: DNA
<213> ORGANISM: Artificial Sequence
<220> FEATURE:
<223> OTHER INFORMATION: primer

<400> SEQUENCE: 83
aacaggcttg cactcgtacg ttc 23

<210> SEQ ID NO 84
<211> LENGTH: 23
<212> TYPE: DNA
<213> ORGANISM: Artificial Sequence
<220> FEATURE:
<223> OTHER INFORMATION: primer

<400> SEQUENCE: 84
atcaacgtac gagtgcaagc ctg 23

<210> SEQ ID NO 85
<211> LENGTH: 23
<212> TYPE: DNA
<213> ORGANISM: Artificial Sequence
<220> FEATURE:
<223> OTHER INFORMATION: primer

<400> SEQUENCE: 85
aaccaggctt gcactcgtac gtt 23

<210> SEQ ID NO 86
<211> LENGTH: 23
<212> TYPE: DNA
<213> ORGANISM: Artificial Sequence
<220> FEATURE:
<223> OTHER INFORMATION: primer

<400> SEQUENCE: 86
atcacgtacg agtgcaagcc tgg 23

<210> SEQ ID NO 87
<211> LENGTH: 23
<212> TYPE: DNA
<213> ORGANISM: Artificial Sequence
<220> FEATURE:
<223> OTHER INFORMATION: primer

<400> SEQUENCE: 87
aacccaggct tgcactcgta cgt 23

<210> SEQ ID NO 88
<211> LENGTH: 23
<212> TYPE: DNA
<213> ORGANISM: Artificial Sequence
<220> FEATURE:
<223> OTHER INFORMATION: primer

<400> SEQUENCE: 88
atcacgagtg caagcctggg gga 23

<210> SEQ ID NO 89
<211> LENGTH: 23
<212> TYPE: DNA
<213> ORGANISM: Artificial Sequence
<220> FEATURE:
<223> OTHER INFORMATION: primer

<400> SEQUENCE: 89
aactccccca ggcttgcact cgt 23

<210> SEQ ID NO 90
<211> LENGTH: 23
<212> TYPE: DNA
<213> ORGANISM: Artificial Sequence
<220> FEATURE:
<223> OTHER INFORMATION: primer

<400> SEQUENCE: 90
atctgcaagc ctgggggatg gat 23

<210> SEQ ID NO 91
<211> LENGTH: 23
<212> TYPE: DNA
<213> ORGANISM: Artificial Sequence
<220> FEATURE:
<223> OTHER INFORMATION: primer

<400> SEQUENCE: 91
aacatccatc ccccaggctt gca 23

<210> SEQ ID NO 92
<211> LENGTH: 23
<212> TYPE: DNA
<213> ORGANISM: Artificial Sequence
<220> FEATURE:
<223> OTHER INFORMATION: primer

<400> SEQUENCE: 92
atccagacag accatactcc aga 23

<210> SEQ ID NO 93
<211> LENGTH: 23

<212> TYPE: DNA
<213> ORGANISM: Artificial Sequence
<220> FEATURE:
<223> OTHER INFORMATION: primer

<400> SEQUENCE: 93
aactctggag tatggtctgt ctg 23

<210> SEQ ID NO 94
<211> LENGTH: 23
<212> TYPE: DNA
<213> ORGANISM: Artificial Sequence
<220> FEATURE:
<223> OTHER INFORMATION: primer

<400> SEQUENCE: 94
atcagacaga ccatactcca gat 23

<210> SEQ ID NO 95
<211> LENGTH: 23
<212> TYPE: DNA
<213> ORGANISM: Artificial Sequence
<220> FEATURE:
<223> OTHER INFORMATION: primer

<400> SEQUENCE: 95
aacatctgga gtatggtctg tct 23

<210> SEQ ID NO 96
<211> LENGTH: 23
<212> TYPE: DNA
<213> ORGANISM: Artificial Sequence
<220> FEATURE:
<223> OTHER INFORMATION: primer

<400> SEQUENCE: 96
atcgacagac catactccag atg 23

<210> SEQ ID NO 97
<211> LENGTH: 23
<212> TYPE: DNA
<213> ORGANISM: Artificial Sequence
<220> FEATURE:
<223> OTHER INFORMATION: primer

<400> SEQUENCE: 97
aaccatctgg agtatggtct gtc 23

<210> SEQ ID NO 98
<211> LENGTH: 23
<212> TYPE: DNA
<213> ORGANISM: Artificial Sequence
<220> FEATURE:
<223> OTHER INFORMATION: primer

<400> SEQUENCE: 98
atcacagacc atactccaga tgg 23

<210> SEQ ID NO 99
<211> LENGTH: 23
<212> TYPE: DNA
<213> ORGANISM: Artificial Sequence
<220> FEATURE:
<223> OTHER INFORMATION: primer

<400> SEQUENCE: 99
aacccatctg gagtatggtc tgt 23

<210> SEQ ID NO 100
<211> LENGTH: 23
<212> TYPE: DNA
<213> ORGANISM: Artificial Sequence
<220> FEATURE:
<223> OTHER INFORMATION: primer

<400> SEQUENCE: 100
atcaccatac tccagatggg gga 23

<210> SEQ ID NO 101
<211> LENGTH: 23
<212> TYPE: DNA
<213> ORGANISM: Artificial Sequence
<220> FEATURE:
<223> OTHER INFORMATION: primer

<400> SEQUENCE: 101
aactccccca tctggagtat ggt 23

<210> SEQ ID NO 102
<211> LENGTH: 23
<212> TYPE: DNA
<213> ORGANISM: Artificial Sequence
<220> FEATURE:
<223> OTHER INFORMATION: primer

<400> SEQUENCE: 102
atcactccag atgggggatg gct 23

<210> SEQ ID NO 103
<211> LENGTH: 23
<212> TYPE: DNA
<213> ORGANISM: Artificial Sequence
<220> FEATURE:
<223> OTHER INFORMATION: primer

<400> SEQUENCE: 103
aacagccatc ccccatctgg agt 23

<210> SEQ ID NO 104
<211> LENGTH: 25
<212> TYPE: DNA
<213> ORGANISM: Artificial Sequence
<220> FEATURE:
<223> OTHER INFORMATION: primer

<400> SEQUENCE: 104
caccgacgta cgagtgcaag cctgg 25

<210> SEQ ID NO 105
<211> LENGTH: 25
<212> TYPE: DNA
<213> ORGANISM: Artificial Sequence
<220> FEATURE:
<223> OTHER INFORMATION: primer

<400> SEQUENCE: 105
aaacccaggc ttgcactcgt acgtc 25

<210> SEQ ID NO 106
<211> LENGTH: 25
<212> TYPE: DNA
<213> ORGANISM: Artificial Sequence
<220> FEATURE:
<223> OTHER INFORMATION: primer

<400> SEQUENCE: 106
caccgacaga ccttactcca gaagg 25

<210> SEQ ID NO 107
<211> LENGTH: 25
<212> TYPE: DNA
<213> ORGANISM: Artificial Sequence
<220> FEATURE:
<223> OTHER INFORMATION: primer

<400> SEQUENCE: 107
aaacccttct ggagtaaggt ctgtc 25

<210> SEQ ID NO 108
<211> LENGTH: 25
<212> TYPE: DNA
<213> ORGANISM: Artificial Sequence
<220> FEATURE:
<223> OTHER INFORMATION: primer

<400> SEQUENCE: 108
caccgtgcaa gcctggggga aggat 25

<210> SEQ ID NO 109
<211> LENGTH: 25
<212> TYPE: DNA
<213> ORGANISM: Artificial Sequence
<220> FEATURE:
<223> OTHER INFORMATION: primer

<400> SEQUENCE: 109
aaacatcctt cccccaggct tgcac 25

<210> SEQ ID NO 110
<211> LENGTH: 25
<212> TYPE: DNA
<213> ORGANISM: Artificial Sequence
<220> FEATURE:
<223> OTHER INFORMATION: primer

<400> SEQUENCE: 110
caccgactcc agaaggggga aggct 25

<210> SEQ ID NO 111
<211> LENGTH: 25
<212> TYPE: DNA
<213> ORGANISM: Artificial Sequence
<220> FEATURE:
<223> OTHER INFORMATION: primer

<400> SEQUENCE: 111
aaacagcctt cccccttctg gagtc 25

<210> SEQ ID NO 112
<211> LENGTH: 25
<212> TYPE: DNA
<213> ORGANISM: Artificial Sequence
<220> FEATURE:
<223> OTHER INFORMATION: primer

<400> SEQUENCE: 112
caccgacgag tgcaagcctg gggga 25

<210> SEQ ID NO 113
<211> LENGTH: 25
<212> TYPE: DNA
<213> ORGANISM: Artificial Sequence
<220> FEATURE:
<223> OTHER INFORMATION: primer

<400> SEQUENCE: 113
aaactccccc aggcttgcac tcgtc 25

<210> SEQ ID NO 114
<211> LENGTH: 25
<212> TYPE: DNA
<213> ORGANISM: Artificial Sequence
<220> FEATURE:
<223> OTHER INFORMATION: primer

<400> SEQUENCE: 114
caccgacctt actccagaag gggga 25

<210> SEQ ID NO 115
<211> LENGTH: 25
<212> TYPE: DNA
<213> ORGANISM: Artificial Sequence
<220> FEATURE:
<223> OTHER INFORMATION: primer

<400> SEQUENCE: 115
aaactccccc ttctggagta aggtc 25

<210> SEQ ID NO 116
<211> LENGTH: 88
<212> TYPE: DNA
<213> ORGANISM: Artificial Sequence
<220> FEATURE:
<223> OTHER INFORMATION: iCas9 site

<400> SEQUENCE: 116
tccgatccat cccccaggct tgcactcgta cgttcgaaat attataaatt atcagacaga 60
ccatactcca gatgggggat ggctaggt 88

<210> SEQ ID NO 117
<211> LENGTH: 88
<212> TYPE: DNA
<213> ORGANISM: Artificial Sequence
<220> FEATURE:
<223> OTHER INFORMATION: iCas9 site

<400> SEQUENCE: 117
tccgatcctt cccccaggct tgcactcgta cgttcgaaat attataaatt atcagacaga 60
ccttactcca gaagggggaa ggctaggt 88

<210> SEQ ID NO 118
<211> LENGTH: 123
<212> TYPE: DNA
<213> ORGANISM: Artificial Sequence
<220> FEATURE:
<223> OTHER INFORMATION: iCas9 site with accessory site

<400> SEQUENCE: 118
tccgatcctt cccccaggct tgcactcgta cgttcgaaat attataaatt atcagacaga 60
ccttactcca gaagggggaa ggctaggtgg ctaccggtcg ccaccatggt gagcaagggc 120
gag 123

-continued

```
<210> SEQ ID NO 119
<211> LENGTH: 123
<212> TYPE: DNA
<213> ORGANISM: Artificial Sequence
<220> FEATURE:
<223> OTHER INFORMATION: iCas9 site with accessory site

<400> SEQUENCE: 119

tccgatcctt cccccaggct tgcactcgta cgttcgaaat attataaatt atcagacaga      60

ccttactcca gaagggggaa ggctaggtgg ctaccggtcg ccaccatggt gagcaagggc     120

gag                                                                   123


<210> SEQ ID NO 120
<211> LENGTH: 16
<212> TYPE: PRT
<213> ORGANISM: Artificial Sequence
<220> FEATURE:
<223> OTHER INFORMATION: linker

<400> SEQUENCE: 120

Ser Gly Ser Glu Thr Pro Gly Thr Ser Glu Ser Ala Thr Pro Glu Ser
1               5                   10                  15


<210> SEQ ID NO 121
<211> LENGTH: 21
<212> TYPE: PRT
<213> ORGANISM: Artificial Sequence
<220> FEATURE:
<223> OTHER INFORMATION: linker

<400> SEQUENCE: 121

Gly Gly Ser Gly Gly Ser Gly Ser Glu Thr Pro Gly Thr Ser Glu Ser
1               5                   10                  15

Ala Thr Pro Glu Ser
            20
```

CAS9 FUSION PROTEINS AND RELATED METHODS

RELATED APPLICATIONS

This application is the U.S. National Stage of International patent application no. PCT/US2020/028149, filed Apr. 14, 2020, which claims the benefit of U.S. provisional patent application No. 62/834,880, filed Apr. 16, 2019 titled "CAS9 Fusion Proteins and Related Methods, the contents of each of which are hereby incorporated by reference in their entireties.

STATEMENT REGARDING FEDERALLY SPONSORED RESEARCH OR DEVELOPMENT

This invention was made with government support under GM106081 awarded by the National Institutes of Health. The government has certain rights in the invention.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 42,484 byte ASCII (text) file named "20220426_SeqList" created on Apr. 26, 2022.

TECHNICAL FIELD

The disclosure is directed to recombinant Cas9 fusion proteins capable of targeted DNA deletion and DNA integration in a cell without triggering the cell's endogenous DNA repair mechanism such as, homologous recombination. The Cas9 fusion proteins disclosed herein also minimize off target mutations, nucleotide insertions, and/or nucleotide deletions.

BACKGROUND

Clustered regularly interspaced short palindromic repeats (CRISPR) and CRISPR-associated (Cas) systems, such as Cas9 nuclease and Cas12a (Cpf1), have drastically improved the ease of targeted DNA modifications, largely due to its ability to target Cas9's function via design and co-expression of single guide RNAs (sgRNAs) or CRISPR RNA (crRNAs) for Cas12a. In the case of Cas9, sgRNA targeting is straightforward as it requires only simple DNA-RNA base pairing combined with the presence of a protospacer adjacent motif (PAM) on the target DNA. Systems employing Cas9 are highly robust and function in a broad range of organisms for a variety of editing strategies. Strategies for DNA integration and deletion are largely accomplished via formation of DSBs or paired single-stranded DNA breaks (SSBs) followed by processing via endogenous non-homologous end joining (NHEJ) or homologous recombination (HR). More recently, groups have described homology independent target integration (HITI), an effective technique for NHEJ mediated genome integration. This technique produces simultaneous CRISPR-Cas9-targeted double-stranded breaks (DSBs) on plasmid and genomic protospacer sequences and then utilize NHEJ to ligate plasmid DNA into the genomic protospacer. However, it has become apparent that CRISPR-based genome engineering strategies are limited with respect to their dependence on the generation of DSBs and endogenous DNA repair machinery.

DSBs could generate unwanted mutations, translocations, complex rearrangements and destabilize karyotype. This is a fundamental limitation of CRISPR-Cas9's application in editing human cell lines for basic science and therapeutic purposes.

Technologies that avoid incurring double-stranded DNA damages during the editing process include "base-editor" (BE) Cas9 systems, which enable generation of single nucleotide changes without the need for double stranded DNA breaks. BE-Cas9's accomplished single nucleotide changes via fusion of a nicking Cas9 (Cas9D10A) with a cytidine deaminase and uracil glycosylase inhibitor domains. However, BEs are limited to single nucleotide changes. Accordingly, additional developments in the CRISPR-Cas9 technology is needed to prevent the development of unwanted mutations, translocations, complex rearrangements and destabilized karyotype.

SUMMARY

The disclosure is directed to a recombinant Cas9. The recombinant Cas9 preferably comprises a catalytic domain of the resolvase of transposon Tn3 ("Tn3 resolvase"). In some aspects, the disclosure is directed to a Cas9 fusion protein where a catalytically inactive Cas9 is fused with the catalytic domain of a hyperactive mutant Tn3 resolvase. In certain nonlimiting embodiments, the catalytically inactive Cas9 is dCas9. A recombinant Cas9 comprising dCas9 and the catalytic domain of a hyperactive mutant Tn3 resolvase is referred to herein as iCas9.

In some aspects, the dimer of the recombinant Cas9 is described, wherein the dimer is bound to a DNA molecule. In certain embodiments of the dimer, the recombinant Cas9 further comprises a single guide RNA (sgRNA) bound to the catalytically inactive Cas9, and the DNA molecule on which the dimer is bound comprises two binding sites for the sgRNA. The distance between the binding sites for the sgRNA is at least 21 bp, for example, at least 22 bp, 22 bp, 30 bp, 31 bp, 40 bp, or 44 bp. In certain embodiments, the fusion protein of the dimer is bound to the same strand of the DNA molecule. In other embodiments, the fusion protein of the dimer is bound to opposite strands of the DNA molecule.

In some aspects, the tetramer of the recombinant Cas9 is described, wherein the tetramer is bound to a DNA molecule. In some embodiments of the tetramer, the recombinant Cas9 further comprises a sgRNA bound to the catalytically inactive Cas9, and the DNA molecule on which the tetramer is bound comprises two binding sites for the sgRNA. The distance between the binding sites for the sgRNA is at least 21 bp, for example, at least 22 bp, 22 bp, 30 bp, 31 bp, 40 bp, or 44 bp. In certain embodiments, each dimer of the tetramer is bound to the same strand of the DNA molecule. In other embodiments, each dimer of the tetramer is bound to opposite strands of the DNA molecule.

The disclosure is also directed to a method of producing the recombinant Cas9 and the use of the recombinant Cas9 for targeted DNA deletion or targeted DNA insertion in an eukaryotic genome. Kits for evaluating the ability of the recombination Cas9 for targeted DNA deletion or targeted DNA insertion in an eukaryotic genome are also disclosed herein.

BRIEF DESCRIPTION OF THE DRAWINGS

FIGS. 1A-1C depict the design of iCas9 and iCas9 target sites. In accordance with certain embodiments, FIG. 1A shows the architecture of the iCas9 fusion protein. A Catalytically inactive Cas9 (dCas9) is fused to the catalytic domain of a hyperactive mutant recombinase from transposon TN3 (mTN3). dCas9 and mTN3 are separated by a flexible linker region (GGS*6). To promote nuclear entry, both N- and C-Termini have SV40 nuclear localization signals sequences (NLS). Given catalytic domains are fused to dCas9, iCas9 is guided via single guide RNAs (sgRNAs). In accordance with certain embodiments, FIG. 1B shows mTN3 function is dependent on dimerization on target site sequences followed by tetramerization. Tetramerization results in recombination, which can occur in two directions: deletion or integration. iCas9 can target either DNA deletion if target recognition sites are located on the same molecule (left), or alternatively iCas9 can target DNA integration if target sites are on separate DNAs (right). FIG. 1C depicts, in accordance with certain embodiments, the design of an iCas9 recognition site consists of two sgRNA targets (dark and light gray) flanking a TN3 Res1 core recognition sequence (core, orange). The two sgRNAs have a protospacer adjacent motif (PAM, red) distal orientation. mTN3-dCas9 fusions bind in positions around the core sequence allowing for mTN3 catalytic domain dimerization. The components identified by different hatching patterns in FIGS. 1B and 1C correspond with the identified hatching pattern in FIG. 1A.

FIGS. 2A-2F depict, in accordance with certain embodiments, the validation of iCas9 function and target site design using a yeast-based GFP-deletion assay. FIG. 2A depicts a diagram of chromosomally integrated dual-fluorescent reporter for detection of iCas9 function. The reporter contains GFP and mCherry coding regions transcribed from separate TEF1 promoters (arrows). iCas9 recognition sites flank the GFP expression cassette, wherein each site contains a left and right protospacers flanking a TN3 Res1 core sequence. Functional targeting of iCas9 results in GFP deletion generating GFP−, mCherry+ cells. FIG. 2B depicts a representative flow cytometry scatter plot for yeast expressing the reporter, iCas9, sgRNAs G and H after 96 hours of galactose induction of iCas9 expression. NFC is non-fluorescent channel. FIG. 2C depicts systematic analysis of sgRNA spacing on iCas9 function, as measured by GFP-deletion on flow cytometry. Inset shows spacing as measured from 5' ends of sgRNAs flanking the core sequence. sgRNAs A-M are systematically spaced around the core sequence and distances ranging from 16-40 bp. sg(−) is a control guide not matching the target site, where the dashed line indicates background false-GFP-deletion. “Symmetric”, indicates left and right guides are positioned equal distances around the core site. “Asymmetric” guide combinations are at varying distances from the core. FIG. 2D depicts fluorescent microscopy of yeast expressing iCas9 and non-target guide, sg(−), or the 22 bp targeting pair, sg(G:H). GFP and mCherry dual-positive cells are orange on merge, while GFP-deletions appear as red only (GFP−, mCherry+). Scale bar is 20 μm. FIG. 2E depicts gel-electrophoresis of amplicons using primers flanking the reporter locus. The starting reporter results in a 5 Kilobase (Kb) PCR product and GFP-deletion results in a 4 Kb amplicon. Co-expression of iCas9 and sg(G:H) results in detectable DNA-deletion via formation of the 4 Kb product. FIG. 2F depicts sequencing of iCas9 target sites from isolated and sub-cloned deletion amplicons. Sequencing results (SEQ-1 to SEQ-5) aligned to the expected recombination product (EXPECT). Deletion products match the expected recombination sequence and are free of insertion deletion (indel) mutations. The components identified by different hatching patterns in FIGS. 2C and 2E correspond with the identified hatching pattern in FIG. 2A.

FIG. 3A depicts dual-fluorescence plasmid systems contains an EF1α-HTLV promoter (arrow), iCas9 recognition sites (rectangles) flanking mCherry and a downstream GFP reading frame. iCas9 targeting results in deletion of mCherry and generation of a GFP only vector. FIG. 3B depicts GFP expression in HEK293T co-transfected with the GFP− mCherry reporter plasmid, iCas9 and guides targeting the recognition sites. Co-transfection of iCas9 and a non-target guide (−) resulted in no shift of GFP expression. However, targeting with 22, 30 and 40 bp sgRNA spacing's spacing shifted GFP by 2.8±0.7, 2.7±0.0.4 and 1.3±0.4% respectively. NS is Non-significant, * is $P<0.05$.

FIG. 4A depicts a dual-plasmid reporter for detection of intermolecular recombination. A promoterless GFP-donor vector contains an iCas9 recognition site. A separate mCherry acceptor vector contains an EF1α-HTLV promoter with iCas9 target site and mCherry downstream. Recombination results in placement of GFP downstream of the promoter and mCherry-GFP dual-positive cells. FIG. 4B shows fluorescence of HEK293 Ts co-transfected with dual-reporter plasmids, iCas9 and sgRNAs. Scale bar is 200 μm. FIG. 4C depicts flow cytometry scatter plots of plasmid-to-plasmid recombination experiments. Untransfected HEK293 Ts (gray, lower left, LL) were used to define gates for GFP+ and mCherry+ (dashed lines). HEK293 Ts were co-transfected with reporter vectors, iCas9 and non-targeting sg(−) (red) or sg(G:H) (blue). Targeting resulted in GFP-mCherry dual-positive cells (upper right, UR). FIG. 4D depicts fold-increase of GFP-mCherry dual-positive cells for iCas9 transfections. Targeting of GFP-donor and mCherry-acceptor with sg(G:H) results in a 10.6±0.5 fold-increase of dual-positive cells, results of recombination, at the target site compared to a control sgRNA sg(−).

FIGS. 5A-5F depict, in accordance with certain embodiments, multiplex-targeting of iCas9 enables genome integration in human cells. FIG. 5A depicts a genome integrated mCherry acceptor cassette contains an EF1α-HTLV promoter and downstream iCas9 recognition site with an mCherry coding sequence. Integration of GFP into the genomic acceptor cassette results in GFP+ cells. FIG. 5B depicts a design scheme for accessory targeting adjacent to the iCas9 core target site. Recombination between GFP-donor (green) and mCherry-acceptor (red) is coordinated by multiplex targeting of iCas9 binding. Accessory guide sites were targeted downstream of the iCas9 core site. Targeting of the + or − strand and varying distances (X bp) were tested. FIG. 5C depicts the fold-increase of GFP+ over sg(−) control. Targeting with iCas9 at the core site and downstream accessory 21 bp away resulted in 9.4±2.5 fold-increase of GFP+ cells. FIG. 5D depicts PCR detection of integration from isolated genomic DNA using primers flanking the recombination junction (inset by photo). “Mock” is a mock transfection of the mCherry-acceptor HEK293T cell line. iCas9 and GFP-donor were co-transfected with various guide combinations, (−) is a non-target guide, (G:H) is the 22 bp spacing without accessory guide, and (G:H:M) is 22 bp spacing with accessory targeting. FIG. 5E depicts alignments of sub-cloned and sequenced PCR products against the expected recombination product (EXPECT). SEQ-1 to SEQ-5 are free of indel mutations. FIG. 5F depicts alignments of sub-cloned and sequenced PCR products for Cas9WT-targeted NHEJ-mediated integration products. Some products contain indel mutations.

FIG. 6A depicts a yeast genome integration vector with reporter for iCas9 function. The plasmid contains a HIS3 (histidine) prototrophic marker. URA3 homology arms (HAs) contain distinct StuI and ApaI sites. Digestion generates a linear plasmid capable of genome integration at the URA3 locus. The plasmid contains a constitutive mCherry cassette with a translation elongation factor 1 (TEF1) promoter. A constitutive enhanced GFP (eGFP) cassette is flanked by iCas9-sites (see FIG. 7). iCas9-sites are cloned into EcoRI and MluI restriction sites upstream and downstream of the eGFP cassette. The plasmid contains a ColE1 origin of replication and ampicillin selection marker for bacterial propagation. FIG. 6B shows p415-Gall-iCas9, which is the episomal expression vector for iCas9. iCas9 is composed of mTN3 catalytic domain, glycine serine (GGS) 6 linker and dCas9 (i.e. Cas9 D10A, H840A). A galactose inducible (GAL1) promoter controls expression of iCas9. The plasmid contains a Cen6-ARS yeast episomal replication origin and LEU2 (leucine) prototrophic marker for positive selection. FIG. 6C shows pYSG0-1C3, which is a cloning chassis for generating individual sgRNA cassettes. Guide oligonucleotide duplexes are cloned into SapI digested vector (highlighted on inset), wherein a small nucleolar-RNA 52 (SNR52, green) promoter is upstream and the *S. pyogenes* sgRNA hairpin structure is downstream (blue). The vector contains a ColE1 origin of replication and chloramphenicol resistance cassette. FIG. 6D shows pRS424-sgRNA(s), which is used for expression of guides in yeast. The yeast episomal vector contains a 2μ origin of replication and TRP1 (tryptophan) prototrophic marker. SNR52 promoters drive expression of each sgRNA (e.g. sg(G:H) shown). Individual or multiplex guides are cloned into distinct EcoRI and SpeI sites.

FIG. 9A depicts the iCas9 primary structure, with N-terminus (N) and C-terminus (C). Both termini have SV40 nuclear localization sequences (NLS). A TN3 resolvase catalytic domain (mTN3) is upstream of a dCas9 coding region. A linker region is between mTN3 and dCas9. A series of amino acid sequences on iCas9 function was tested. These range from short glycine serine (Linker-1) to longer glycine serine (linker-2), previously described linkers for dCas9 fusions (XTEN3, Linker-3) and a novel fusion of glycine serine and XTEN (Linker-4). FIG. 9B depicts a yeast genome GFP-deletion assay with aforementioned linkers and functional sgRNA pairs sg(G:H), 22 bp; sg(K:L), 40 bp. sg(−) is a non-target control guide.

FIG. 10A depicts a 'Traffic-light' (TL) reporter for iCas9 function in human cells. A EF1α-HTLV promoter drives expression of mCherry and eGFP reading frames. mCherry is flanked by iCas9-sites. Deletion of mCherry results in cells with relative GFP+. A rabbit β-globin terminator is downstream of eGFP and mCherry. Sequences are cloned into a pUC19 backbone. FIG. 10B depicts pUC19-mCherry-acceptor (MA), which has an EF1α-HTLV promoter that drives expression of a mCherry fused with a puromycin resistance cassette. A single iCas9-site enables integration downstream of the promoter. FIG. 10C depicts a promoterless eGFP cassette with iCas9-site on the pSB1C3 backbone. eGFP is conditionally expressed when integrated at iCas9-sites. FIG. 10D depicts pKSBRV-1, which is a 2nd generation retroviral vector with mCherry-T2A-PuroR. A single iCas9-site is between mCherry and the Ef1α-HTLV promoter. After viral transduction, this functioned as the genomic reporter locus. FIG. 10E depicts a dual-targeted sgRNA expression vector. Human U6 promoters drive expression of each guide (e.g. sg(G:H), blue). FIG. 10F depicts a transient iCas9 expression vector. A CBH promoter drives expression of mTN3-(GGS)6-dCas9 (i.e. iCas9).

DETAILED DESCRIPTION

Figure 1C:
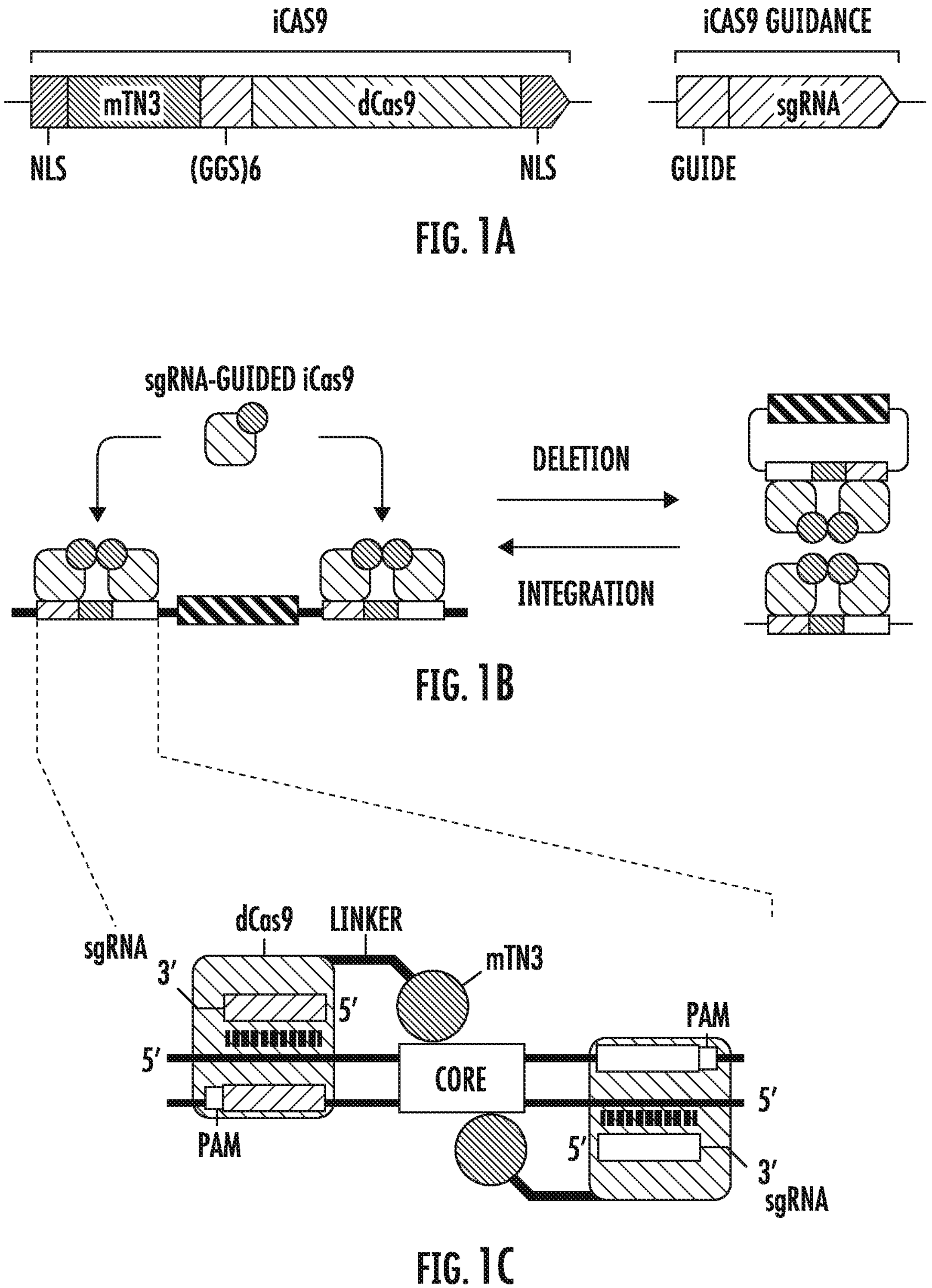

Detailed aspects and applications of the disclosure are described below in the following drawings and detailed description of the technology. Unless specifically noted, it is intended that the words and phrases in the specification and the claims be given their plain, ordinary, and accustomed meaning to those of ordinary skill in the applicable arts.

In the following description, and for the purposes of explanation, numerous specific details are set forth in order to provide a thorough understanding of the various aspects of the disclosure. It will be understood, however, by those skilled in the relevant arts, that embodiments of the technology disclosed herein may be practiced without these specific details. It should be noted that there are many different and alternative configurations, devices and technologies to which the disclosed technologies may be applied. The full scope of the technology disclosed herein is not limited to the examples that are described below.

The singular forms "a," "an," and "the" include plural referents unless the context clearly dictates otherwise. Thus, for example, reference to "a step" includes reference to one or more of such steps.

As referenced herein, the spacing between sequences elements are measured as the bp distance between adjacent ends. For example, the spacing between accessories sgRNAs and the iCas9-site is the bp distance between the right guide of the iCas9-site (i.e. sg(H)) and the start of the accessory guide (e.g. sg(M) or (N)).

While clustered regularly interspaced short palindromic repeats (CRISPR) and CRISPR-associated (Cas) systems have made headlines as powerful tool for genome editing, site-specific recombinases are also powerful tools for genome engineering and synthetic biology. Site-specific recombinases are capable of facilitating DNA rearrangements with high predictability and specificity without incurring DSBs. These proteins possess the enzymatic machinery to facilitate transient DNA cleavage, strand-exchange and re-ligation without the need for high energy cofactors, DNA replication or DSB repair. Certain site-specific recombinases, such as ΦC31, are limited to specific ~30 bp recognition sites and are often used for integration at specific 'landing pad' or pseudo-site loci. To circumvent this, directed evolution has been employed to retarget recombinase substrate specificity. For instance, Karpinski et al. reported directed evolution of Cre recombinase to target conserved sequences Human Immuno-deficiency Virus (HIV) long-terminal repeats (LTRs). This system led to efficient and highly specific excision of the HIV provirus; however, nearly 150 rounds of directed evolution were required. Alternatively, recombinases have been retargeted by fusing catalytic-domains to zinc finger or transcriptional activator-like (TAL) DNA-binding domains. These techniques however require complex addition of heterologous DNA-binding domains.

The disclosure relates to a new tool for genome editing that takes advantage of the programmability of the CRISPR-Cas system for targeted gene editing while using the functionality of a site-directed recombinase. The disclosure reports that a fusion protein comprising a catalytically inactive Cas9 fused with the catalytic domain of a recombinase overcomes the limitations of both the CRISPR-Cas system and site-directed recombinases. The recombinase is a TN3 resolvase. The examples demonstrate the function of iCas9 using the native TN3 core sequence. Likewise, zinc finger recombinase literature has focused largely on targeting canonical core sequences. There have been conflicting reports about the versatility of this family of serine recombinases. Some reports indicate Gin recombinase, a TN3 resolvase homolog, is highly versatile. However, other reports indicate directed evolution and rationally targeted mutagenesis are required to retarget substrate specificity. The versatility of iCas9's core sequence could be increased by fusion with highly versatile PAM-variant Cas9s, such as xCas9 or Cas9 orthologs in certain embodiment.

In some aspects, the fusion protein comprises a catalytically inactive Cas9 and a catalytic domain of a hyperactive Tn3 transposon resolvase. For example, the fusion protein comprises a catalytically inactive Cas9 and a catalytic domain of a hyperactive Tn3 transposon resolvase, where a first linker connects the C-terminus of the catalytic domain of the recombinase to the N-terminus of the catalytically inactive Cas9. The fusion protein also comprises a first nuclear localization signal, where a second linker connects the first nuclear localization signal to the C-terminus of the catalytically inactive Cas9 or the N-terminus of the catalytic domain of the recombinase. In some embodiments, the fusion protein further comprises a second nuclear localization signal wherein the first nuclear localization signal adjacent to the C-terminus of the catalytically inactive Cas9 and the second nuclear localization signal is adjacent to the N-terminus of the catalytic domain of the recombinase. Such embodiments of the fusion protein further comprise a third linker, wherein the second linker connects the first nuclear localization signal to the C-terminus of the catalytically inactive Cas9 and the third linker connects the second nuclear localization signals to the N-terminus of the catalytic domain of the recombinase. In some aspects, the linkers are flexible glycine serine linkers. For example, the amino acid sequence of the linker comprises repeats of GGS, SGSETPGTSESATPES (SEQ ID NO. 120), GGSGGSG-SETPGTSESATPES (SEQ ID NO. 121), or combinations thereof. In certain embodiments, the nuclear localization signal is from SV40.

In a particular embodiments, the fusion protein is a hyperactive mutant TN3 resolvase fused to dCas9 with an amino acid sequence set forth in SEQ ID NO. 1, or having at least 90%, at least 92%, at least 94%, at least 95%, at least 96%, at least 97%, at least 98%, or at least 99% sequence similarity thereto, or the nucleic acid sequence set forth in SEQ ID NO. 2 having at least 80%, at least 85%, at least 90%, at least 92%, at least 94%, at least 95%, at least 96%, at least 97%, at least 98%, or at least 99% sequence similarity (also referred to herein as "iCas"). The disclosure also encompasses the method of producing iCas9.

As shown in the examples, iCas9 is capable of targeted DNA deletion and targeted DNA insertion of the genome of multiple eukaryotic hosts, ranging from yeast to human cells. However, unlike other recombinant Cas9, the optimal spacing between the guide sequences is greater than 20 bp, as shorter spacing resulted in little to no recombination (FIG. 2).

Figure 8:
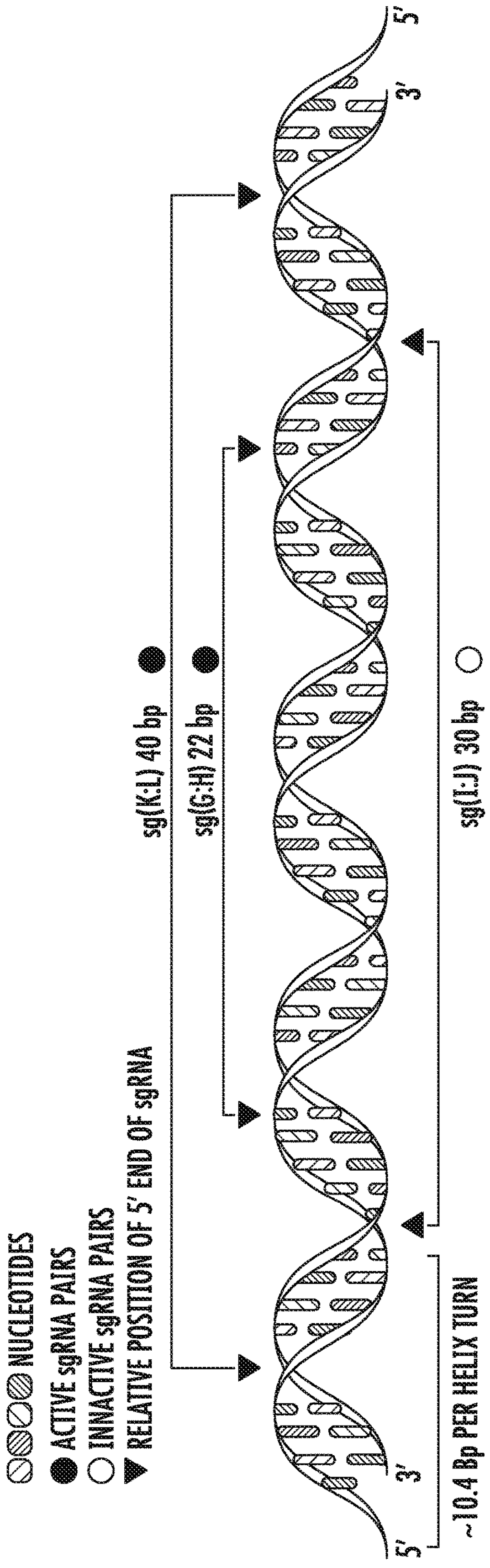
FIG. 8 depicts, in accordance with certain embodiments, an explanatory graphic for functional sgRNA spacings. A conceptual illustration of the effect of sgRNA spacings. The DNA helix is approximately 10.5 bp per helix turn1. Likewise, γΔ resolvase (a close homolog to TN3 resolvase) DNA-binding domains bind to the same helical face and present catalytic domains in a specific orientation with respect to the substrate DNA. This corresponds to functional sgRNA spacing of 22 bp (sg(G:H)) and 40 bp (sg(K:L). The 22 bp spacing positions 5' end's of guides on the same helical face. However 30 bp (sg(I:J)) places left and right sgRNAs on the same face, but the opposite with respect to 22 bp. 40 bp results in placement of 5' end of sgRNAs on the same face as 22 bp. Similar targeting patterns have been reported with FokI-dCas9 fusions, where the functional requirements of the FOKI restriction enzyme domains constrain functional sgRNA pairs to specific nucleotide spacings.

The yeast experiments (see Example 3) identified optimal symmetric spacing's of 22 and 40 bp and asymmetric spacing's of 31 bp. Interestingly, this is consistent with the Watson-Crick DNA structure being 10.5 bp per helix turn combined with the requirement for co-localization of mTN3 catalytic domains to the same helical face of the DNA molecule (See FIG. 8). Furthermore, optimal sgRNA spacing of 22 bp is corroborated by zinc finger mTN3 fusions, which have an optimal spacing of 20-22 bp. In general, this is supported by FokI-dCas9 fusions that use 15 or 25 bp spacings, where these spacings match the requirement for FokI dimerization on opposite DNA helical faces.

As shown in Example 4, iCas9 is capable of targeted DNA deletion and targeted DNA insertion in human cells, and the results confirmed the functionality of the 22 bp sgRNA spacing. The experiments in human cells also found 30 bp to be functional, which is consistent with previous reports using analogous recombinase-Cas9 designs. These altered spacing stringencies may be due to the use of supercoiled plasmids as substrates, which may have different spacing requirements than linear genomic DNA.

Accordingly, iCas9 may be a useful tool for targeted DNA integration. While previous reports have fused dCas9 to recombinase domains, these systems were incapable of genomic integration. For the first time, iCas9's ability to target intermolecular recombination has been validated, and it was through the use of an episomal assay described herein. The experimental design separated the assay from constraints of targeting the human genome, such as being long linear DNAs constrained in 3D space and compacted into different nuclear regions. Although the assay confirmed iCas9 is capable of targeting linear eukaryotic genomic DNA (FIG. 2) and can direct plasmid-to-plasmid recombination (FIG. 4), Donor-DNA-iCas9 complexes still did not interact with the genomic target locus. To address this, the guide sequence vector design was adopted to a scheme of accessory target site binding, wherein sgRNAs are targeted adjacent to the core sequence guides. Accessory binding sites for TN3 resolvase have been implicated in regulating 3D presentation of recombinase subunits, local DNA supercoiling and result in improved recombination efficiency. A tiling of sgRNAs was designed to test if accessory binding sites can be recapitulated with iCas9. Interestingly, the verified functionality of 21 bp spacing and sgRNA orientation of accessory sg(M) approximates the 22 bp spacing observed between the Res1-core and adjacent accessory binding sites native to TN3 transposon (FIG. 5).

iCas9 targeting of endogenous loci can be accomplished through a mixture of multiplex sgRNA design and development of novel-iCas9 derivatives targeting new core sequences, for example "pseudo-core" sites. Because each sgRNA guides an individual iCas9 to the target locus, multiplex targeting is necessary to achieve dimerization and tetramerization. For example, two sgRNA guides would guide dimerization, while four sgRNA guides would guide tetramerization. Targeting with more pairs of sgRNAs, for example, with 6 sgRNA guides would result in hexamerization.

Also described herein are dimer and tetramer of the recombinant Cas9. The dimer of the recombinant Cas9 refers to the fusion protein in a dimerized state, where the dimer is bound to a DNA molecule and a single guide RNA (sgRNA) bound to the catalytically inactive Cas9 portion of the fusion protein. Accordingly, the dimer of the fusion protein comprises two fusion proteins, two sgRNAs, and the DNA molecule. The DNA molecule is a target DNA that comprises binding sites for two single guide RNAs (sgRNA), where the distance between the binding sites for the two sgRNAs is at least 21 bp or at least 22 bp apart, for example, 22 apart, 30 bp apart, 31 bp apart, 40 bp apart, or 44 bp apart. In some aspects, the fusion protein (monomeric units of the dimer) is bound to the same strand of the DNA molecule; in other aspects, they are bound to an opposite strand of the DNA molecule. The tetramer of the recombinant Cas9 refers to the fusion protein in a state where a first dimer of the fusion protein is bound to a second dimer of the fusion protein. Accordingly, the tetramer of the fusion protein comprises four fusion proteins, four sgRNAs, and the DNA molecule. The first dimer and the second dimer are bound to same strand of the DNA molecule in same aspects or are bound to an opposite strand of the DNA molecule in other aspects.

Since iCas9 does have its own fused recombinase functionality, iCas9 may be used for therapeutic purposes or generation of new cell lines, where double-stranded DNA lesions caused by wild type Cas9 can lead to large, multiple kilobase, deletions, insertions, and complex rearrangements. Since iCas9 does not directly rely on DSBs repair pathways such as NHEJ and HR, it reduces the likelihood of precipitating unwanted mutations. Furthermore, mTN3 catalytic domains of iCas9 require paired targeting by sgRNAs (FIG. 2C), it follows that iCas9 should have higher specificity than canonical CRISPR-Cas9 editing techniques that rely on single or double stranded DNA breaks. Moreover, canonical CRISPR-Cas9 editing strategies rely on endogenous DNA repair. This may be detrimental to editing some cell lines recalcitrant to DNA repair. Previous reports have demonstrated the role cell cycle plays in homologous recombination. This has largely limited CRISPR-targeted editing techniques in post-mitotic cells. This may prevent ex vivo editing of patient primary cells. Likewise, it has been shown in embryonic stem cells and epithelial cells that P53 may inhibit repair and survival in cells with CRISPR-targeted DNA lesions. DSB-dependent editing results in an upregulation of P53 and apoptosis of edited populations. While suppression of P53 results in increased editing efficiencies, transient inhibition of P53 may increase tumorigenic potential of the edited cell population. This is an important consideration when developing edited cell populations for cell therapy applications. Since iCas9 utilizes mTN3 catalytic domains for recombination, it avoids the requirement for endogenous DNA repair and may be helpful in editing cell types recalcitrant to DNA manipulations.

iCas9 may also be used in the field of synthetic biology for the construction and implementation of recombinase-based gene networks. Recombinase based gene networks are of increasing interest to synthetic biology. These systems can integrate multiple biological inputs and turn them into saved 'DNA memory'. Recombinase based logic can be constructed in a way to imbue biological systems with Boolean logic functions or even 8-bit memory. These systems are capable of robust function but require coexpression of multiple recombinases and placement of sites corresponding to each recombinase to generate single circuits. iCas9 could enable the generation of RNA-programmed recombinase-based gene networks, wherein different sgRNAs could target different recombinase operations. Unlike previous iterations of recombinase-based gene circuitry, iCas9 systems would only require coexpression of multiple sgRNAs instead of separate recombinases. Numerous sgRNAs could be easily programmed and placed under control of inducible promoters to create circuits that predictably and combinatorically restructure in response to environmental or physiological cues.

In another aspect, the disclosure is directed to methods of using a Cas9 fusion protein (for example, iCas9) for targeted DNA deletion or targeted DNA insertion in a eukaryotic genome. Also disclosed are assay kits and methods for evaluating the ability of a Cas9 fusion protein for targeted DNA deletion and/or targeted DNA integration in eukaryotic cells. In certain embodiments, the assay kits and methods are for evaluating the ability of a Cas9 fusion protein for targeted DNA deletion and/or targeted DNA integration in eukaryotic cells, for example human cells, that is independent of the constraints of targeting the human genome.

In some aspects, the kit for evaluating a recombinant Cas9's ability for targeted DNA deletion in an eukaryotic genome comprises a first expression vector comprising an expression cassette for expressing the recombinant Cas9, a second expression vector encoding guide sequences, and a third expression vector that identifies a target sequence for deletion.

In some embodiments, the kit for evaluating a recombinant Cas9's ability for targeted DNA insertion in an eukaryotic genome comprises a first expression vector comprising an expression cassette for expressing the recombinant Cas9, a second expression vector encoding guide sequences, a third expression vector encoding a acceptor sequence, wherein the third expression vector is a vector that integrates the acceptor sequence into the eukaryotic genome (for example, a retroviral vector), and a fourth expression vector encoding the donor sequence. The first expression vector, the second expression vector, the third expression vector, and the fourth expression vector enable expression in an eukaryotic organism.

In one embodiment, the recombinant Cas9 expressed by the first expression vector is a catalytically inactive Cas9 fused to a catalytic domain of a recombinase. The second expression vector comprises a first single guide RNA (sgRNA) sequence and a second sgRNA sequence. The third expression vector comprises an oligonucleotide encoding a Cas9 site. The third expression vector in the kit for evaluating the ability for targeted DNA deletion comprises the target sequence for deletion and at least one oligonucleotide encoding a Cas9 site, wherein the target sequence for deletion is flanked by the at least one oligonucleotide encoding the Cas9 site. The third expression vector in the kit for evaluating the ability for targeted DNA insertion further comprises an acceptor sequence, wherein the acceptor sequence is upstream of the oligonucleotide encoding the Cas9 site, and a promoter sequence, wherein the promotor sequence drives expression of the acceptor sequence. For the kit for evaluating the ability for targeted DNA insertion, the fourth expression vector is promotorless and comprises a donor sequence and an oligonucleotide encoding the Cas9 site, wherein the donor sequence is downstream of the Cas9 site.

The Cas9 site comprises a core sequence that is recognized by the catalytic domain of the recombinase; a sequence complementary to the first sgRNA sequence that is upstream of and adjacent to the core sequence; a sequence complementary to the second sgRNA sequence that is downstream of and adjacent to the core sequence; and at least two protospacer adjacent motif sequences. Of the at least two protospacer adjacent motif sequences, at least one protospacer adjacent motif sequence is upstream of the sequence complementary to the first sgRNA sequence, and at least one protospacer adjacent motif sequence is downstream of the sequence complementary to the second sgRNA sequence. The distance between the sequence complementary to the first sgRNA sequence and the sequence complementary to the second sgRNA is at least 22 bp apart.

In some embodiments, the second expression vector comprises a third sgRNA sequence and the Cas9 site further comprises an accessory site sequence. The accessory sequence comprises a sequence complementary to the third sgRNA and a protospacer adjacent region distal to the third sgRNA. The distance between the accessory sequence and the sequence complementary to the second sgRNA sequence is at least 21 bp. In other embodiments, the Cas9 site further comprises an accessory site sequence. Thus, the kit further comprises a fifth expression vector that comprises a third sgRNA sequence. The accessory sequence comprises a sequence complementary to the third sgRNA and a protospacer adjacent region distal to the third sgRNA. The distance between the accessory sequence and the sequence complementary to the second sgRNA sequence is at least 21 bp.

In some implementations, the distance between the accessory sequence and the sequence complementary to the second sgRNA sequence is 21 bp.

In some implementations, the sequence complementary to the first sgRNA sequence and the sequence complementary to the second sgRNA sequence on the third expression vector is 22 bp apart. In one aspect, the sequence complementary to the first sgRNA sequence and the sequence complementary to the second sgRNA sequence on the third expression vector is 30 bp apart and the eukaryotic genome is a human genome. In another aspects, the sequence complementary to the first sgRNA sequence and the sequence complementary to the second sgRNA sequence on the third expression vector is 31 bp apart and the eukaryotic genome is a yeast genome. In certain implementations, the sequence complementary to the first sgRNA sequence and the sequence complementary to the second sgRNA sequence on the third expression vector is 40 bp apart.

In certain implementations where the eukaryotic genome is a yeast genome, the oligonucleotide encoding the Cas9 site comprises a nucleic acid sequence set forth in paragraph [0070]. In certain implementations where the eukaryotic genome is a human genome, the oligonucleotide encoding the Cas9 site comprises a nucleic acid sequence set forth in SEQ ID NO. 116, SEQ ID NO. 117, SEQ ID NO. 118 or SEQ ID NO. 119.

The disclosure is also directed to methods of deleting a target sequence from the genome in an eukaryotic cell. The methods comprise introducing into the cell a first nucleotide sequence encoding a recombinant Cas9; introducing a first oligonucleotide sequence encoding a first single guide RNA (sgRNA) sequence and a second oligonucleotide sequence encoding a second sgRNA sequence; coexpressing the nucleotide sequence, the first oligonucleotide sequence, and the second oligonucleotide sequence in the eukaryotic cell to generate a transformed eukaryotic cell; and culturing the transformed eukaryotic cell to remove the region of target sequence from the genome of the cultured eukaryotic cell.

The disclosure additionally is directed to methods of inserting an extraneous sequence into a target region of a genome in a cell. The method comprises introducing into the cell a first nucleotide sequence that encodes the recombinant Cas9 protein described; introducing a first oligonucleotide sequence encoding a first sgRNA sequence, a second oligonucleotide sequence encoding a second sgRNA sequence, and a third oligonucleotide encoding a third sgRNA sequence; introducing a second nucleotide sequence encoding the extraneous sequence and a recognition site sequence for a recombinant Cas9 protein described herein; coexpressing the first nucleotide sequence, the first oligonucleotide sequence, the second oligonucleotide sequence, the third oligonucleotide sequence, and the second nucleotide sequence in the eukaryotic cell to generate a transformed eukaryotic cell; and culturing the transformed eukaryotic cell to insert the extraneous sequence into the genome of the cultured eukaryotic cell at the site of the target region. The recognition site is proximal to the extraneous sequence, and the recognition sequence comprises a sequence complementary to the region of the genome comprising the target region and at least 21 bp from the 3' end of the target region.

The first sgRNA sequence is complementary to the 5' end of a target sequence. The second sgRNA is complementary to the 3' end of the target sequence. The target sequence also has a protospacer adjacent motif that is adjacent to and proximal to its 5' end and a protospacer adjacent motif that is adjacent and distal to its 3' end. The distance between the 5' end of the target sequence and the 3' end of the target sequence is at least 22 bp. The region of the target sequence between the 5' end of the target sequence and the 3' end of the target sequence comprises a sequence recognized by the catalytic domain of the recombinase of the recombinant Cas9 protein described herein. For the methods of inserting an extraneous sequence into a target region of a genome in a cell, the third sgRNA sequence is complementary to a sequence in the genome of the cell that is at least 20 bp from the 3' end of the target region. In some aspects, the third sgRNA sequence is complementary to a sequence in the genome of the cell that is 20 bp or 21 bp from the 3' end of the target region. The sequence in the genome of the cell that is at least 20 bp from the 3' end of the target region comprises a protospacer adjacent motif distal to the sgRNA sequence.

In one implementation of the methods, the distance between the 5' end of the target sequence and the 3' end of the target sequence is 22 bp. In another implementation, the distance between the 5' end of the target sequence and the 3' end of the target sequence is 30 bp. In still another implementation, the distance between the 5' end of the target sequence and the 3' end of the target sequence is 31 bp. In yet another implementation, the distance between the 5' end of the target sequence and the 3' end of the target sequence is 44 bp.

The methods described herein do not cause off target mutations, nucleotide insertions, and/or nucleotide deletions, which are problems encountered when attempting to alter the genome with wildtype Cas9. In some aspects, the portion of the genome is deleted independent of the cell's endogenous DNA repair mechanism. For example, the portion of the genome is deleted by triggering non-homologous end joining.

Illustrative, Non-Limiting Example in Accordance with Certain Embodiments

The disclosure is further illustrated by the following examples that should not be construed as limiting. The contents of all references, patents, and published patent applications cited throughout this application are incorporated herein by reference in their entirety for all purposes.

1. Methods a. Bacterial Culture:

Molecular cloning was conducted using *E. coli* NEB-10-Beta (New England Biolabs, NEB). LB Miller Medium (Sigma Aldrich, Sigma) was supplemented with appropriate antibiotics for plasmid maintenance: Ampicillin (100 μg/ml), or Chloramphenicol (30 μg/ml). *E. coli* were cultured at 37° C.

b. Yeast Culture:

All yeast was cultured at 30° C. *S. cerevisiae* YPH500 were propagated on YPD agar plates and in liquid medium containing glucose. Liquid cultures were shaken at 250-300 RPM. Yeast minimal dropout media contained either 2% glucose or 2% galactose with 1% raffinose and necessary amino acid dropout solutions (Clonetech). Yeast were made competent using the Zymo competent yeast kit and transformed using manufacturer protocol. Genomic integrations and plasmid transformations were selected for on yeast minimal dropout plates with amino acid combinations necessary for selection. Yeast were cultured in liquid yeast dropout media necessary for plasmid selection.

c. Mammalian Cell Culture:

HEK293T cells (ATCC CRL-3216) were cultured on poly-L-ornithine (PLO) (Sigma) coated plates and maintained in Dulbecco's modified eagle medium supplemented with 10% (v/v) fetal bovine serum (FBS) and 1% (v/v) penicillin-streptomycin (all from ThermoFisher). Cells were maintained in a 37° C. incubator with 5% CO2 and passaged once ~80% confluent.

d. Molecular Cloning:

iCas9 (TN3-GGSx6-dCas9) was constructed by fusion of a previously described hyperactive mutant recombinase (TN3 G79S, D102Y, E124Q). The resolvase catalytic domain (AA1-148) was linked to Cas9 D10A, H840A with a flexible glycine serine (GGSx6) linker. N- and C-terminal SV40 nuclear localization sequences with small glycine serine linkers (GGSx1) were added to facilitate nuclear entry. The coding region for the hyperactive TN3 mutant resolvase was synthesized as a human codon optimized gBlock by Integrated DNA technologies (IDT). The gBlock was sub-cloned into a dCas9 derivative of p415 Gall-Cas9 (Addgene #43804). The mTN3 catalytic domain along with D10A and H840A mutations to Cas9 were added using PCR primers containing SapI sites (Table 2). The amino acid sequence of iCas9 is set forth in SEQ ID NO. 1. The nucleic acid sequence of iCas9 is set forth in SEQ ID NO. 2.

Purified PCR products were digested with SapI and gel-extracted using the Sigma-Aldrich gel-extraction kit. iCas9 was assembled in XbaI-XhoI sites of p415 Gall-Cas9. The resulting p415 Gall-iCas9 vector also contains a Cen6 origin of replication and a leucine prototrophic marker. For expression in human cells iCas9 was PCRed with primers adding AgeI and MfeI upstream and downstream respectively. iCas9 was cloned into a modified pX330 with guide expression cassette removed. Digested and gel-extracted iCas9 PCR products were ligated with AgeI and EcoRI digested pX330. The resulting vector contains a CBH-promoter driving iCas9 expression.

sgRNA guides were synthesized as pairs of oligonucleotides. 5' phosphates were added to oligonucleotides by incubating 1 ug total of top/bottom oligonucleotides in 50 μl reactions containing 1× T4 DNA Ligase Buffer and 10 units of T4 Polynucleotide Kinase (T4 PNK) at 37° C. overnight (Tables 1 and 2). Oligonucleotides were duplexed by heating the kinase reactions to 90° C. on an aluminum heating block for 5 minutes followed by slowly returning the reaction to room temperature (25° C.) over approximately 1 hour. Following duplexing, guides were ligated into respective vectors.

Yeast sgRNA expression cassettes, were constructed by cloning oligonucleotide duplexes into, pSB1C3 containing an SNR52 promoter with inverted SapI sites and an sgRNA hairpin recognized by *S. pyogenes* Cas9. Pairs of sgRNAs were then amplified with primers adding EcoRI and SapI, or SapI and SpeI sites. Purified PCR product were then digested with respective restriction enzymes, heat inactivated and ligated into EcoRI and SpeI digested pRS424. The resulting vector contains pairs of yeast sgRNA cassettes with a 2p origin of replication and tryptophan prototrophic marker.

Humanized sgRNAs were cloned into a modified pSB1C3 vector containing a human U6 promoter, inverted BbsI sites and a *S. pyogenes* recognized sgRNA hairpin (Sequence derived from pX330). Pairs of sgRNAs were then amplified with primers adding EcoRI and SapI, or SapI and XbaI sites. Purified PCR product were then digested with respective restriction enzymes, heat inactivated and ligated into EcoRI and XbaI digested pUC19. The resulting vector contains pairs of human sgRNA expression cassettes.

The Yeast Genomic Integration Vector (pMG) was generated using vectors previously described. Tef1 promoters drive constitutive expression of GFP and mCherry. To integrate into the yeast genome, one to two micrograms of pMG was digested with ApaI in 50 μl reactions for one hour or more at 37° C. Five microliters of the restriction product was transformed into competent YPH500 using protocol from Zymo Competent Yeast Kit (Zymo). Integrant were selected for by plating on histidine dropout plates.

To clone iCas9-target sequences into pMG, sites were synthesized as overlapping oligonucleotides. 5' phosphates were added to oligonucleotides by incubating 1 ug of top/bottom oligonucleotides in 50 μl reactions containing 1×T4 DNA Ligase Buffer and 10 units of T4 Polynucleotide Kinase (T4 PNK) at 37° C. overnight. Oligonucleotides were duplexed by heating the kinase reactions to 90° C. on an aluminum heating block for 5 minutes followed by slowly returning the reaction to room temperature (25° C.) over approximately one hour. Following duplexing, sites were ligated into EcorI and MluI sites surrounding GFP.

e. Mammalian Cell Transfections

HEK293T cells were seeded at 1.8×105 cells/well in PLO coated 24-well plate and transfected 24 hours post-passage at ~80% confluency. For plasmid-plasmid assays, 300 ng of iCas9, 100 ng of GFP-encoding donor vector (FeGFP-1C3), 100 ng of mCherry-expressing target vector (pUC:EAMP), and 100 ng sgRNA expression vectors were transfected per well using 1.5 μl Lipofectamine 3000 and 1 μl P3000. For genome integration experiments, 300 ng iCas9 expression vector, 100 ng GFP-encoding donor vector (FeGFP-1C3), 100 ng pIRFP670 and 100 ng sgRNA cassette(s) were transfected using 1.5 μl Lipofectamine 3000 and 1 μl P3000. pIRFP670 was co-transfected as a control with samples at >50% transfection efficiency.

f. Retrovirus and Stable Cell Line Generation

HEK293T cells were passaged to four PLO coated 100 mm culture plates in Opti-MEM reduced serum medium plus GlutaMAX and supplemented with 1 mM sodium pyruvate and 10% (v/v) FBS (all from ThermoFisher). To generate recombinant retroviruses, HEK 293T cells were transfected with the pKSBRV-1 transgene and packaging plasmids (pUMVC and pVSVG). 9 μg pKSBRV-1, 6 μg pUMVC, and 3 μg pVSVG expression plasmids were transfected per plate using 28 μl Lipofectamine 3000 and 36 μl P3000 (ThermoFisher). Media was changed 6 hours post-transfection and lentivirus containing supernatant was collected at 24 hours and 54 hours. Conditioned media was filtered using 0.45 μm filter and lentiviral particles were concentrated using Lenti-X (Takara Bio). HEK293T cells were then infected with the viruses followed by puromycin selection 48 hours later at a concentration of 0.75 μg/mL. Following selection for 2 weeks, cells were FACS sorted for the upper 50% of mCherry expressing cells to generate a pure population of cells stably expressing the transgene.

g. In Yeast GFP-Deletion Assay

To assay iCas9 function, YPH500 Ura3(MGaa) with p415 Gall-iCas9 and with various pRS424 (guide pairs) were cultured in 3 ml YP-Leu, -Trp with 2% Glucose. After 24 hours, 5 μl of the stationary phase culture was used to inoculate 3 ml of YP-Leu, -Trp with 2% Galactose, 1% Raffinose. Cell were diluted down (5 μl saturated culture in 3 ml media) at 48-hour intervals. Cells were analyzed by flow cytometry and fluorescent microscopy after 96 hours of galactose induction. Genomic DNA was also prepared after galactose induction.

h. Flow Cytometry

All flow cytometry was conducted on an Accuri C6 Flow Cytometer (BD Biosciences, CA). Samples were gated by consistent forward scatter (FSC) and side scatter (SSC) and 10,000 events within the FSC/SSC gate were collected. A 488 nm laser excitation and a 530±15 nm emission filter was used for GFP fluorescence determination. Flow cytometry files were analyzed using manufacture software and in MatLab (The MathWorks). Flow cytometry of HEK293T cells was conducted 72 hours post-transfection. Briefly, cells were dissociated using Accutase (ThermoFisher), washed with PBS, and analyzed using a BD Accuri C6 cytometer (BD Biosciences). GFP-positive cells were measured compared to transfections with a non-target sgRNA.

i. Fluorescent Microscopy

200 μl of stationary phase cultures of yeast were spun down at 4000*g for 2 minutes and washed once in 1×PBS solution. Following washing, cells were concentrating by resuspending in 10-20 μl of 1×PBS. 1-2 μl of cell solution was placed on glass microscope slides and visualized on a Nikon Ti-Eclipse inverted microscope with and LED-based Lumencor SOLA SE Light Engine with appropriate filter sets. GFP was visualized with an excitation at 472 nm and emission at 520/35 nm using a Semrock band pass filter. mCherry was visualized with excitation at 562 nm and emission at 641/75 nm. Constant exposure times, LUT and image gain adjustments were applied to microscopy data. HEK293T cells were imaged directly on TC plates 72 hours after transfection.

j. Genomic DNA Isolation and PCR Analysis of GFP Deletions

Yeast genomic DNA was prepared using the Zymo yeast genomic DNA preparation kit using the manufacturer's protocol with phenol-chloroform steps included. To assay genomic deletion, PCR was conducted using Phusion DNA polymerase (New England Biolabs). Annealing temperatures and extension times were calculated using the manufacturer's protocol. PCR products were visualized via 0.8% agarose gel electrophoresis. Human cell genomic DNA was prepared 72 hours post-transfection using the Qiagen DNEASY kit using the manufacturer protocol. PCR was conducted on 250 ng of genomic DNA with primers target the integration junction. Products were resolved on a 2% agarose.

k. Sequencing of Deletion and Integration Products

Following gel resolution of amplicons, deletion bands were gel-extracted using the Gen Elute gel extraction kit (Sigma-Aldrich) using the manufacturer's protocol. Following extraction, products with phosphorylated via incubation in 50 μl reactions with T4 PNK and 1× T4 DNA ligase buffer. Reactions were heat inactivated and ligated in equimolar ratio to SmaI cleaved and dephosphorylated pUC19. Ligations were transformed into chemically competent NEB10B *E. coli* and plated on Ampicillin Plates supplemented with 40 μl X-Gal solution (Promega). White colonies were picked and prepared using GeneElute Plasmid Preparation kit (Sigma-Aldrich). 300 ng of plasmid DNA was sequenced via DNASU's Sanger Sequencing Core facility.

2. Design of iCas9 and Guide Sequences for RNA-Guided Targeting of iCas9

The design of iCas9 followed several general principles. First, the fusion of catalytically inactive Cas9 (dCas9) with a hyperactive mutant TN3 resolvase (mTN3) was accomplished by addition of the N-terminal resolvase catalytic domain to the N-terminus of dCas9 (FIG. 1A). These domains were separated by a flexible glycine serine (GGSx6) linker. To facilitate nuclear entry, SV40 nuclear localization sequences (NLS) were added on both the N- and C-termini. The choice of mTN3 was motivated by previous studies that showed mTN3 zinc finger fusions were capable of DNA deletion and integration (FIG. 1B). Finally, previous work demonstrated FokI-dCas9 fusion proteins dimerize when pairs of sgRNAs were targeted in a PAM-distal orientation. This suggested that mTN3's N-terminal heterologous fusion with dCas9 are presented adjacent to the 5' end of the sgRNA bound to a protospacer DNA. Furthermore, solved protein structures for *Streptococcus pyogenes* Cas9 place the N-terminus closer to the 5' end of the sgRNA than the C-terminus. Collectively, structural information and previous FokI-dCas9 results strongly suggest that a PAM-distal protospacer orientation flanking a mTN3 core recognition site should enable RNA-guided targeting (FIG. 1C).

3. Validation Using Yeast

Figure 2A:
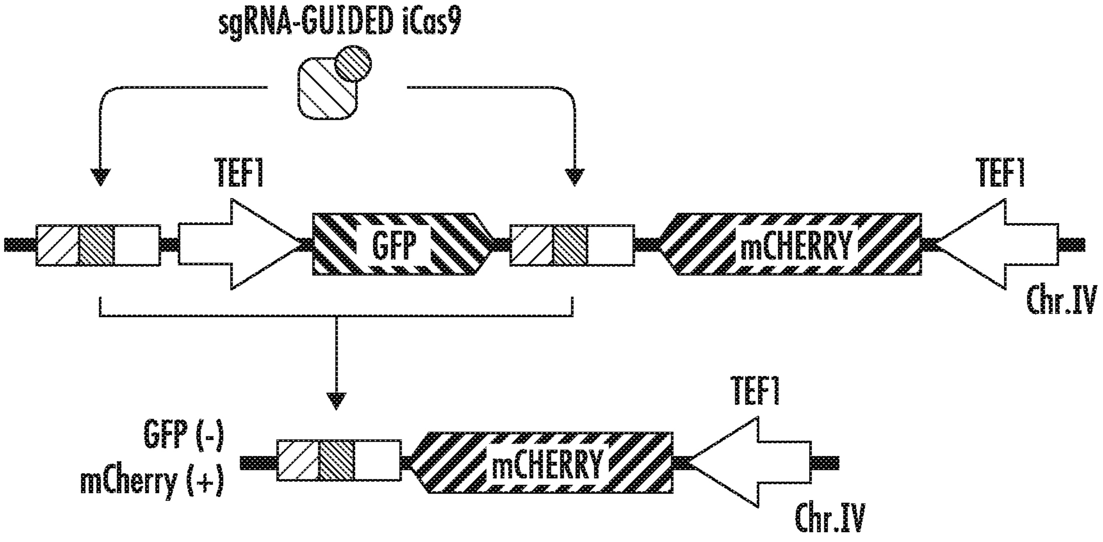
Figure 2B:
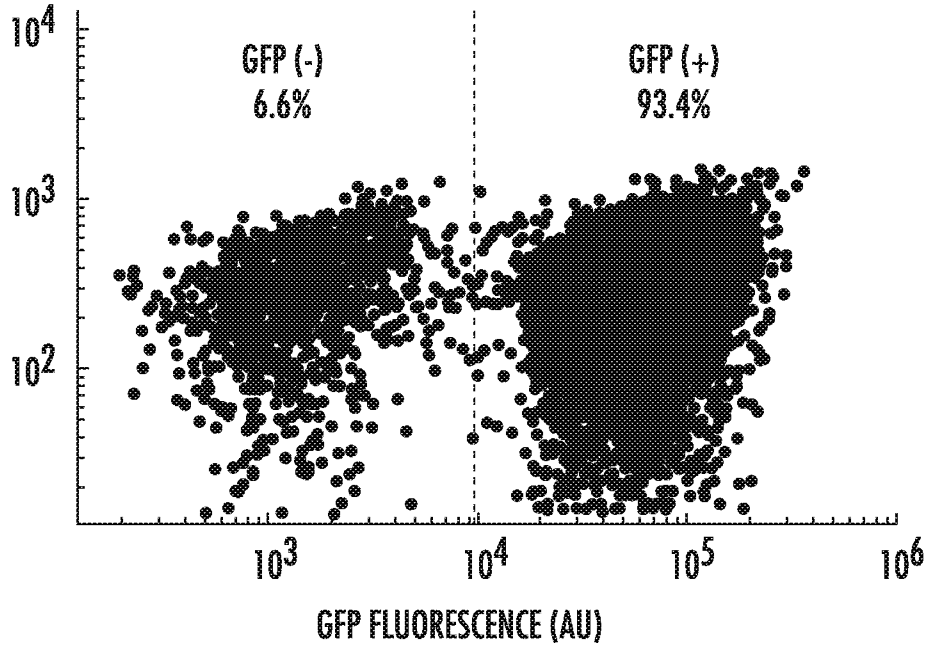
Figure 2C:
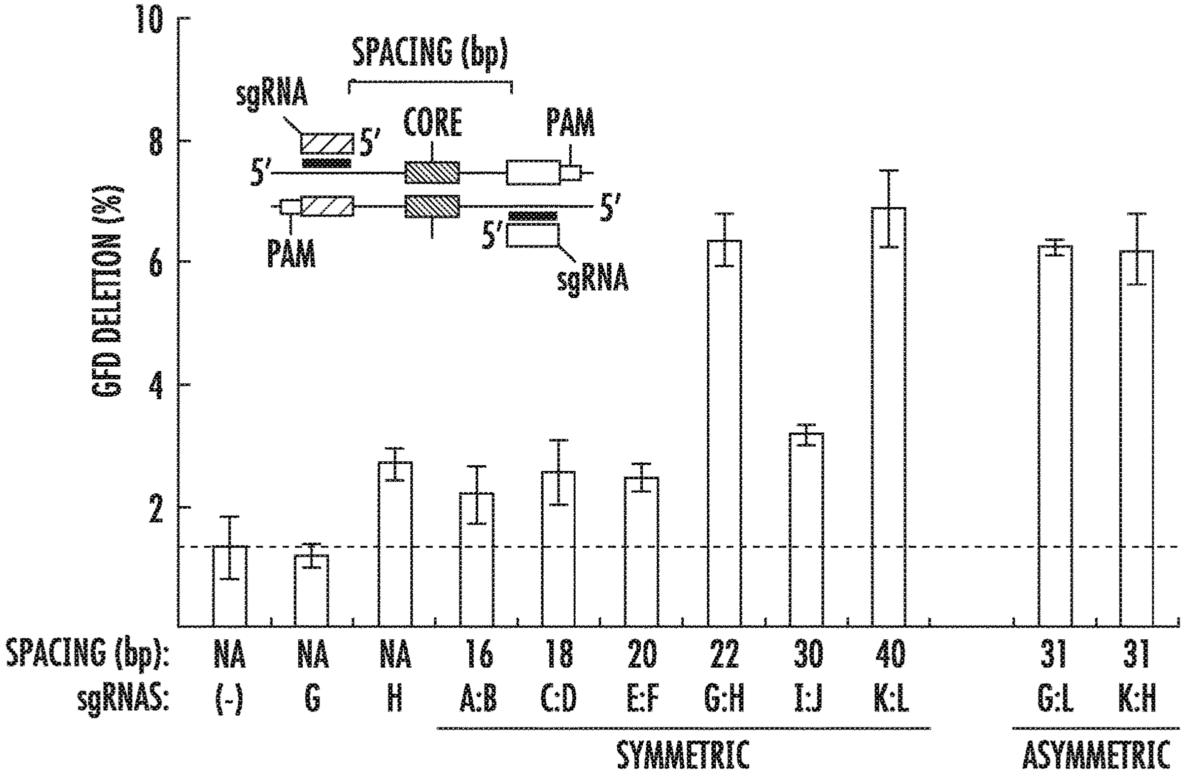
Figure 7:
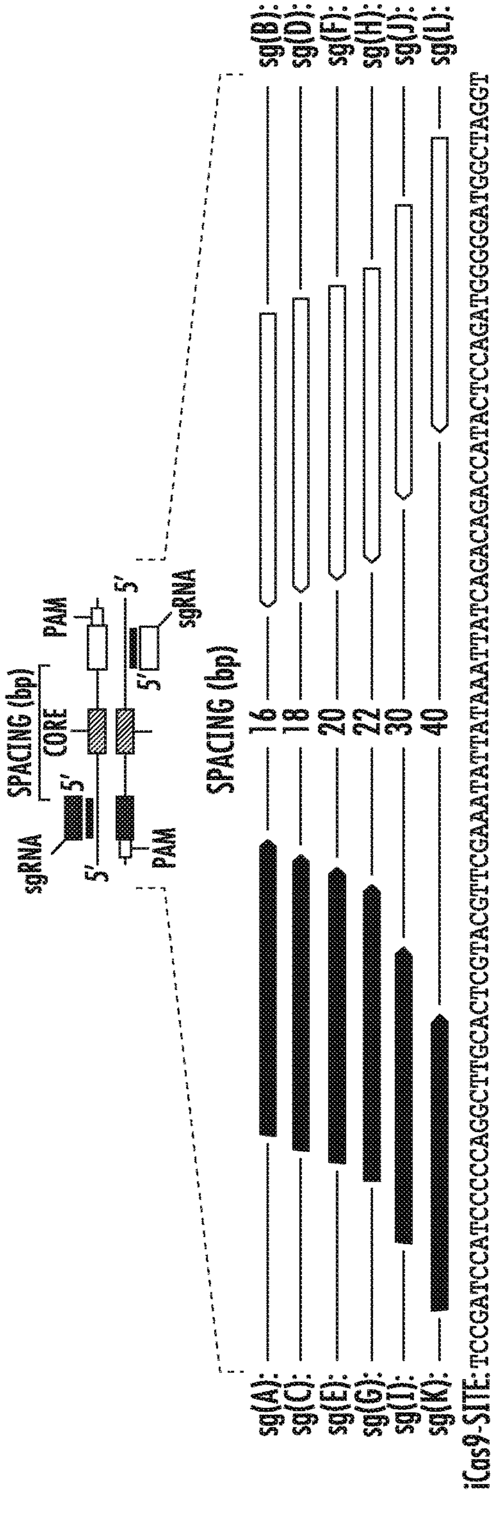
FIG. 7 depicts, in accordance with certain embodiments, an iCas9-Site Design. Target sequence for iCas9 consists of a core TN3 Res1 sequence combined with randomized sequence with multiple protospacer adjacent motifs (PAMs) flanking. These enabled systematic spacing of sgRNA pairs. Icons indicate positioning of left (filled) and right (not shaded) sgRNA targets. (for specific iCas9-site and sgRNA sequences see supplemental sequences).

To develop an iCas9 capable of targeting eukaryotic genomic DNA, a yeast-based fluorescent reporter system was used to detect recombination. A *Saccharomyces cerevisiae* dual-fluorescent recombination reporter system, which contains GFP and mCherry expression cassettes was constructed and enabled detection of recombination using flow cytometry and fluorescence microscopy. Both GFP and mCherry were constitutively expressed from translation elongation factor 1 (Tef1) promoters. GFP was flanked by TN3 Res1 core sequences and resulted in GFP deletion upon iCas9 targeting. (FIG. 2A and FIGS. 6A-6D). Each core sequence was flanked with numerous PAMs, which enabled systematic analysis of sgRNA spacings (FIG. 7). iCas9 was placed on a yeast Cen6 vector with galactose inducible promoter and sgRNAs were placed on a yeast 2p vector with SNR52 promoters (FIGS. 6A-6D). Co-expression of iCas9 along with targeting sgRNA pairs resulted in loss-of-GFP detectable by flow cytometry (FIG. 2B). Single targeting with sgRNAs did not result in marked GFP-deletion (FIG. 2C). The observed requirement of cooperative targeting by sgRNAs matches mTN3's dimerization dependent function. sgRNA spacing's from 16 bp to 40 bp were analyzed. Symmetric spacing's of 22 bp and 40 bp were functional and resulted in 6.4±0.4% and 6.9±0.6% GFP-deletion respectively. However, 30 bp spacing symmetrically placed around the core sequence remained relatively non-functional while asymmetric spacing's of 31 bp around the core are functional (FIG. 2C). The observed functional spacing's are consistent with the requirement for targeting resolvase monomers to the same DNA helical face (See FIG. 8).

Figure 2D:
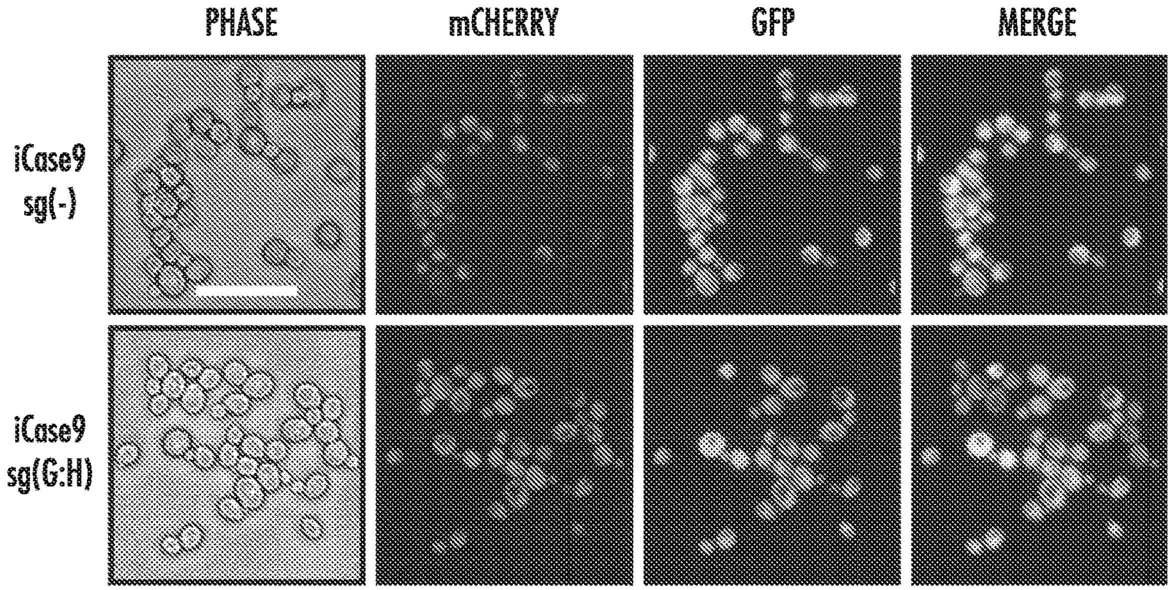

To confirm loss-of-GFP was due to GFP-deletion and not the result of spurious cell death or non-specific recombination, fluorescence microscopy was used to detect GFP and mCherry expression. All cells with a non-target guide, sg(−), expressed both GFP and mCherry. However, cooperative targeting with sgRNA pairs resulted in GFP-negative cells with intact mCherry expression (FIG. 2D). Recombination occurred on the DNA level by PCR with primers flanking the GFP and mCherry expression cassettes. The starting reporter resulted in a 5 Kb PCR product GFP-deletion generated a 4 Kb amplicon. The deletion product formed when iCas9 was co-expressed with sgRNA pairs, sg(G:H); however, no deletion product formed when iCas9 was co-expressed with sg(−). This indicates iCas9 targets DNA-deletion and its function is dependent on RNA-guidance (FIG. 2E). DSB-targeted DNA-deletion result in indel mutations. However, iCas9-mediated DNA-deletion should be free of mutations. To further characterize deletion products, the 4 Kb deletion amplicons were isolated, sub-cloned, and Sanger sequenced, and no indel mutations within the recombination product was observed (FIG. 2F). This further suggests the utility of iCas9 in mediating error-free DNA recombination.

Figure 9A:
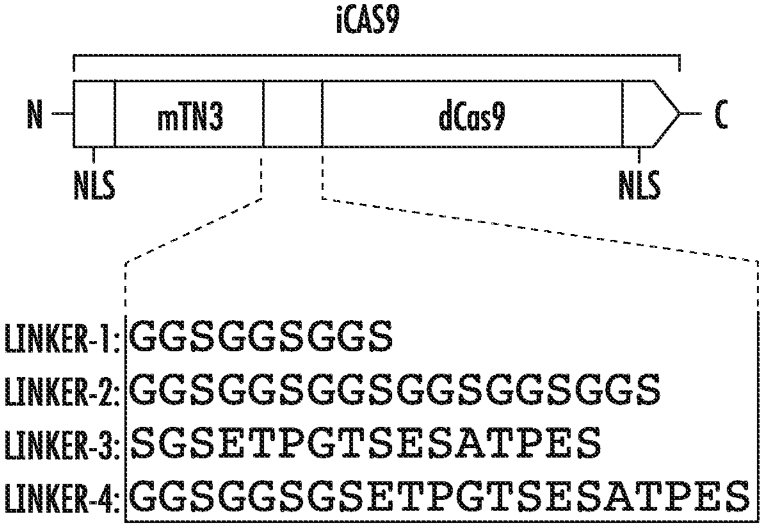
FIGS. 9A-9B depict, in accordance with certain embodiments, the effect of interdomain linkers on iCas9 function.
Figure 9B:
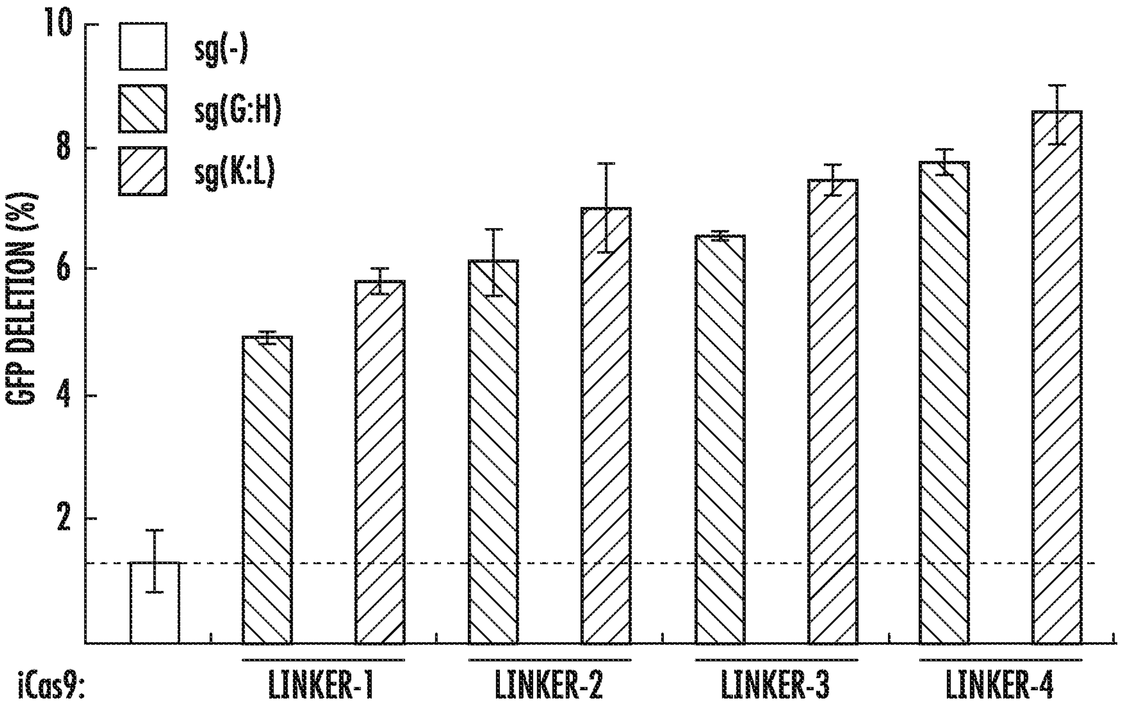

Aiming to improve iCas9 function, the effect of interdomain linker amino acid sequences was tested. These sequences included a range of flexible glycine serine and rigid linkers. Linker-3 was a common and effective linker used with Cas9 heterologous fusion proteins. Only subtle preference was observed for longer linker domains; however, these do not result in vivid improvement of iCas9 function (FIG. 9B). Henceforth, mTN3-(GGS)x6-dCas9 was used for further studies and referred to herein as "iCas9," as its function has been extensively characterized in the yeast-based assays.

4. Validation in Human Cells

Figure 3A:
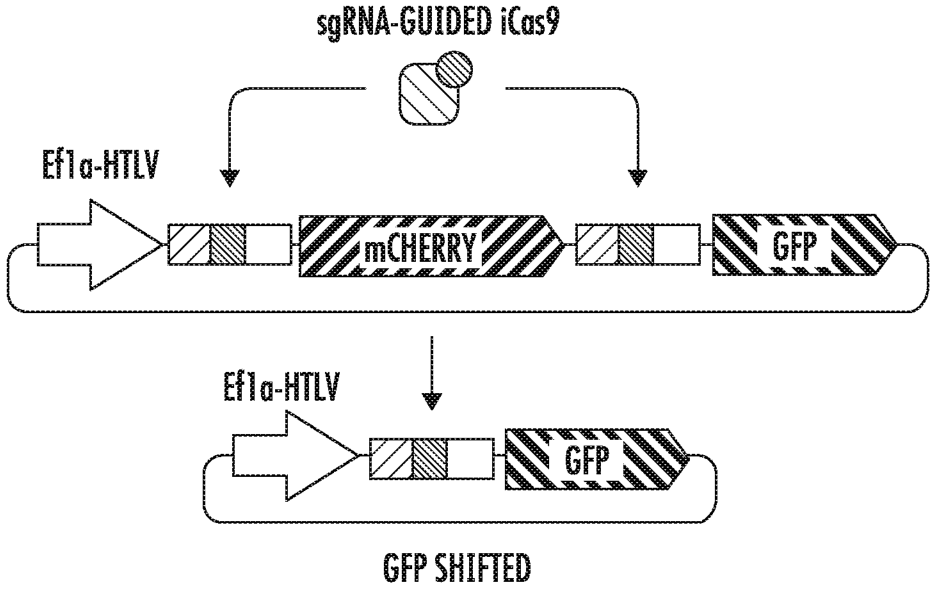
FIGS. 3A-3B depict, in accordance with certain embodiments, the detection of iCas9 function using an episomal deletion assay in human cells.
Figure 3B:
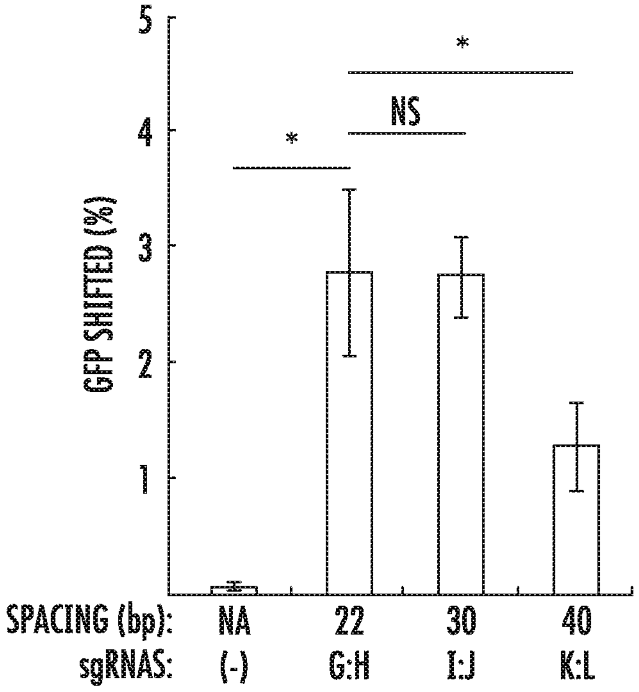
Figure 10A:
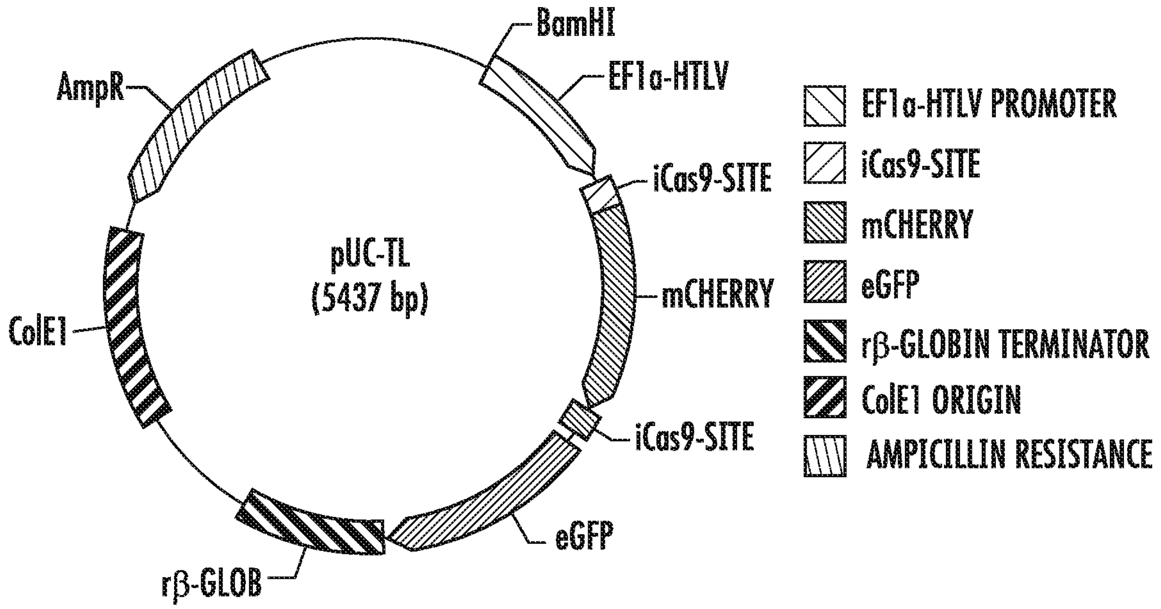
FIGS. 10A-10F depict, in accordance with certain embodiments, human cell reporter iCas9 and sgRNA Vectors.

To assess the function of iCas9 in human cells, a dual-fluorescence detection plasmid-based reporter was developed. The reporter plasmid contained mCherry flanked by core recognition sites with GFP downstream (FIG. 3A, FIG. 10A). Therefore, mCherry deletion should result in cells expressing GFP only. Under this scenario, GFP expression remains relatively constant, while mCherry levels go to zero, yielding a population of cells with GFP levels shifted over mCherry. HEK293T cells was co-transfected with dual-reporter, sgRNA and iCas9 expression vectors while gating out untransfected cells. The shift of cells with GFP over mCherry expression was quantified using flow cytometry and analyzed to evaluate sgRNA spacings for our plasmid targeting assay. Interestingly 22, 30 and 40 bp shifted GFP expression, while a non-target guide, sg(−), resulted in no GFP shift. These results indicated both 22 and 30 bp are comparably functional when targeting plasmid substrates (FIG. 3B). Previous work with Gin-dCas9 fusions have reported the ability for 30 bp sgRNA spacing to target DNA deletion on plasmid substrates. This may be due to the use of supercoiled plasmids as substrates, which may support less stringent spacing requirements due to DNA coiling and 3D presentation. Nevertheless, 22 bp remained a highly functional sgRNA spacing and henceforth used since it is active in both plasmid and genomic assays.

Figure 4A:
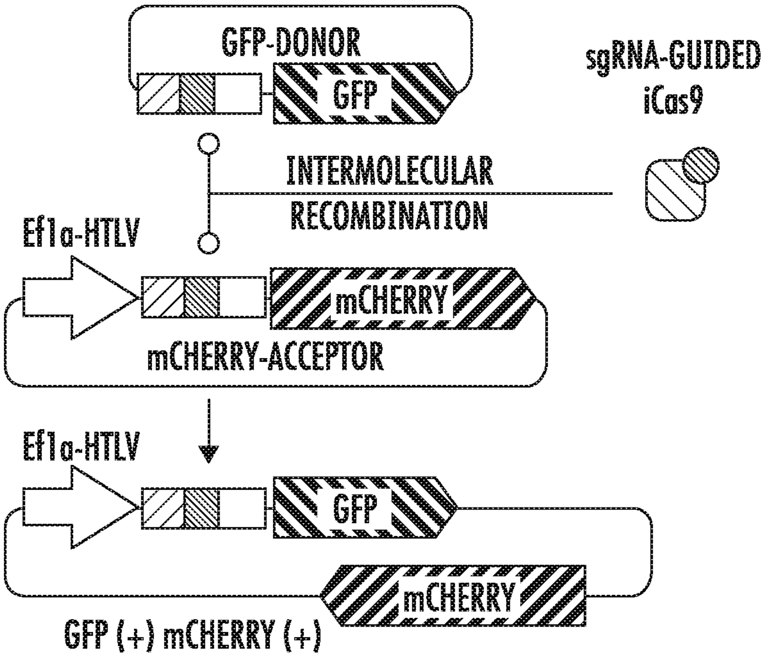
FIGS. 4A-4D depict, in accordance with certain embodiments, iCas9-targeted plasmid-to-plasmid recombination in human cells.
Figure 4B:
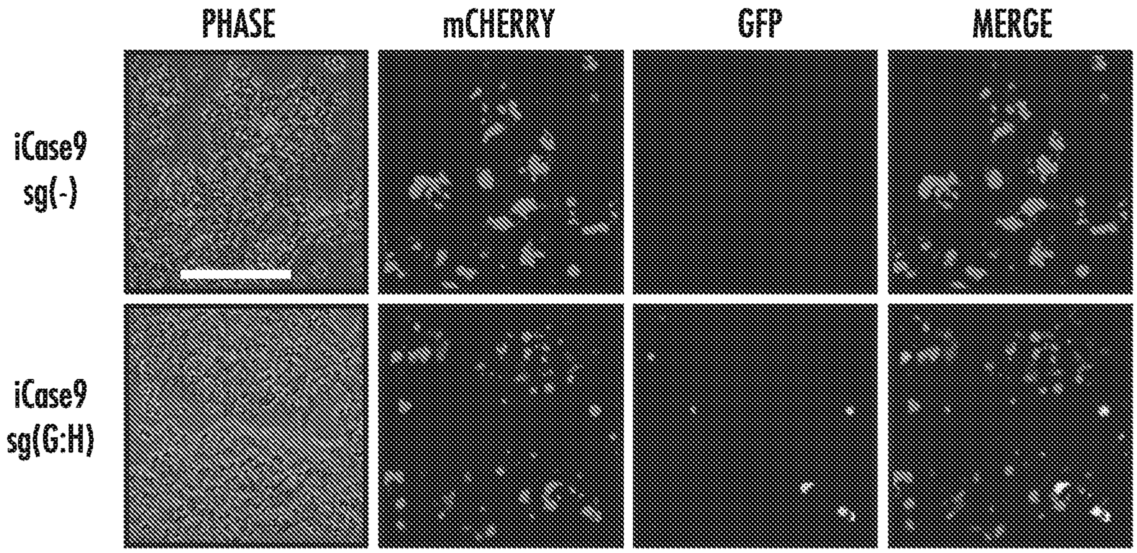
Figure 4C:
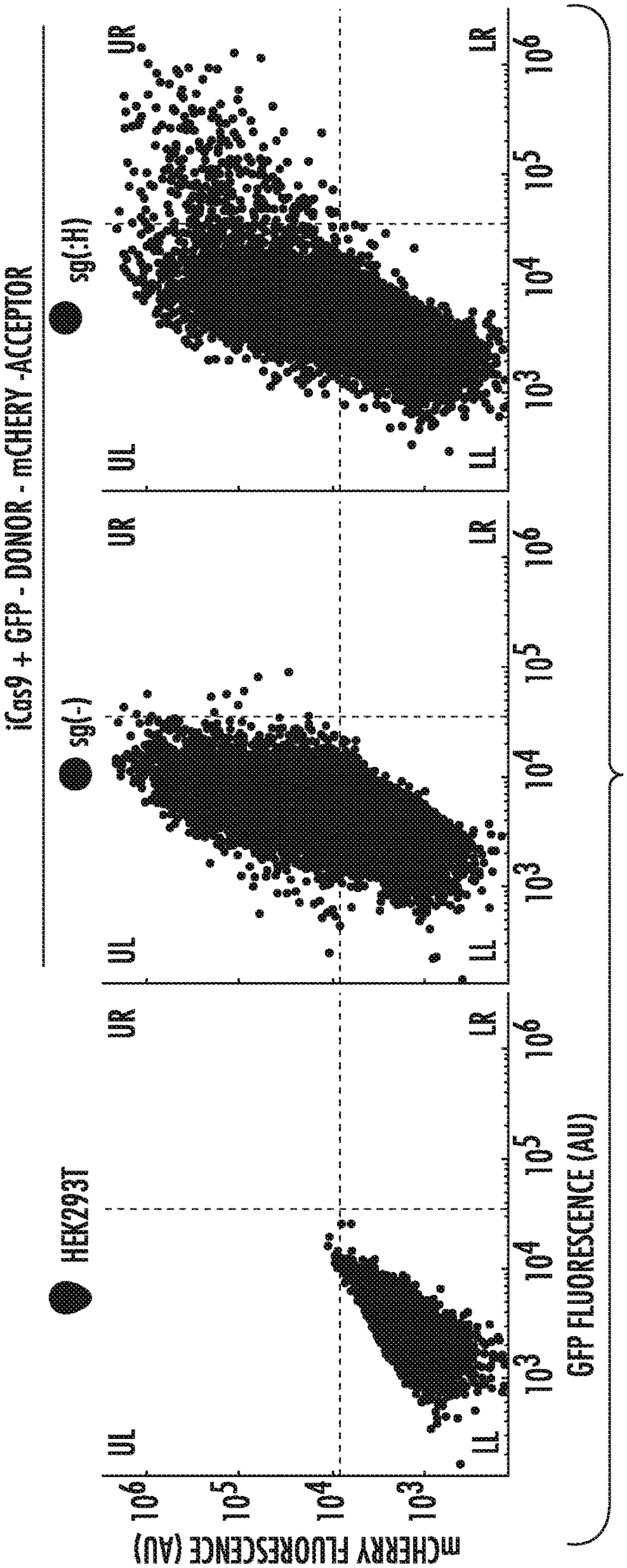
Figure 4D:
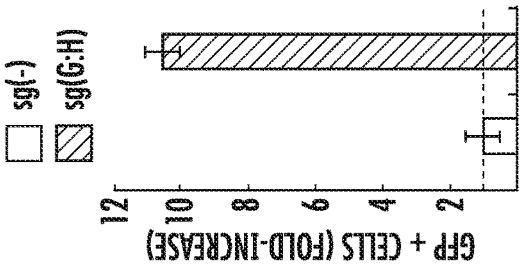
Figure 10B:
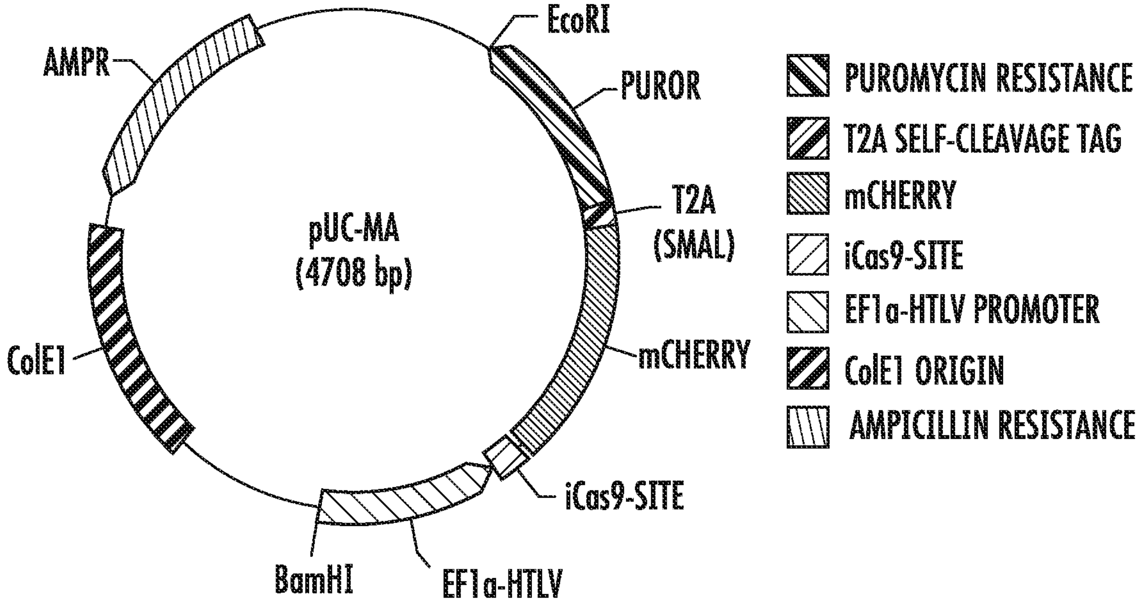
Figure 10C:
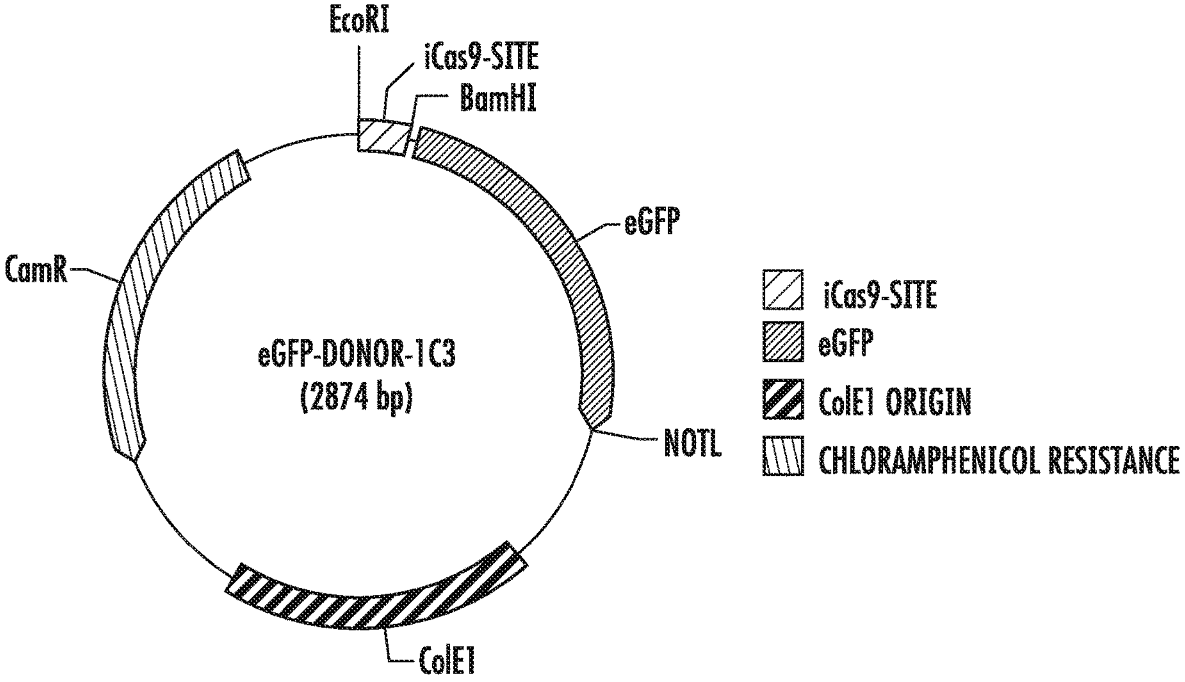

Next to determine iCas9's ability to target intermolecular recombination, a two-plasmid reporter system for plasmid-to-plasmid integration was developed. One plasmid contains an elongation factor 1α (EF1α) human T-cell leukemia virus (HTLV) hybrid promoter, and a core target site upstream of a mCherry coding region. A second promoterless GFP-donor plasmid contains a core target sequence upstream of a GFP reading frame (FIGS. 10B and 10C). The GFP-donor plasmid conditionally expressed upon integration downstream of the EF1α-HTLV promoter resulted in dual-GFP and mCherry positive cells (FIG. 4A). GFP expression as detected by flow cytometry and fluorescence microscopy was used as an indicator of recombination efficiency. Co-transfection of iCas9 and a non-target guide control resulted in only mCherry expressing cells, however, targeting with sgRNAs at a 22 bp spacing resulted in GFP-positive cells (FIG. 4B). Flow cytometry measurements confirm the generation of mCherry-GFP dual-positive cells when targeting iCas9 with sg(G:H) (FIGS. 4C and 4D).

Figure 5A:
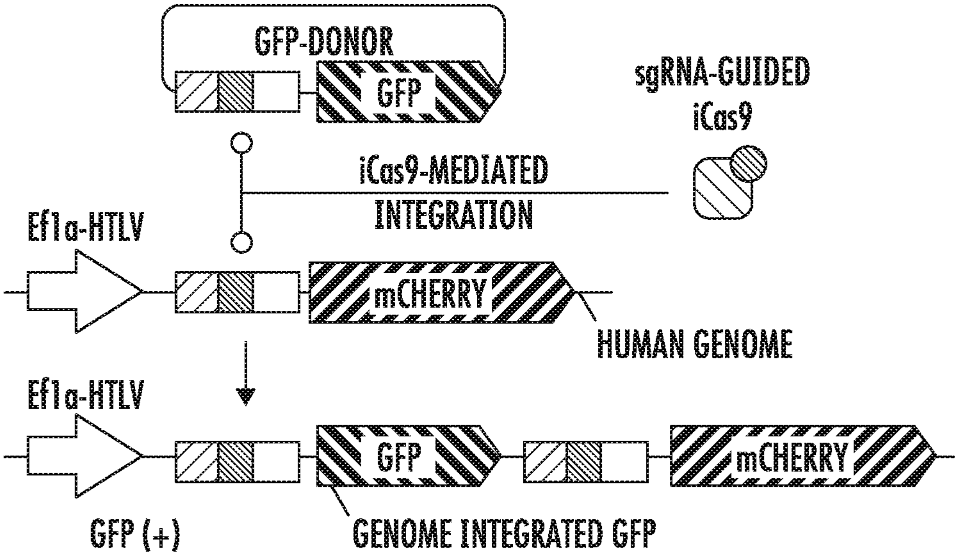
Figure 10D:
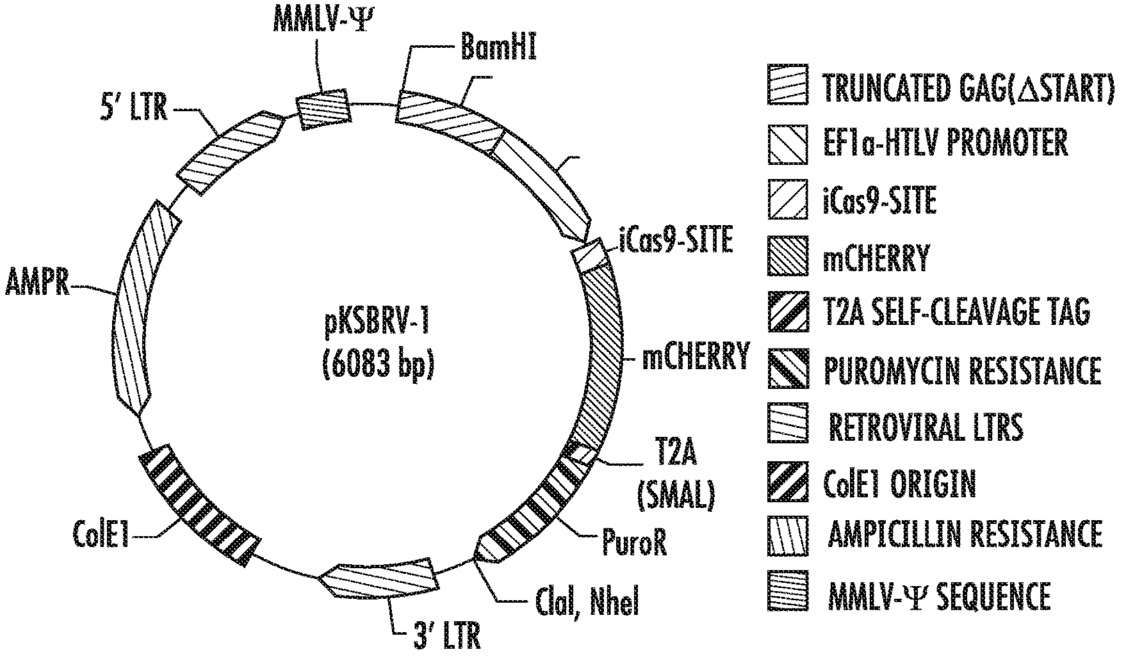
Figure 10E:
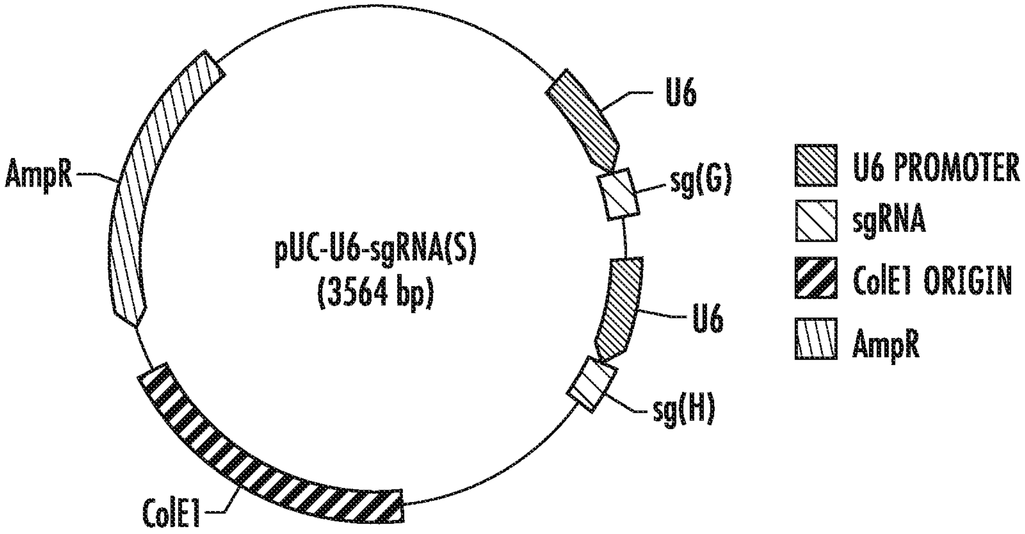
Figure 10F:
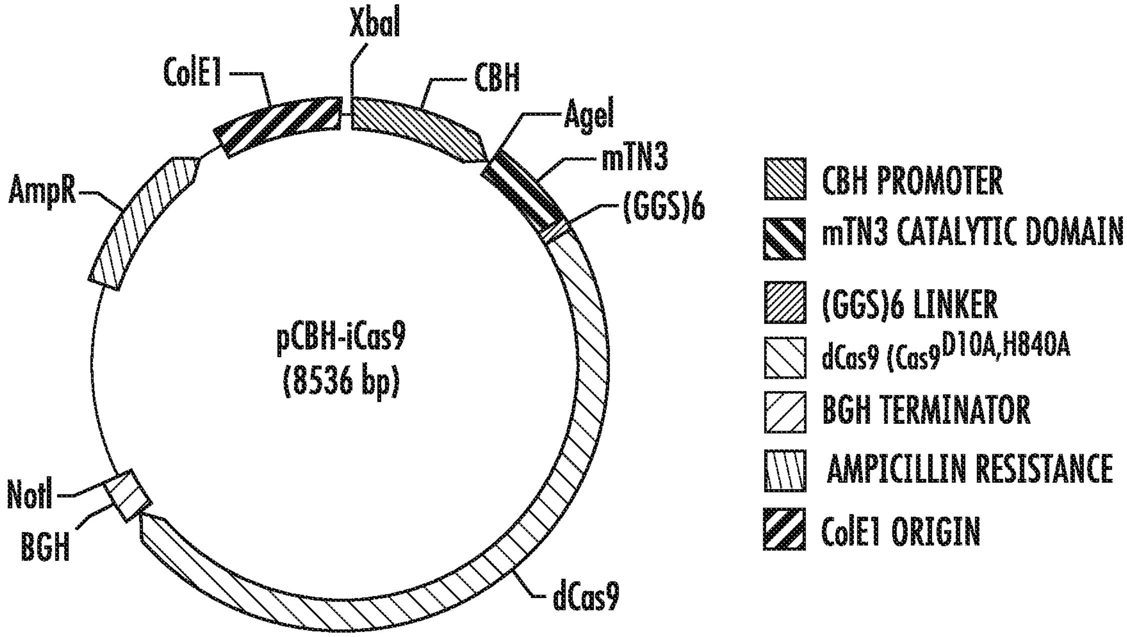
Figure 11:
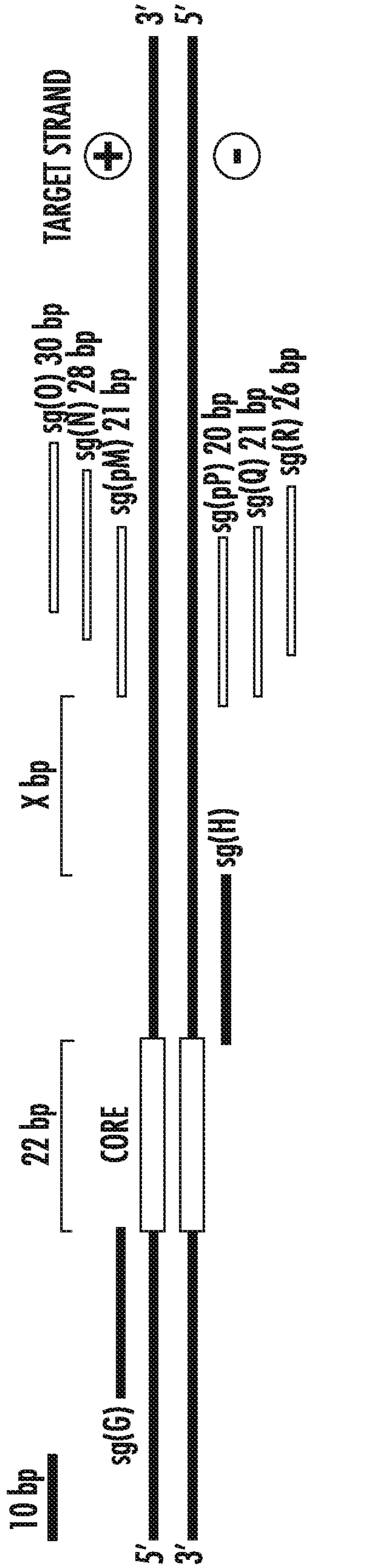
FIG. 11: Design of Accessory sgRNAs. Accessory sgRNAs as targeting the genomic reporter locus (blue) were targeted to the + or − strand at varying bp distances from sg(H) (X bp). Distances are listed by each guide. Targeted strand is that which is complementary to the guide sequence.

To determine if iCas9 can mediate plasmid-to-genome integration, the plasmid-based assay was adapted to detect genome integration (FIG. 5A). To accomplish this, the mCherry acceptor cassette was placed on a retroviral vector (FIG. 10D). HEK293 Ts were transduced with viral particles containing the 'acceptor-cassette'. This generated a population of cells with the mCherry acceptor cassette integrated into the genome. HEK293 Ts were then transfected cells with iCas9, sgRNA(s) and GFP-Donor vector. In the first attempts, no increase in GFP+ cells in sg(G:H) were observed over a control guide, sg(−) (FIG. 5C). Even with validated plasmid-to-plasmid recombination, when the same 'acceptor' sequence is placed in the genome, no recombination was observed. iCas9 was verified to be capable of targeting both donor and acceptor sequences (FIG. 4); however this did not result in genome integration. This may be due to the inability of iCas9-bound GFP-donor plasmids to interact with the genomic acceptor locus.

Figure 5B:
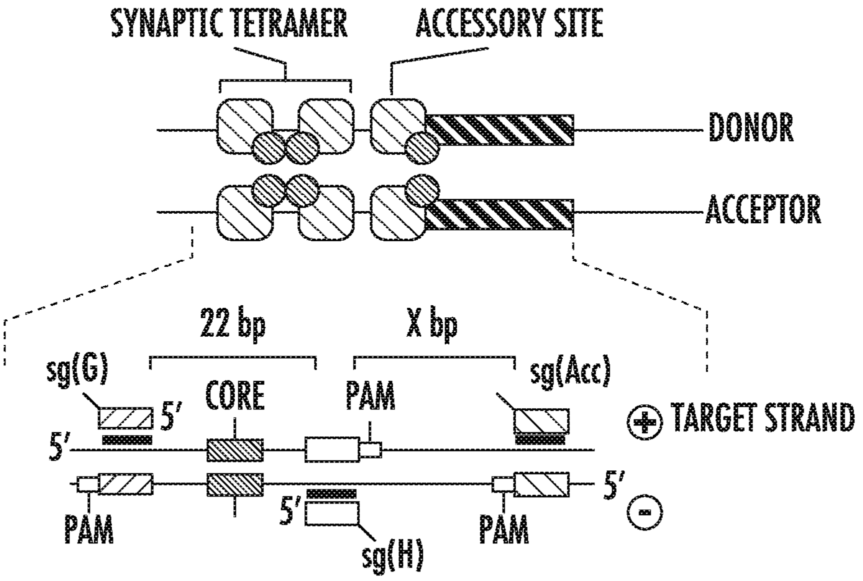
Figure 6A:
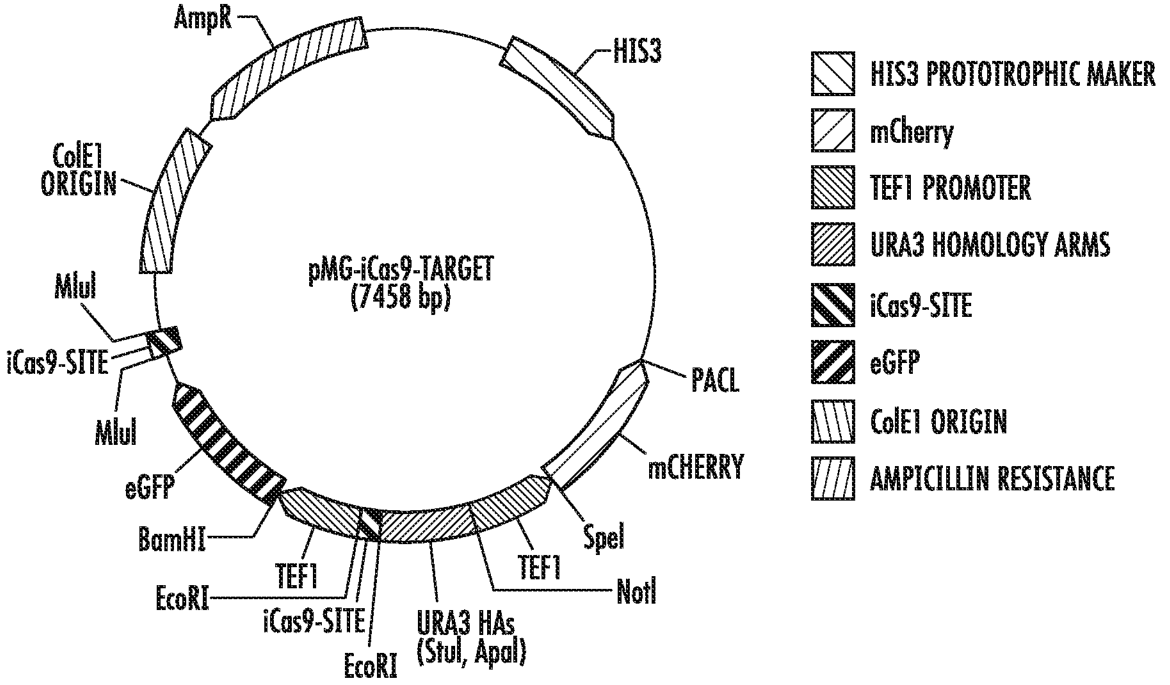
FIGS. 6A-6D depict, in accordance with certain embodiments, *S. cerevisiae* Reporter iCas9 and sgRNA vectors.
Figure 6B:
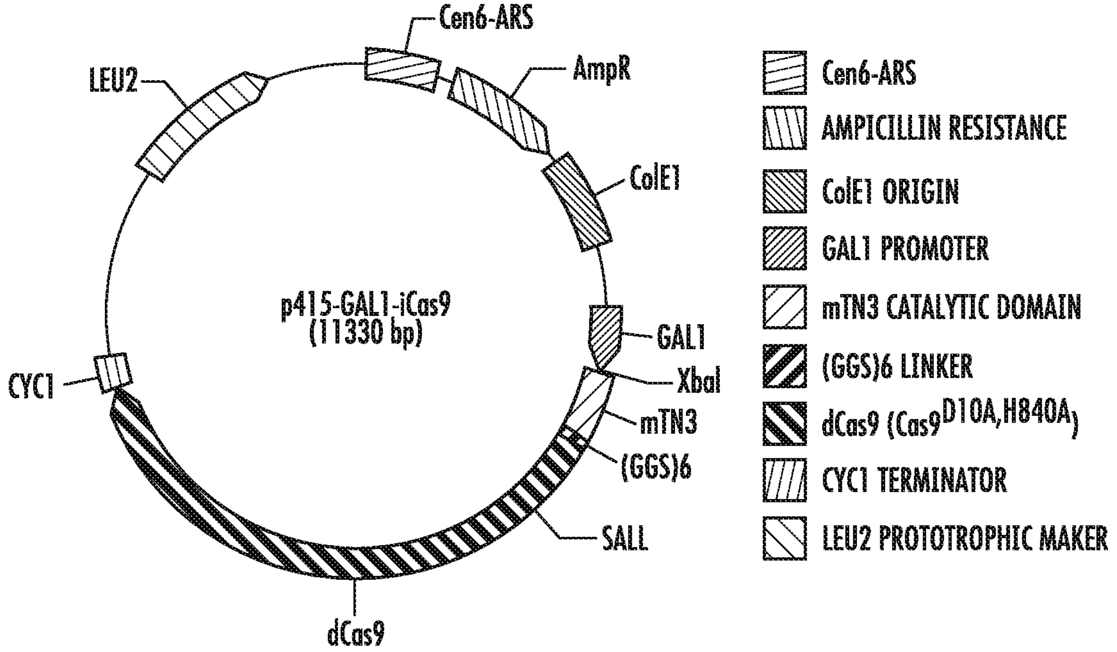
Figure 6C:
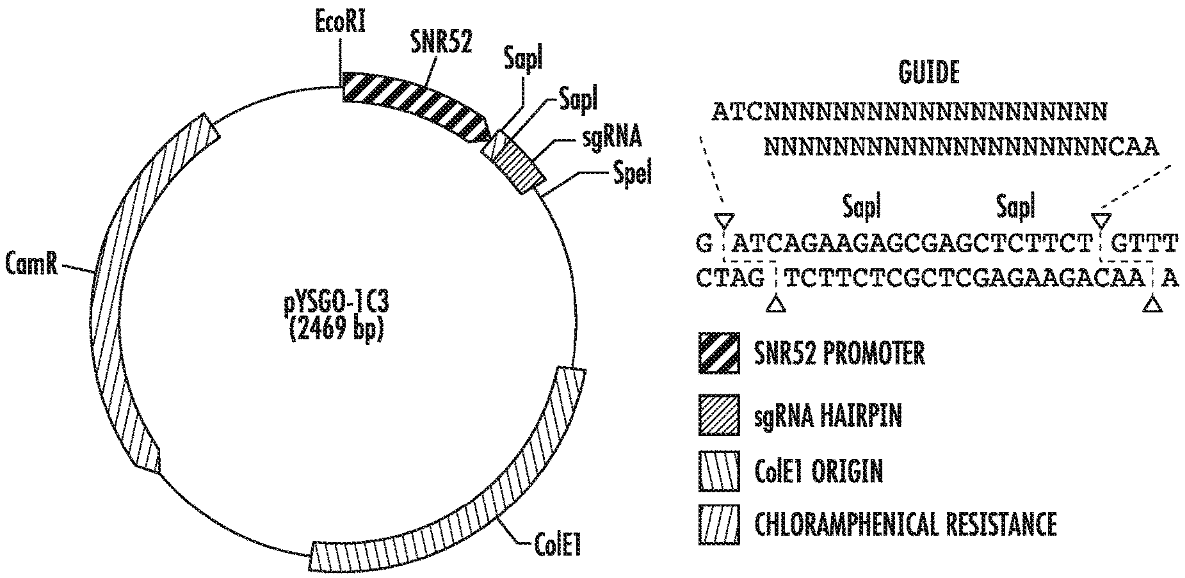
Figure 6D:
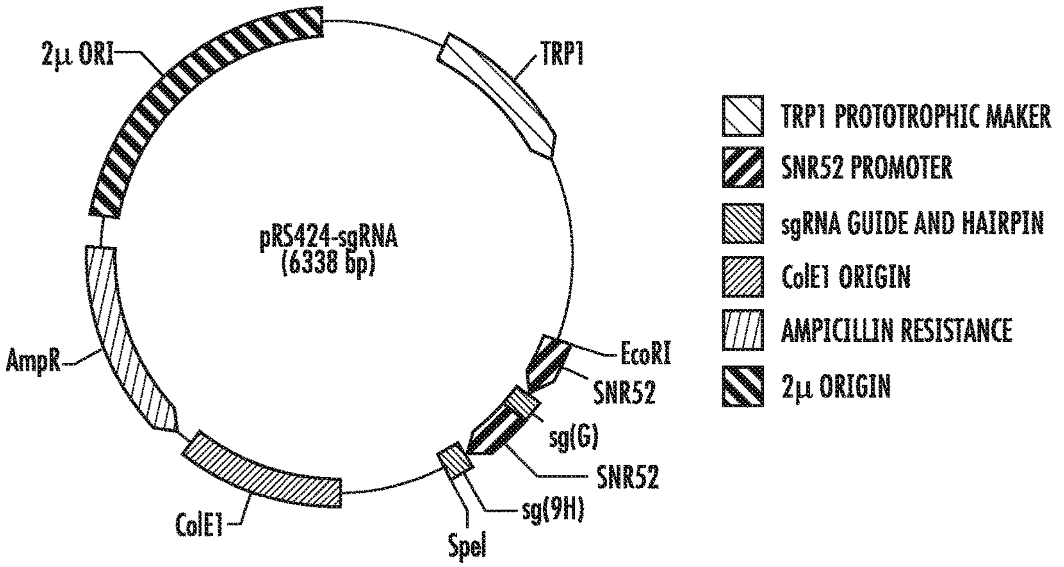

Given iCas9's ability to mediate plasmid-to-plasmid but not plasmid-to-genome recombination, cooperative targeting may be necessary to enable genomic integration. Bacterial TN3 resolvase uses cooperative binding at accessory sites to ensure efficient recombination of cointegrate products, where TN3 resolvase coordinates substrate DNA bending, supercoiling and 3D positioning. Multiplex sgRNAs targeting can recreate accessory site binding, which should allow for extra mTN3 domains to coordinate interaction between GFP-donor and the acceptor locus. To test this, a series of sgRNAs adjacent to the target core sites were designed. These sgRNAs were targeted to either the '+' or '−' strand at varying base pair distances from the core target site (FIG. 5B, Supplemental FIG. 6). These accessory guides were co-transfected with sg(G:H), GFP-donor and iCas9 into the mCherry-acceptor line. A 10-fold increase in the number of GFP+ cells over the control guide was observed when targeting with accessory sg(M) (FIG. 5C). The recombination product was further characterized via PCR with primers flanking the integration junction. Integration of GFP into the acceptor locus was detected when targeting with sg(G), (H) and (M) (multiplex-targeting) (FIG. 5D). To further confirm the identity of this amplicon, the recombination product was subcloned and sequenced. Importantly, sequencing indicated the recombination product was free of unwanted indel mutations (FIG. 5E). On the other hand, targeting DNA integration using DSBs created by wildtype Cas9 induced indel mutations (FIG. 5F), which could be detrimental for many downstream applications.

5. Sequences Used

Table 1 lists the sgRNA guide sequences, and Table 2 lists the primers and oligonucleotides used.

TABLE 1

| Host: | Letter: | Guide Sequence: | Note: | SEQ ID NO. |
|---|---|---|---|---|
| Yeast | (-) | AGAAGAGCGAGCTCTTCT | Control, non-target | 3 |
| Yeast | A | CGAACGTACGAGTGCAAGCC | 16 bp spacing left | 4 |
| Yeast | C | GAACGTACGAGTGCAAGCCT | 18 bp spacing left | 5 |
| Yeast | E | AACGTACGAGTGCAAGCCTG | 20 bp spacing left | 6 |
| Yeast | G | ACGTACGAGTGCAAGCCTGG | 22 bp spacing left | 7 |
| Yeast | I | ACGAGTGCAAGCCTGGGGGA | 30 bp spacing left | 8 |
| Yeast | K | TGCAAGCCTGGGGGATGGAT | 40 bp spacing left | 9 |
| Yeast | B | CAGACAGACCATACTCCAGA | 16 bp spacing right | 10 |
| Yeast | D | AGACAGACCATACTCCAGAT | 18 bp spacing right | 11 |
| Yeast | F | GACAGACCATACTCCAGATG | 20 bp spacing right | 12 |
| Yeast | H | ACAGACCATACTCCAGATGG | 22 bp spacing right | 13 |
| Yeast | J | ACCATACTCCAGATGGGGGA | 30 bp spacing right | 14 |
| Yeast | L | ACTCCAGATGGGGGATGGCT | 40 bp spacing right | 15 |
| Human | (-) | GGGTCTTCGAGAAGACCT | Control, non-target | 16 |
| Human | G | GACGTACGAGTGCAAGCCTGG | 22 bp spacing left | 17 |
| Human | H | GACAGACCTTACTCCAGAAGG | 22 bp spacing right | 18 |
| Human | K | GTGCAAGCCTGGGGGAAGGAT | 40 bp spacing left | 19 |
| Human | L | GACTCCAGAAGGGGGAAGGCT | 40 bp spacing right | 20 |
| Human | I | GACGAGTGCAAGCCTGGGGGA | 30 bp spacing left | 21 |
| Human | J | GACCTTACTCCAGAAGGGGGA | 30 bp spacing right | 22 |
| Human | M | GTTGCTCACCATGGTGGCGAC | Accessory, +21 bp | 23 |
| Human | N | GCTCGCCCTTGCTCACCATGG | Accessory, +28 bp | 24 |
| Human | O | GCTCCTCGCCCTTGCTCACCA | Accessory, +31 bp | 25 |
| Human | P | GGTCGCCACCATGGTGAGCA | Accessory, -20 bp | 26 |
| Human | Q | GTCGCCACCATGGTGAGCAA | Accessory, -21 bp | 27 |
| Human | R | GCACCATGGTGAGCAAGGGCG | Accessory, -26 bp | 28 |

TABLE 2

| Primer | Sequence | Note: | SEQ ID NO. |
|---|---|---|---|
| 1 | CGCATATGTGGTGTTGAAGA | Yeast URA3 PCR F | 29 |
| 2 | CTAGGGCTTTCTGCTCTGTCAT | Yeast HIS3 PCR R | 30 |
| 3 | TGGAGGGCACAGTTAAGCCG | Yeast URA3 PCR F-2 | 31 |
| 4 | AATACCGCCTTTGAGTGAGC | Standard vector PCR/Seq. R | 32 |

TABLE 2-continued

| Primer | Sequence | Note: | SEQ ID NO. |
|---|---|---|---|
| 5 | AGCTGTGACCGGCGCCTACG | Human EF1α-HTLV PCR F | 33 |
| 6 | CTGAGCACCCAGTCCGCCCTGAG | Human eGFP R | 34 |
| 7 | AATTCTCCGATCCATCCCCCAGGCTTG CACTCGTACGTTCGAAATAT | Yeast iCas9-site EcoRI-end Top 1 | 35 |
| 8 | ATAATATTTCGAACGTACGAGTGCAA GCCTGGGGGATGGATCGGAG | Yeast iCas9-site EcoRI-end Bottom 1 | 36 |
| 9 | TATAAATTATCAGACAGACCATACTC CAGATGGGGGATGGCTAGGTG | Yeast iCas9-site EcoRI-end Top 2 | 37 |
| 10 | AATTCACCTAGCCATCCCCCATCTGGA GTATGGTCTGTCTGATAATTT | Yeast iCas9-site EcoRI-end Bottom 2 | 38 |
| 11 | CGCGTTCCGATCCATCCCCCAGGCTTG CACTCGTACGTTCGAAATAT | Yeast iCas9-site MluI-end Top 1 | 39 |
| 12 | ATAATATTTCGAACGTACGAGTGCAA GCCTGGGGGATGGATCGGAA | Yeast iCas9-site MluI-end Bottom 1 | 40 |
| 13 | TATAAATTATCAGACAGACCATACTC CAGATGGGGGATGGCTAGGTA | Yeast iCas9-site Mlu-endI Top 2 | 41 |
| 14 | CGCGTACCTAGCCATCCCCCATCTGG AGTATGGTCTGTCTGATAATTT | Yeast iCas9-site MluI-end Bottom 2 | 42 |
| 15 | AATTCTCCGATCCTTCCCCCAGGCTTG CACTCGTACGTTCGAAATAT | Human iCas9-site EcoRI-end Top 1 | 43 |
| 16 | CTCCGATCCTTCCCCCAGGCTTGCACT CGTACGTTCGAAATAT | Human iCas9-site Blunt-end Top 1 | 44 |
| 17 | ATAATATTTCGAACGTACGAGTGCAA GCCTGGGGGAAGGATCGGAG | Human iCas9-site Bottom 1 | 45 |
| 18 | TATAAATTATCAGACAGACCTTACTCC AGAAGGGGGAAGGCTAGGTG | Human iCas9-site Top 1 | 46 |
| 19 | GATCCACCTAGCCTTCCCCCTTCTGGA GTAAGGTCTGTCTGATAATTT | Human iCas9-site BamHI-end Bottom 2 | 47 |
| 20 | CACCTAGCCTTCCCCCTTCTGGAGTAA GGTCTGTCTGATAATTT | Human iCas9-site Blunt-end Bottom 2 | 48 |
| 21 | AGAACAGTTGATAGAGGAGGGAGCG GGGGAAGCGGTGGCTCA | Linker-1 Oligo Top | 49 |
| 22 | CATTGAGCCACCGCTTCCCCCGCTCCC TCCTCTATCAACTGT | Linker-1 Oligo Bottom | 50 |
| 23 | AGAACTGTTGACCGAGGTGGTTCAGG AGGAAGTGGA | Linker-2 Oligo Top 1 | 51 |
| 24 | ACCTCCACTTCCTCCTGAACCACCTCG GTCAACAGT | Linker-2 Oligo Bottom 1 | 52 |
| 25 | GGTTCAGGGGGAAGTGGTGGCTCCGG TGGGTCT | Linker-2 Oligo Top 2 | 53 |
| 26 | CATAGACCCACCGGAGCCACCACTTC CCCCTGA | Linker-2 Oligo Bottom 2 | 54 |
| 27 | AGAACAGTTGATCGGAGCGGTTCTGA GACT | Linker-3 Oligo Top 1 | 55 |
| 28 | CGGAGTCTCAGAACCGCTCCGATCAA CTGT | Linker-3 Oligo Bottom 1 | 56 |
| 29 | CCGGGAACCTCAGAGTCTGCTACGCC GGAAAGC | Linker-3 Oligo Top 2 | 57 |

TABLE 2-continued

| Primer | Sequence | Note: | SEQ ID NO. |
|---|---|---|---|
| 30 | CATGCTTTCCGGCGTAGCAGACTCTG AGGTTCC | Linker-3 Oligo Bottom 2 | 58 |
| 31 | AGAACCGTAGATCGCGGGGGCTCTGG AGGATCAGGTA | Linker-4 Oligo Top 1 | 59 |
| 32 | CGCTACCTGATCCTCCAGAGCCCCCG CGATCTACGGT | Linker-4 Oligo Bottom 1 | 60 |
| 33 | GCGAAACGCCGGGTACTAGCGAAAGC GCGACACCTGAGAGT | Linker-4 Oligo Top 2 | 61 |
| 34 | CATACTCTCAGGTGTCGCGCTTTCGCT AGTACCCGGCGTTT | Linker-4 Oligo Bottom 2 | 62 |
| 35 | ACGGCTCTTCGATGCCCAAAAAGAAG AGGAAAGT | mTN3 N-terminus | 63 |
| 36 | AGCGCTCTTCATCTGTCTACAGTCCTC CTGCG | mTN3 Catalytic domain R, SapI | 64 |
| 37 | ACGGCTCTTCGCATTTTTTTCCCGGGG GATCC | Cas9 N-terminus R SapI | 65 |
| 38 | GCGCTCTTCAGCCATCGGCACAAACA GCG | Cas9 D10A, F SapI | 66 |
| 39 | ACGGCTCTTCGGGCGAGCCCAATGGA GTACTTCTT | Cas9 D10A, R SapI | 67 |
| 40 | GCGCTCTTCAGCCATCGTGCCCCAGTC TTTT | Cas9 H840A F SapI | 68 |
| 41 | ACGGCTCTTCGGGCATCCACGTCGTA GTCGGAG | Cas9 H840A R SapI | 69 |
| 42 | ATACACCGGTGCCACCATGCCCAAAA AGAAGAGGAAAGT | iCas9 F, Agel | 70 |
| 43 | GATGACAATTGTCACACCTTCCTCTTC TTCTTG | iCas9 R, MfeI | 71 |
| 44 | GTGAGAATTCTCTTTGAAAAGATAAT GTATGATTATGC | Yeast sgRNA cassette F, EcoRI | 72 |
| 45 | ACGGCTCTTCGTCTTTGAAAAGATAAT GTATGATTATGC | Yeast sgRNA cassette R, SapI | 73 |
| 46 | ACGGCTCTTCGAGAGTCTCCAATTATC TAGTAAAAAAAGCACC | Yeast sgRNA cassette F, SapI | 74 |
| 47 | CGTCATGTCACTAGTAGAGTCTCCAAT TATCTAGTAAAAAAAGCACC | Yeast sgRNA cassette R, SpeI | 75 |
| 48 | GTGAGAATTCGAGGGCCTATTTCCCA TGAT | Human sgRNA cassette F, EcoRI | 76 |
| 49 | ACGGCTCTTCGTCTGTCTGCAGAATTG GCG | Human sgRNA cassette R, SapI | 77 |
| 50 | AGCGCTCTTCTAGAGAGGGCCTATTTC CCATGAT | Human sgRNA cassette F, SapI | 78 |
| 51 | CGTCATGTCTCTAGATTTGTCTGCAGA ATTGGCG | Human sgRNA cassette R, SpeI | 79 |
| 52 | ATCCGAACGTACGAGTGCAAGCC | Yeast sg(A) Top | 80 |
| 53 | AACGGCTTGCACTCGTACGTTCG | Yeast sg(A) Bottom | 81 |
| 54 | ATCGAACGTACGAGTGCAAGCCT | Yeast sg(C) Top | 82 |
| 55 | AACAGGCTTGCACTCGTACGTTC | Yeast sg(C) Bottom | 83 |
| 56 | ATCAACGTACGAGTGCAAGCCTG | Yeast sg(E) Top | 84 |
| 57 | AACCAGGCTTGCACTCGTACGTT | Yeast sg(E) Bottom | 85 |

TABLE 2-continued

| Primer | Sequence | Note: | SEQ ID NO. |
|---|---|---|---|
| 58 | ATCACGTACGAGTGCAAGCCTGG | Yeast sg(G) Top | 86 |
| 59 | AACCCAGGCTTGCACTCGTACGT | Yeast sg(G) Bottom | 87 |
| 60 | ATCACGAGTGCAAGCCTGGGGGA | Yeast sg(I) Top | 88 |
| 61 | AACTCCCCCAGGCTTGCACTCGT | Yeast sg(I) Bottom | 89 |
| 62 | ATCTGCAAGCCTGGGGGATGGAT | Yeast sg(K) Top | 90 |
| 63 | AACATCCATCCCCCAGGCTTGCA | Yeast sg(K) Bottom | 91 |
| 64 | ATCCAGACAGACCATACTCCAGA | Yeast sg(B) Top | 92 |
| 65 | AACTCTGGAGTATGGTCTGTCTG | Yeast sg(B) Bottom | 93 |
| 66 | ATCAGACAGACCATACTCCAGAT | Yeast sg(D) Top | 94 |
| 67 | AACATCTGGAGTATGGTCTGTCT | Yeast sg(D) Bottom | 95 |
| 68 | ATCGACAGACCATACTCCAGATG | Yeast sg(F) Top | 96 |
| 69 | AACCATCTGGAGTATGGTCTGTC | Yeast sg(F) Bottom | 97 |
| 70 | ATCACAGACCATACTCCAGATGG | Yeast sg(H) Top | 98 |
| 71 | AACCCATCTGGAGTATGGTCTGT | Yeast sg(H) Bottom | 99 |
| 72 | ATCACCATACTCCAGATGGGGGA | Yeast sg(J) Top | 100 |
| 73 | AACTCCCCCATCTGGAGTATGGT | Yeast sg(J) Bottom | 101 |
| 74 | ATCACTCCAGATGGGGGATGGCT | Yeast sg(L) Top | 102 |
| 75 | AACAGCCATCCCCCATCTGGAGT | Yeast sg(L) Bottom | 103 |
| 76 | CACCGACGTACGAGTGCAAGCCTGG | Human sg(G) Top | 104 |
| 77 | AAACCCAGGCTTGCACTCGTACGTC | Human sg(G) Bottom | 105 |
| 78 | CACCGACAGACCTTACTCCAGAAGG | Human sg(H) Top | 106 |
| 79 | AAACCCTTCTGGAGTAAGGTCTGTC | Human sg(H) Bottom | 107 |
| 80 | CACCGTGCAAGCCTGGGGGAAGGAT | Human sg(K) Top | 108 |
| 81 | AAACATCCTTCCCCCAGGCTTGCAC | Human sg(K) Bottom | 109 |
| 82 | CACCGACTCCAGAAGGGGGAAGGCT | Human sg(L) Top | 110 |
| 83 | AAACAGCCTTCCCCCTTCTGGAGTC | Human sg(L) Bottom | 111 |
| 84 | CACCGACGAGTGCAAGCCTGGGGGA | Human sg(I) Top | 112 |
| 85 | AAACTCCCCCAGGCTTGCACTCGTC | Human sg(I) Top | 113 |
| 86 | CACCGACCTTACTCCAGAAGGGGGA | Human sg(J) Top | 114 |
| 87 | AAACTCCCCCTTCTGGAGTAAGGTC | Human sg(J) Bottom | 115 |

The nucleic acid sequences for the exemplary guide sequences are listed below set forth in SEQ IN NOs. 116-119. The nucleic acid sequence and the amino acid sequence of an exemplary Cas9 fusion protein are listed below and set forth in SEQ ID NOs. 2 and 3.

iCas9-site (Yeast) (88 bp) (SEQ ID NO. 116): sg(G:H) underlined, PAMs bolded, TN3 Res1 sequence italicized

TCCGATCCATCCCCCAGGCTTGCACTCGTA*CGTTCGAAATATTATAAATT*

*ATCAGACA*GACCATACTCCAGATGGGGGATGGCTAGGT iCas9-site (Human) (88 bp) (SEQ ID NO. 117): sg(G:H) underlined, PAMs bolded, TN3 Res1 sequence italicized

TCCGATCCTTCCCCCAGGCTTGCACTCGTA*CGTTCGAAATATTATAAATT*

*ATCAGACA*GACCTTACTCCAGAAGGGGGAAGGCTAGGT iCas9-site (Human) with Accessory Targets (123 bp) (SEQ ID NO. 118): sg(G:H) and sg(M) underlined, PAMs bolded, TN3 Res1 sequence italicized

TCCGATCCTTCCCCCAGGCTTGCACTCGTACGT*TCGAAATATTATAAATT*

*ATCAG*ACAGACCTTACTCCAGAAGGGGGAAGGCTAGGTGGCTACCGGTCG

CCACCATGGTGAGCAAGGGCGAG iCas9-site (Human) with Accessory Targets (123 bp) (SEQ ID NO. 119): sg(G:H) and sg(N) underlined, PAMs bolded, TN3 Res1 sequence italicized

TCCGATCCTTCCCCCAGGCTTGCACTCGTACGT*TCGAAATATTATAAATT*

*ATCAG*ACAGACCTTACTCCAGAAGGGGGAAGGCTAGGTGGCTACCGGTCG

CCACCATGGTGAGCAAGGGCGAG iCas9 Amino Acid Sequence (NLS-GGS-mTN3-GGS*6-dCas9-NLS) (1556 aa) (SEQ ID NO. 1): SV40 NLS underlined, mTN3 Catalytic Domain (TN3-TnpR G70S, D102Y, E124Q) bolded, GGS*6 Interdomain Linker italicized, dCas9 (Cas9 D10A, H840A) without modifications

MPKKKRKVGGSMRIFGYARVSTSQQSLDIQIRALKDAGVKANRIFTDKAS

GSSTDREGLDLLRMKVEEGDVILVKKLDRLSRDTADMIQLIKEFDAQGVA

VRFIDDGISTDGYMGQMVVTILSAVAQAERRRILQRTNEGRQEAKLKGIK

FGRRRTVDR*GGSGGSGGSGGSGGSGGS*MDKKYSIGLAIGTNSVGWAVITD

EYKVPSKKFKVLGNTDRHSIKKNLIGALLFDSGETAEATRLKRTARRRYT

RRKNRICYLQEIFSNEMAKVDDSFFHRLEESFLVEEDKKHERHPIFGNIV

DEVAYHEKYPTIYHLRKKLVDSTDKADLRLIYLALAHMIKFRGHFLIEGD

LNPDNSDVDKLFIQLVQTYNQLFEENPINASGVDAKAILSARLSKSRRLE

NLIAQLPGEKKNGLFGNLIALSLGLTPNFKSNFDLAEDAKLQLSKDTYDD

DLDNLLAQIGDQYADLFLAAKNLSDAILLSDILRVNTEITKAPLSASMIK

RYDEHHQDLTLLKALVRQQLPEKYKEIFFDQSKNGYAGYIDGGASQEEFY

KFIKPILEKMDGTEELLVKLNREDLLRKQRTFDNGSIPHQIHLGELHAIL

RRQEDFYPFLKDNREKIEKILTFRIPYYVGPLARGNSRFAWMTRKSEETI

TPWNFEEVVDKGASAQSFIERMTNFDKNLPNEKVLPKHSLLYEYFTVYNE

LTKVKYVTEGMRKPAFLSGEQKKAIVDLLFKTNRKVTVKQLKEDYFKKIE

CFDSVEISGVEDRFNASLGTYHDLLKIIKDKDFLDNEENEDILEDIVLTL

TLFEDREMIEERLKTYAHLFDDKVMKQLKRRRYTGWGRLSRKLINGIRDK

QSGKTILDFLKSDGFANRNFMQLIHDDSLTFKEDIQKAQVSGQGDSLHEH

IANLAGSPAIKKGILQTVKVVDELVKVMGRHKPENIVIEMARENQTTQKG

QKNSRERMKRIEEGIKELGSQILKEHPVENTQLQNEKLYLYYLQNGRDMY

VDQELDINRLSDYDVDAIVPQSFLKDDSIDNKVLTRSDKNRGKSDNVPSE

EVVKKMKNYWRQLLNAKLITQRKFDNLTKAERGGLSELDKAGFIKRQLVE

TRQITKHVAQILDSRMNTKYDENDKLIREVKVITLKSKLVSDFRKDFQFY

KVREINNYHHAHDAYLNAVVGTALIKKYPKLESEFVYGDYKVYDVRKMIA

KSEQEIGKATAKYFFYSNIMNFFKTEITLANGEIRKRPLIETNGETGEIV

WDKGRDFATVRKVLSMPQVNIVKKTEVQTGGFSKESILPKRNSDKLIARK

KDWDPKKYGGFDSPTVAYSVLVVAKVEKGKSKKLKSVKELLGITIMERSS

FEKNPIDFLEAKGYKEVKKDLIIKLPKYSLFELENGRKRMLASAGELQKG

-continued

NELALPSKYVNFLYLASHYEKLKGSPEDNEQKQLFVEQHKHYLDEIIEQI

SEFSKRVILADANLDKVLSAYNKHRDKPIREQAENIIHLFTLTNLGAPAA

FKYFDTTIDRKRYTSTKEVLDATLIHQSITGLYETRIDLSQLGGDSRADP

KKKRKV

REFERENCES (1) Cong, L.; Ran, F. A.; Cox, D.; Lin, S.; Barretto, R.; Habib, N.; Hsu, P. D.; Wu, X.; Jiang, W.; Marraffini, L. A.; et al. Multiplex Genome Engineering Using CRISPR/Cas Systems. Science 2013, 339 (6121), 819-823. https://doi.org/10.1126/science.1231143.

(2) Mali, P.; Yang, L.; Esvelt, K. M.; Aach, J.; Guell, M.; DiCarlo, J. E.; Norville, J. E.; Church, G. M. RNA-Guided Human Genome Engineering via Cas9. Science 2013, 339 (6121), 823-826. https://doi.org/10.1126/science.1232033.

(3) Zetsche, B.; Gootenberg, J. S.; Abudayyeh, O. O.; Slaymaker, I. M.; Makarova, K. S.; Essletzbichler, P.; Volz, S. E.; Joung, J.; van der Oost, J.; Regev, A.; et al. Cpf1 Is a Single RNA-Guided Endonuclease of a Class 2 CRISPR-Cas System. Cell 2015, 163 (3), 759-771. https://doi.org/10.1016/j.cell.2015.09.038.

(4) Sander, J. D.; Joung, J. K. CRISPR-Cas Systems for Editing, Regulating and Targeting Genomes. Nat. Biotechnol. 2014, 32 (4), 347-355. https://doi.org/10.1038/nbt.2842.

(5) Brookhouser, N.; Raman, S.; Potts, C.; Brafman, D. A. May I Cut in? Gene Editing Approaches in Human Induced Pluripotent Stem Cells. Cells 2017, 6 (1). https://doi.org/10.3390/cells6010005.

(6) Suzuki, K.; Tsunekawa, Y.; Hernandez-Benitez, R.; Wu, J.; Zhu, J.; Kim, E. J.; Hatanaka, F.; Yamamoto, M.; Araoka, T.; Li, Z.; et al. In Vivo Genome Editing via CRISPR/Cas9 Mediated Homology-Independent Targeted Integration. Nature 2016, 540 (7631), 144-149. https://doi.org/10.1038/nature20565.

(7) He, X.; Tan, C.; Wang, F.; Wang, Y.; Zhou, R.; Cui, D.; You, W.; Zhao, H.; Ren, J.; Feng, B. Knock-in of Large Reporter Genes in Human Cells via CRISPR/Cas9-Induced Homology-Dependent and Independent DNA Repair. Nucleic Acids Res. 2016, 44 (9), e85. https://doi.org/10.1093/nar/gkw064.

(8) Schmid-Burgk, J. L.; Höning, K.; Ebert, T. S.; Hornung, V. CRISPaint Allows Modular Base-Specific Gene Tagging Using a Ligase-4-Dependent Mechanism. Nat. Commun. 2016, 7, 12338. https://doi.org/10.1038/ncomms12338.

(9) Orthwein, A.; Noordermeer, S. M.; Wilson, M. D.; Landry, S.; Enchev, R. I.; Sherker, A.; Munro, M.; Pinder, J.; Salsman, J.; Dellaire, G.; et al. A Mechanism for the Suppression of Homologous Recombination in G1 Cells. Nature 2015, advance online publication. https://doi.org/10.1038/nature16142.

(10) Ihry, R. J.; Worringer, K. A.; Salick, M. R.; Frias, E.; Ho, D.; Theriault, K.; Kommineni, S.; Chen, J.; Sondey, M.; Ye, C.; et al. P53 Inhibits CRISPR-Cas9 Engineering in Human Pluripotent Stem Cells. Nat. Med. 2018, 24 (7), 939-946. https://doi.org/10.1038/s41591-018-0050-6.

(11) Haapaniemi, E.; Botla, S.; Persson, J.; Schmierer, B.; Taipale, J. CRISPR-Cas9 Genome Editing Induces a P53-Mediated DNA Damage Response. Nat. Med. 2018, 24 (7), 927. https://doi.org/10.1038/s41591-018-0049-z.

(12) Fu, Y.; Foden, J. A.; Khayter, C.; Maeder, M. L.; Reyon, D.; Joung, J. K.; Sander, J. D. High-Frequency off-Target Mutagenesis Induced by CRISPR-Cas Nucleases in Human Cells. Nat. Biotechnol. 2013, 31 (9), 822-826. https://doi.org/10.1038/nbt.2623.

(13) Kosicki, M.; Tomberg, K.; Bradley, A. Repair of Double-Strand Breaks Induced by CRISPR-Cas9 Leads to Large Deletions and Complex Rearrangements. Nat. Biotechnol. 2018, 36 (8), 765-771. https://doi.org/10.1038/nbt.4192.

(14) Komor, A. C.; Kim, Y. B.; Packer, M. S.; Zuris, J. A.; Liu, D. R. Programmable Editing of a Target Base in Genomic DNA without Double-Stranded DNA Cleavage. Nature 2016, 533 (7603), 420-424. https://doi.org/10.1038/nature17946.

(15) Komor, A. C.; Zhao, K. T.; Packer, M. S.; Gaudelli, N. M.; Waterbury, A. L.; Koblan, L. W.; Kim, Y. B.; Badran, A. H.; Liu, D. R. Improved Base Excision Repair Inhibition and Bacteriophage Mu Gam Protein Yields C:G-to-T:A Base Editors with Higher Efficiency and Product Purity. Sci. Adv. 2017, 3 (8), eaao4774. https://doi.org/10.1126/sciadv.aao4774.

(16) Gaj, T.; Sirk, S. J.; Barbas, C. F. Expanding the Scope of Site-Specific Recombinases for Genetic and Metabolic Engineering. Biotechnol. Bioeng. 2014, 111 (1), 1-15. https://doi.org/10.1002/bit.25096.

(17) Standage-Beier, K.; Wang, X. Genome Reprogramming for Synthetic Biology. Front. Chem. Sci. Eng. 2017, 11 (1), 37-45. https://doi.org/10.1007/s11705-017-1618-2.

(18) Grindley, N. D. F.; Whiteson, K. L.; Rice, P. A. Mechanisms of Site-Specific Recombination. Annu. Rev. Biochem. 2006, 75 (1), 567-605. https://doi.org/10.1146/annurev.biochem.73.011303.073908.

(19) Brafman, D.; Willert, K. Gene Transduction Approaches in Human Embryonic Stem Cells. Methodol. Adv. Cult. Manip. Util. Embryonic Stem Cells Basic Pract. Appl. 2011. https://doi.org/10.5772/14163.

(20) St-Pierre, F.; Cui, L.; Priest, D. G.; Endy, D.; Dodd, I. B.; Shearwin, K. E. One-Step Cloning and Chromosomal Integration of DNA. ACS Synth. Biol. 2013, 2 (9), 537-541. https://doi.org/10.1021/sb400021j.

(21) Karpinski, J.; Hauber, I.; Chemnitz, J.; Schafer, C.; Paszkowski-Rogacz, M.; Chakraborty, D.; Beschorner, N.; Hofmann-Sieber, H.; Lange, U. C.; Grundhoff, A.; et al. Directed Evolution of a Recombinase That Excises the Provirus of Most HIV-1 Primary Isolates with High Specificity. Nat. Biotechnol. 2016, 34 (4), 401-409. https://doi.org/10.1038/nbt.3467.

(22) Akopian, A.; He, J.; Boocock, M. R.; Stark, W. M. Chimeric Recombinases with Designed DNA Sequence Recognition. Proc. Natl. Acad. Sci. 2003, 100 (15), 8688-8691. https://doi.org/10.1073/pnas.1533177100.

(23) Mercer, A. C.; Gaj, T.; Fuller, R. P.; Barbas, C. F. Chimeric TALE Recombinases with Programmable DNA Sequence Specificity. Nucleic Acids Res. 2012, gks875. https://doi.org/10.1093/nar/gks875.

(24) Gordley, R. M.; Gersbach, C. A.; Barbas, C. F. Synthesis of Programmable Integrases. Proc. Natl. Acad. Sci. 2009, 106 (13), 5053-5058. https://doi.org/10.1073/pnas.0812502106.

(25) Arnold, P. H.; Blake, D. G.; Grindley, N. D.; Boocock, M. R.; Stark, W. M. Mutants of Tn3 Resolvase Which Do Not Require Accessory Binding Sites for Recombination Activity. EMBO J. 1999, 18 (5), 1407-1414. https://doi.org/10.1093/emboj/18.5.1407.

(26) Prorocic, M. M.; Wenlong, D.; Olorunniji, F. J.; Akopian, A.; Schloetel, J.-G.; Hannigan, A.; McPherson, A. L.; Stark, W. M. Zinc-Finger Recombinase Activities in Vitro. Nucleic Acids Res. 2011, 39 (21), 9316-9328. https://doi.org/10.1093/nar/gkr652.

(27) Yang, W.; Steitz, T. A. Crystal Structure of the Site-Specific Recombinase Gamma Delta Resolvase Complexed with a 34 Bp Cleavage Site. Cell 1995, 82 (2), 193-207.

(28) Li, W.; Kamtekar, S.; Xiong, Y.; Sarkis, G. J.; Grindley, N. D. F.; Steitz, T. A. Structure of a Synaptic Γδ Resolvase Tetramer Covalently Linked to Two Cleaved DNAs. Science 2005, 309 (5738), 1210-1215. https://doi.org/10.1126/science.1112064.

(29) Guilinger, J. P.; Thompson, D. B.; Liu, D. R. Fusion of Catalytically Inactive Cas9 to FokI Nuclease Improves the Specificity of Genome Modification. Nat. Biotechnol. 2014, 32 (6), 577-582. https://doi.org/10.1038/nbt.2909.

(30) Nishimasu, H.; Ran, F. A.; Hsu, P. D.; Konermann, S.; Shehata, S. I.; Dohmae, N.; Ishitani, R.; Zhang, F.; Nureki, O. Crystal Structure of Cas9 in Complex with Guide RNA and Target DNA. Cell 2014, 156 (5), 935-949. https://doi.org/10.1016/j.cell.2014.02.001.

(31) Standage-Beier, K.; Zhang, Q.; Wang, X. Targeted Large-Scale Deletion of Bacterial Genomes Using CRISPR-Nickases. ACS Synth. Biol. 2015, 4 (11), 1217-1225. https://doi.org/10.1021/acssynbio.5b00132.

(32) DiCarlo, J. E.; Norville, J. E.; *Mali*, P.; Rios, X.; Aach, J.; Church, G. M. Genome Engineering in *Saccharomyces Cerevisiae* Using CRISPR-Cas Systems. Nucleic Acids Res. 2013, 41 (7), 4336-4343. https://doi.org/10.1093/nar/gkt135.

(33) Chaikind, B.; Bessen, J. L.; Thompson, D. B.; Hu, J. H.; Liu, D. R. A Programmable Cas9-Serine Recombinase Fusion Protein That Operates on DNA Sequences in Mammalian Cells. Nucleic Acids Res. 2016, 44 (20), 9758-9770. https://doi.org/10.1093/nar/gkw707.

(34) Nöllmann, M.; Byron, O.; Stark, W. M. Behavior of Tn3 Resolvase in Solution and Its Interaction with Res. Biophys. J. 2005, 89 (3), 1920-1931. https://doi.org/10.1529/biophysj.104.058164.

(35) Cremer, T.; Cremer, M. Chromosome Territories. Cold Spring Harb. Perspect. Biol. 2010, 2 (3). https://doi.org/10.1101/cshperspect.a003889.

(36) Gordley, R. M.; Smith, J. D.; Gräslund, T.; Barbas, C. F. Evolution of Programmable Zinc Finger-Recombinases with Activity in Human Cells. J. Mol. Biol. 2007, 367 (3), 802-813. https://doi.org/10.1016/j.jmb.2007.01.017.

(37) Gaj, T.; Mercer, A. C.; Gersbach, C. A.; Gordley, R. M.; Barbas, C. F. Structure-Guided Reprogramming of Serine Recombinase DNA Sequence Specificity. Proc. Natl. Acad. Sci. 2011, 108 (2), 498-503. https://doi.org/10.1073/pnas.1014214108.

(38) Gaj, T.; Mercer, A. C.; Sirk, S. J.; Smith, H. L.; Barbas, C. F. A Comprehensive Approach to Zinc-Finger Recombinase Customization Enables Genomic Targeting in Human Cells. Nucleic Acids Res. 2013, 41 (6), 3937-3946. https://doi.org/10.1093/nar/gkt071.

(39) Hu, J. H.; Miller, S. M.; Geurts, M. H.; Tang, W.; Chen, L.; Sun, N.; Zeina, C. M.; Gao, X.; Rees, H. A.; Lin, Z.; et al. Evolved Cas9 Variants with Broad PAM Compatibility and High DNA Specificity. Nature 2018, 556 (7699), 57-63. https://doi.org/10.1038/nature26155.

(40) Chatterjee, P.; Jakimo, N.; Jacobson, J. M. Minimal PAM Specificity of a Highly Similar SpCas9 Ortholog. Sci. Adv. 2018, 4 (10), eaau0766. https://doi.org/10.1126/sciadv.aau0766.

(41) Nami, F.; Basiri, M.; Satarian, L.; Curtiss, C.; Baharvand, H.; Verfaillie, C. Strategies for In Vivo Genome Editing in Nondividing Cells. Trends Biotechnol. 2018, 36 (8), 770-786. https://doi.org/10.1016/j.tibtech.2018.03.004.

(42) Siuti, P.; Yazbek, J.; Lu, T. K. Synthetic Circuits Integrating Logic and Memory in Living Cells. Nat. Biotechnol. 2013, 31 (5), 448-452. https://doi.org/10.1038/nbt.2510.

(43) Yang, L.; Nielsen, A. A. K.; Fernandez-Rodriguez, J.; McClune, C. J.; Laub, M. T.; Lu, T. K.; Voigt, C. A. Permanent Genetic Memory with >1-Byte Capacity. Nat. Methods 2014, 11 (12), 1261-1266. https://doi.org/10.1038/nmeth.3147.

(44) Weinberg, B. H.; Pham, N. T. H.; Caraballo, L. D.; Lozanoski, T.; Engel, A.; Bhatia, S.; Wong, W. W. Large-Scale Design of Robust Genetic Circuits with Multiple Inputs and Outputs for Mammalian Cells. Nat. Biotechnol. 2017, 35 (5), 453-462. https://doi.org/10.1038/nbt.3805.

(45) Sikorski, R. S.; Hieter, P. A System of Shuttle Vectors and Yeast Host Strains Designed for Efficient Manipulation of DNA in *Saccharomyces Cerevisiae*. Genetics 1989, 122 (1), 19-27.

(46) Ellis, T.; Wang, X.; Collins, J. J. Diversity-Based, Model-Guided Construction of Synthetic Gene Networks with Predicted Functions. Nat. Biotechnol. 2009, 27 (5), 465-471. https://doi.org/10.1038/nbt.1536.s

The invention claimed is:

1. A fusion protein consisting of the amino acid sequence of SEQ ID NO: 1.

2. A kit comprising:

a fusion protein;

a first and second single guide RNA (sgRNA), each sgRNA targets the fusion protein to a first and second sgRNA target sequence on a DNA molecule; and a third sgRNA targeting an accessory sequence on the opposite strand as the target sequence for the second sgRNA;

wherein;

the fusion protein comprises:

a catalytically inactive Cas9;

a catalytic domain of a hyperactive Tn3 transposon resolvase;

a first linker, wherein the first linker connects the C-terminus of the catalytic domain of the hyperactive Tn3 transposon resolvase to the N-terminus of the catalytically inactive Cas9;

a first nuclear localization signal; and a second linker, wherein the second linker connects the first nuclear localization signal to the C-terminus of the catalytically inactive Cas9 or the N-terminus of the catalytic domain of the hyperactive Tn3 transposon resolvase, the first and second sgRNAs target sequences on opposite strands of the DNA molecule flanking a Tn3 core recognition sequence and are positioned at equal distances around the Tn3 core recognition sequence;

the first and second sgRNA target sequences are spaced to position the 5' ends of the first and second sgRNAs 22 bp apart, whereby the first and second sgRNAs are on the same helical face of the DNA molecule and the catalytic domains of the hyperactive Tn3 transposon resolvases are positioned to have activity on the Tn3 core recognition sequence; and the accessory sequence is adjacent to the Tn3 core recognition sequence flanked by the first and second sgRNA target sequences and the 3' end of the target sequence for the second sgRNA and the 3' end of the accessory sequence for the third sgRNA are spaced 21 bp apart.

3. A method of deleting a target sequence from the genome in a eukaryotic cell, comprising introducing into a eukaryotic cell the items in the kit of claim 2.

4. A method of inserting an extraneous sequence into a target region of a genome in a eukaryotic cell, comprising introducing into a eukaryotic cell the items in the kit of claim 2.

5. The kit of claim 2, wherein the fusion protein and sgRNAs are encoded on one or more expression vectors.

6. The kit of claim 2, wherein the fusion protein has an amino acid sequence of SEQ ID NO. 1.

7. The kit of claim 2, wherein the amino acid sequence of the first linker consists of six repeats of GGS.

8. The kit of claim 2, wherein the amino acid sequence of the first linker comprises SEQ ID NO. 120.

9. The kit of claim 2, wherein the amino acid sequence of the first linker comprises SEQ ID NO. 121.

10. The kit of claim 2, wherein the fusion protein further comprises:

a second nuclear localization signal, wherein the first nuclear localization signal adjacent to the C-terminus of the catalytically inactive Cas9 and the second nuclear localization signal is adjacent to the N-terminus of the catalytic domain of the hyperactive Tn3 transposon resolvase; and a third linker, wherein the second linker connects the first nuclear localization signal to the C-terminus of the catalytically inactive Cas9 and the third linker connects the second nuclear localization signals to the N-terminus of the catalytic domain of the hyperactive Tn3 transposon resolvase.

11. The kit of claim 2, wherein the nuclear localization signal is from SV40.

* * * * *